(12) United States Patent
Stupp et al.

(10) Patent No.: US 11,497,788 B2
(45) Date of Patent: *Nov. 15, 2022

(54) SUPRAMOLECULAR GLYCOSAMINOGLYCANS

(71) Applicant: Northwestern University, Evanston, IL (US)

(72) Inventors: Samuel I. Stupp, Chicago, IL (US); Bo Timmy Bjorn Fyrner, Linkoping (SE); Sung Soo Lee, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/030,035

(22) Filed: Sep. 23, 2020

(65) Prior Publication Data

US 2021/0015888 A1 Jan. 21, 2021

Related U.S. Application Data

(63) Continuation of application No. 15/566,066, filed as application No. PCT/US2016/027292 on Apr. 13, 2016, now Pat. No. 10,792,327.

(60) Provisional application No. 62/147,350, filed on Apr. 14, 2015.

(51) Int. Cl.
| | |
|---|---|
| *A61K 38/14* | (2006.01) |
| *C07K 14/00* | (2006.01) |
| *A61K 47/54* | (2017.01) |
| *A61K 47/69* | (2017.01) |
| *A61L 27/48* | (2006.01) |
| *A61K 9/70* | (2006.01) |
| *A61K 35/12* | (2015.01) |
| *C07K 9/00* | (2006.01) |

(52) U.S. Cl.
CPC ............... *A61K 38/14* (2013.01); *A61K 9/70* (2013.01); *A61K 35/12* (2013.01); *A61K 47/542* (2017.08); *A61K 47/549* (2017.08); *A61K 47/6907* (2017.08); *A61L 27/48* (2013.01); *C07K 9/003* (2013.01); *C07K 14/00* (2013.01); *A61L 2300/414* (2013.01); *A61L 2400/12* (2013.01)

(58) Field of Classification Search
CPC .............................. A61K 38/14; C07K 14/00
See application file for complete search history.

(56) References Cited

U.S. PATENT DOCUMENTS

| | | | |
|---|---|---|---|
| 8,580,923 B2 | 11/2013 | Stupp et al. | |
| 2011/0020917 A1* | 1/2011 | Wen .................... | B05D 3/067 525/50 |
| 2012/0264912 A1* | 10/2012 | Stupp .................... | A61P 19/02 530/328 |
| 2013/0116789 A1* | 5/2013 | Chachques .......... | A61F 2/2481 623/14.13 |
| 2018/0125924 A1 | 5/2018 | Stupp et al. | |

FOREIGN PATENT DOCUMENTS

WO WO 2016/168302 10/2016

OTHER PUBLICATIONS

Restuccia et al., 2015, Self-assembled glycopeptide nanofibers as modulators of galectin-1 bioactivity, Cell Mol Bioeng, 8(3): 471-487.*
Matson et al., 2011, Drug release from hydrazine-containing peptide amphiphiles, Chem Commun, 47(28): 7962-7964.*
Khan et al., 2012, Self-Assembling Glucagon-Like Peptide 1-Mimetic Peptide Amphiphiles for Enhanced Activity and Proliferation of Insulin-Secreting Cells, Acta Biomater, 8(5): 1685-1692.*
Ashikari-Hada, S, et al. Heparin regulates vascular endothelial growth factor165-dependent mitogenic activity, tube formation, and its receptor phosphorylation of human endothelial cells. Comparison of the effects of heparin and modified heparins. J Biol Chem. Sep. 9, 2005;280(36):31508-15.
Barceloux, D.G, Copper. J Toxicol Clin Toxicol. 1999;37(2):217-30.
Baskaran, S, et al. Glycosaminoglycan-mimetic biomaterials. 3. Glycopolymers prepared from alkene-derivatized mono- and disaccharide-based glycomonomers. Bioconjug Chem. Nov.-Dec. 2002; 13(6):1309-13.
Bearinger JP, et al. Chemisorbed poly(propylene sulphide)-based copolymers resist biomolecular interactions. Nat Mater. Apr. 2003;2(4):259-64.
Billington CJ, et al. Glycosylation of Twisted Gastrulation is Required for BMP Binding and Activity during Craniofacial Development. Front Physiol. Sep. 12, 2011;2:59.
Bramono, DS, et al. Bone marrow-derived heparan sulfate potentiates the osteogenic activity of bone morphogenetic protein-2 (BMP-2). Bone. Apr. 2012;50(4):954-64.
Capila, I, et al. Heparin-protein interactions. Angew Chem Int Ed Engl. Feb. 1, 2002;41(3):391-412.
Chen, B, et al. Carbohydrate rod conjugates: ternary rod-coil molecules forming complex liquid crystal structures. J Am Chem Soc. Nov. 30, 2005;127(47):16578-91.
Chernyak A, et al. Synthesis of carbohydrate-amino acid conjugates related to the capsular antigen K54 from *Escherichia coli* O6:K54:H10 and artificial antigens therefrom. Carbohydr Res. Sep. 2, 1991;216:381-98.
Choi, YJ, et al. The identification of a heparin binding domain peptide from bone morphogenetic protein-4 and its role on osteogenesis. Biomaterials. Oct. 2010;31(28):7226-38.

(Continued)

*Primary Examiner* — Amber D Steele
(74) *Attorney, Agent, or Firm* — Casimir Jones SC; David W. Staple

(57) ABSTRACT

Provided herein are glycosylated peptide amphiphiles (GPAs), supramolecular glyconanostructures assembled therefrom, and methods of use thereof. In particular, provided herein are glycosaminoglycan (GAG) mimetic peptide amphiphiles (PAs) and supramolecular GAG mimetic nanostructures assembled therefrom that mimic the biological activities of GAGs, such as heparin, heparan sulfate, hyaluronic acid etc.

11 Claims, 37 Drawing Sheets

Specification includes a Sequence Listing.

(56) References Cited

OTHER PUBLICATIONS

Chou, YF, et al. In vitro response of MC3T3-E1 pre-osteoblasts within three-dimensional apatite-coated PLGA scaffolds. J Biomed Mater Res B Appl Biomater. Oct. 2005;75(1):81-90.

Cui, H, et al., Self-assembly of peptide amphiphiles: from molecules to nanostructures to biomaterials. Biopolymers. 2010;94(1):1-18.

Digabriele, AD, et al. Structure of a heparin-linked biologically active dimer of fibroblast growth factor. Nature. Jun. 25, 1998;393(6687):812-7.

Eklind, K, et al. Large-scale synthesis of a Lewis B tetrasaccharide derivative, its acrylamide copolymer, and related di- and trisaccharides for use in adhesion inhibition studies with Helicobacter pylori. J Carbohyd Chem. 1996;15(9):1161-78.

Eming, SA, et al. Tomic-Canic M. Wound repair and regeneration: mechanisms, signaling, and translation. Sci Transl Med. Dec. 3, 2014;6(265):265sr6.

Fairweather, JK, et al. Synthesis of a heparan sulfate mimetic disaccharide with a conformationally locked residue from a common intermediate. Carbohydr Res. Nov. 23, 2009;344(17):2394-8.

Fyrner T, et al. Saccharide-Functionalized Alkanethiols for Fouling-Resistant Self-Assembled Monolayers: Synthesis, Monolayer Properties, and Antifouling Behavior. Langmuir. Dec. 20, 2011;27(24):15034-47.

Gandhi, NS, et al. The Structure of Glycosaminoglycans and their Interactions with Proteins. Chem Biol Drug Des. Dec. 2008;72(6):455-82.

Gursoy, D, et al. TomoPy: a framework for the analysis of synchrotron tomographic data. J Synchrotron Radiat. Sep. 2014;21(Pt 5):1188-93.

Hartgerink, JD, et al. Self-assembly and mineralization of peptide-amphiphile nanofibers. Science. Nov. 23, 2001;294(5547):1684-8.

Hsu, WK, et al. Stem cells from human fat as cellular delivery vehicles in an athymic rat posterolateral spine fusion model. J Bone Joint Surg Am. May 2008;90(5):1043-52.

Hudalla, G.A., et al. Glycosylated polypeptide nanofibers as polyvalent lectin inhibitors with enzymatically-tunable binding specificity. Soc for Biomat. 2014; abstract 162.

Israelachvili, J.N. Intermolecular and surface forces; 2nd ed.; Academic: London San Diego, 1992.

Katagiri T, et al. Bone morphogenetic protein-2 converts the differentiation pathway of C2C12 myoblasts into the osteoblast lineage. J Cell Biol. Dec. 1994; 127(6 Pt 1):1755-66.

Kocabey, S, et al. Glycosaminoglycan mimetic peptide nanofibers promote mineralization by osteogenic cells. Acta Biomater. Nov. 2013;9(11):9075-85.

Kuo WJ, et al. Heparan Sulfate Acts as a Bone Morphogenetic Protein Coreceptor by Facilitating Ligand-induced Receptor Hetero-oligomerization. Mol Biol Cell. Nov. 15, 2010;21(22):4028-41.

Lee, SS, et al. Gel scaffolds of BMP-2-binding peptide amphiphile nanofibers for spinal arthrodesis. Adv Healthc Mater. Jan. 7, 2015;4(1):131-141.

Li, YC, et al. Interactions That Influence the Binding of Synthetic Heparan Sulfate Based Disaccharides to Fibroblast Growth Factor-2. ACS Chem Biol. Aug. 15, 2014;9(8):1712-7.

Liu, L, et al. Design, synthesis, FGF-1 binding, and molecular modeling studies of conformationally flexible heparin mimetic disaccharides. Bioorg Med Chem Lett. Jan. 1, 2008;18(1):344-9.

Mammadov, R, et al. Heparin mimetic peptide nanofibers promote angiogenesis. Biomacromolecules. Oct. 10, 2011;12(10):3508-19.

Mammen, M, et al. Polyvalent interactions in biological systems: Implications for design and use of multivalent ligands and inhibitors. Angew Chem Int Ed Engl. Nov. 2, 1998;37(20):2754-2794.

Murali, S, et al. Affinity-selected heparan sulfate for bone repair. Biomaterials. Jul. 2013;34(22):5594-605.

Nguyen, TH, et al. Poly(vinyl sulfonate) Facilitates bFGF-Induced Cell Proliferation. Biomacromolecules. Sep. 14, 2015;16(9):2684-92.

Ornitz, DM, et al. Ligand specificity and heparin dependence of fibroblast growth factor receptors 1 and 3. J Biol Chem. Aug. 15, 1992;267(23):16305-11.

Ortony, JH, et al. Internal dynamics of a supramolecular nanofibre. Nat Mater. Aug. 2014;13(8):812-6.

Paine-Saunders, S, et al. Heparan sulfate proteoglycans retain Noggin at the cell surface—A potential mechanism for shaping bone morphogenetic protein gradients. J Biol Chem. Jan. 18, 2002;277(3):2089-96. Epub Nov. 12, 2001.

Petitou, M, et al. A synthetic antithrombin III binding pentasaccharide is now a drug! What comes next? Angew Chem Int Ed Engl. Jun. 14, 2004;43(24):3118-33.

Rostovtsev, W, et al. A stepwise huisgen cycloaddition process: copper(I)-catalyzed regioselective "ligation" of azides and terminal alkynes. Angew Chem Int Ed Engl. Jul. 15, 2002;41(14):2596-9.

Roy, S, et al. Synthesis and biological evaluation of a unique heparin mimetic hexasaccharide for structure-activity relationship studies. J Med Chem. Jun. 12, 2014;57(11):4511-20.

Rubin, JB, et al. Cerebellar proteoglycans regulate sonic hedgehog responses during development. Development. May 2002;129(9):2223-32.

Ruppert, R, et al. Human Bone Morphogenetic Protein 2 Contains a Heparin-Binding Site which Modifies Its Biological Activity. Eur J Biochem. Apr. 1, 1996;237(1):295-302.

Schlessinger, J, et al. Crystal structure of a ternary FGF-FGFR-heparin complex reveals a dual role for heparin in FGFR binding and dimerization. Mol Cell. Sep. 2000;6(3):743-50.

Silba, G.A. et al. Selective differentiation of neural progenitor cells by high-epitope density nanofibers. Science. Feb. 27, 2004;303(5662):1352-5.

Simmonds, MC, et al. Safety and effectiveness of recombinant human bone morphogenetic protein-2 for spinal fusion: a meta-analysis of individual-participant data. Ann Intern Med. Jun. 18, 2013;158(12):877-89.

Singhal, A, et al. Effect of cyclic loading on the nanoscale deformation of hydroxyapatite and collagen fibrils in bovine bone. Biomech Model Mechanobiol. Jun. 2014;13(3):615-26.

Tantakitti, F, et al. Energy landscapes and functions of supramolecular systems. Nat Mater. Apr. 2016;15(4):469-76.

Tovar, JD, et al. Probing the interior of peptide amphiphile supramolecular aggregates. J Am Chem Soc. May 25, 2005;127(20):7337-45.

Van Teeffelen, JW, et al. Endothelial glycocalyx: sweet shield of blood vessels. Trends Cardiovasc Med. Apr. 2007;17(3):101-5.

Wang, YX, et al. A high-throughput x-ray microtomography system at the Advanced Photon Source. Rev Sci Instrum. 2001;72(4):2062-8.

Webber, MJ, et al. Supramolecular biomaterials. Nat Mater. Jan. 2016;15(1):13-26.

Webber MJ, et al. Switching of Self-Assembly in a Peptide Nanostructure with a Specific Enzyme. Soft Matter. Oct. 21, 2011;7(20):9665-9672.

Xu, D, et al. Demystifying heparan sulfate-protein interactions. Annu Rev Biochem. 2014;83:129-57.

Zhao, B, et al. Heparin Potentiates the in Vivo Ectopic Bone Formation Induced by Bone Morphogenetic Protein-2. J Biol Chem. Aug. 11, 2006;281(32):23246-53.

International Search Report of related PCTUS201627292, dated Jul. 26, 2016, 9 pages.

* cited by examiner

FIG. 1A

| PA | Monosaccharide | Molecular structure |
|---|---|---|
| 1 | 3,4,6S-GlcNAc | |
| 2 | 6S-GlcNAc | |
| 3 | GlcA | |
| 4 | GlcNAc | |
| 5 | --- | |
| 6 | --- | |

FIG. 1B
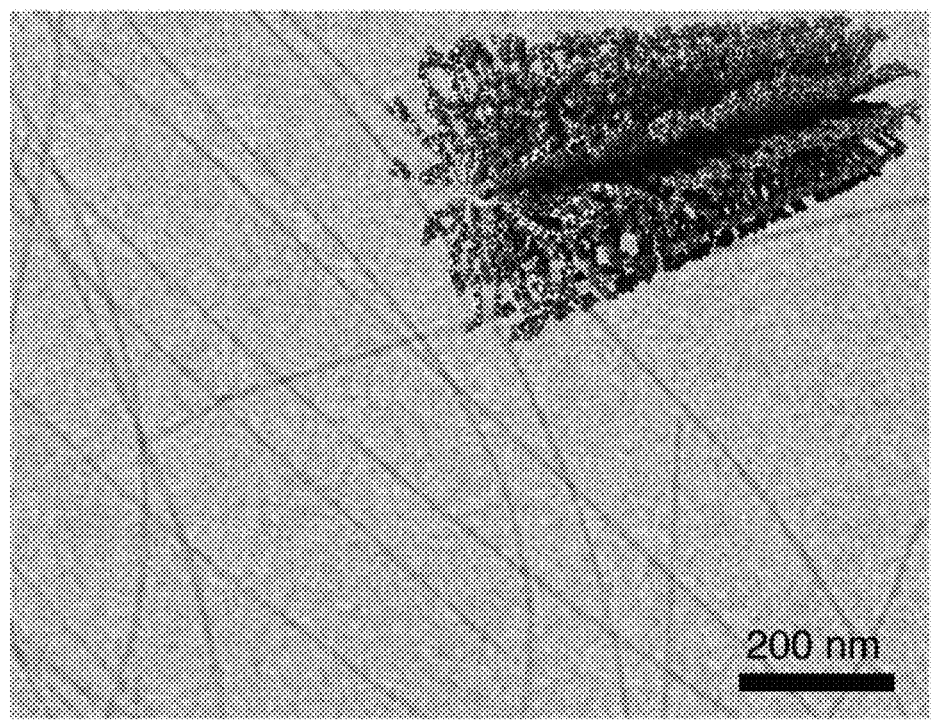
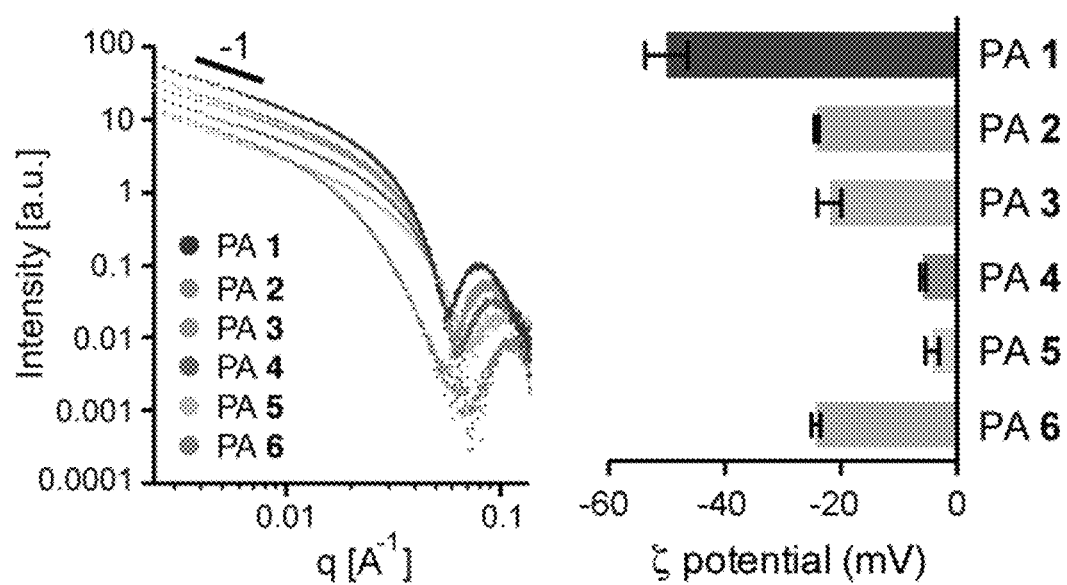
FIG. 1C
FIG. 1D

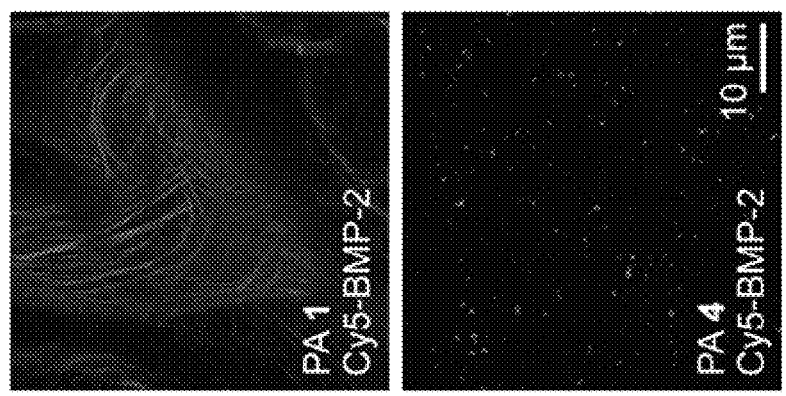
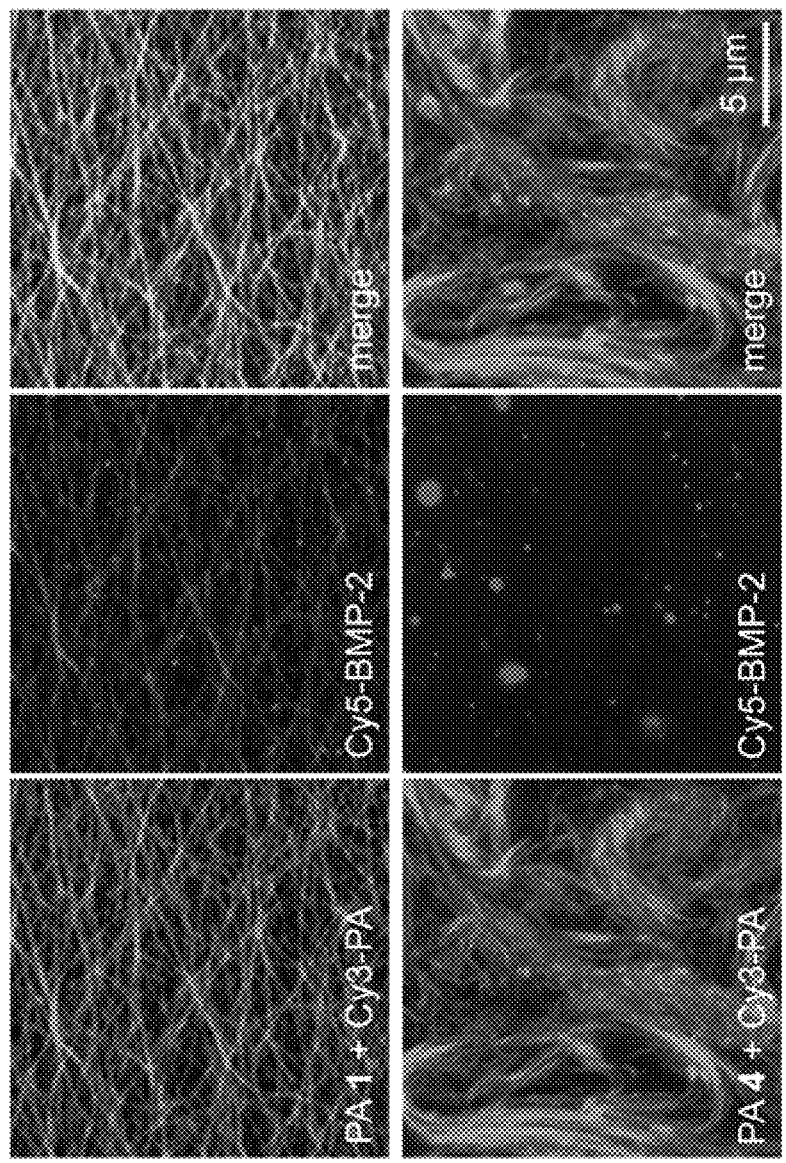

BMP-2    MQAKHKQRKR LKS 13 (SEQ ID NO: 10)
EHBMP-2  MAPTSSSTKK TQL 13 (SEQ ID NO: 17)

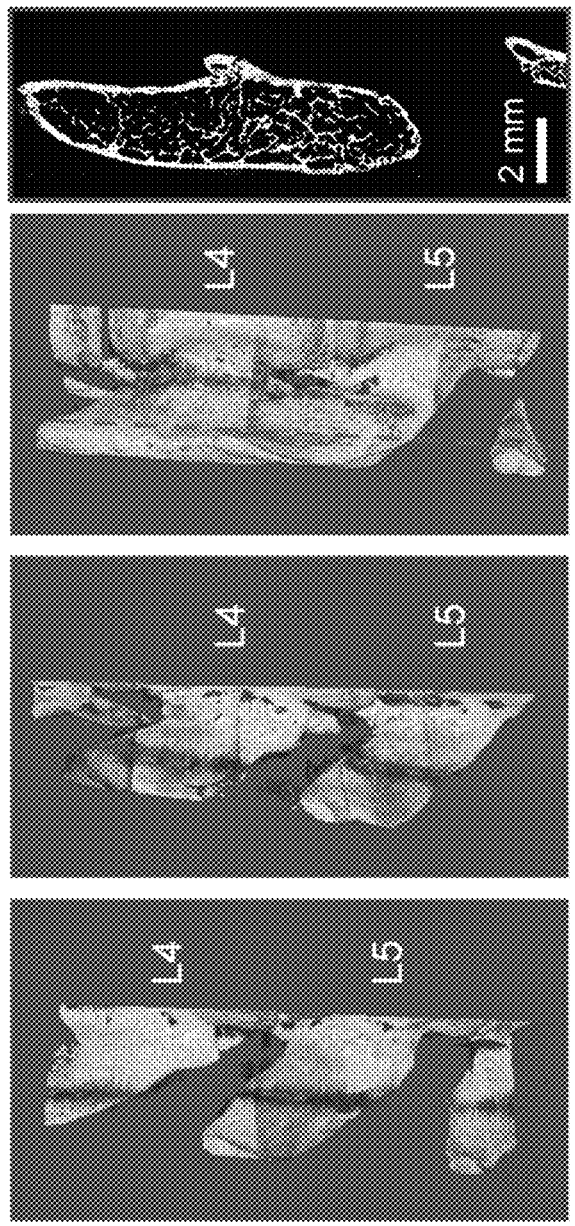

SEQUENCE LISTING

<160> NUMBER OF SEQ ID NOS: 17

<210> SEQ ID NO 1
<211> LENGTH: 4
<212> TYPE: PRT
<213> ORGANISM: Artificial sequence
<220> FEATURE:
<223> OTHER INFORMATION: Synthetic

<400> SEQUENCE: 1

Ala Ala Val Val
1

<210> SEQ ID NO 2
<211> LENGTH: 6
<212> TYPE: PRT
<213> ORGANISM: Artificial sequence
<220> FEATURE:
<223> OTHER INFORMATION: Synthetic

<400> SEQUENCE: 2

Ala Ala Ala Val Val Val
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic

<400> SEQUENCE: 3

Val Val Ala Ala Glu Glu Lys
1               5

<210> SEQ ID NO 4
<211> LENGTH: 25
<212> TYPE: DNA
<213> ORGANISM: Artificial sequence
<220> FEATURE:
<223> OTHER INFORMATION: Synthetic primer

<400> SEQUENCE: 4
tgaaggtcgg tgtgaacgga ttggc                                          25

<210> SEQ ID NO 5
<211> LENGTH: 24
<212> TYPE: DNA
<213> ORGANISM: Artificial sequence
<220> FEATURE:
<223> OTHER INFORMATION: Synthetic primer

<400> SEQUENCE: 5
catgtaggcc atgaggtcca ccac                                           24

<210> SEQ ID NO 6
<211> LENGTH: 22
<212> TYPE: DNA
<213> ORGANISM: Artificial sequence
<220> FEATURE:
<223> OTHER INFORMATION: Synthetic primer

<400> SEQUENCE: 6
gttgccaagc tgggaagaac ac                                             22

<210> SEQ ID NO 7

```
<211> LENGTH: 20
<212> TYPE: DNA
<213> ORGANISM: Artificial sequence
<220> FEATURE:
<223> OTHER INFORMATION: Synthetic primer

<400> SEQUENCE: 7
cccaccccgc tattccaaac                                               20

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
caagtcccac acagcagctt                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic primer

<400> SEQUENCE: 9
aaagccgagc tgccagagtt                                               20

<210> SEQ ID NO 10
<211> LENGTH: 13
<212> TYPE: PRT
<213> ORGANISM: Homo sapiens

<400> SEQUENCE: 10

Met Gln Ala Lys His Lys Gln Arg Lys Arg Leu Lys Ser
1               5                   10

<210> SEQ ID NO 11
<211> LENGTH: 9
<212> TYPE: PRT
<213> ORGANISM: Homo sapiens

<400> SEQUENCE: 11

Lys Lys Asn Lys Asn Cys Arg Arg His
1               5

<210> SEQ ID NO 12
<211> LENGTH: 14
<212> TYPE: PRT
<213> ORGANISM: Homo sapiens

<400> SEQUENCE: 12

Gly Lys Lys Gln Arg Leu Ser Lys Lys Leu Arg Arg Lys Leu
1               5                   10

<210> SEQ ID NO 13
<211> LENGTH: 8
<212> TYPE: PRT
<213> ORGANISM: Homo sapiens

<400> SEQUENCE: 13

Gly Lys Arg Arg His Pro Lys Lys
1               5
```

```
<210> SEQ ID NO 14
<211> LENGTH: 55
<212> TYPE: PRT
<213> ORGANISM: Homo sapiens

<400> SEQUENCE: 14

Ala Arg Gln Glu Asn Pro Cys Gly Pro Cys Ser Glu Arg Arg Lys His
1               5                   10                  15

Leu Phe Val Gln Asp Pro Gln Thr Cys Lys Cys Ser Cys Lys Asn Thr
            20                  25                  30

Asp Ser Arg Cys Lys Ala Arg Gln Leu Glu Leu Asn Glu Arg Thr Cys
        35                  40                  45

Arg Cys Asp Lys Pro Arg Arg
        50                  55

<210> SEQ ID NO 15
<211> LENGTH: 17
<212> TYPE: PRT
<213> ORGANISM: Homo sapiens

<400> SEQUENCE: 15

Lys Lys Asn Gly Ser Cys Lys Arg Gly Pro Arg Thr His Tyr Gly Gln
1               5                   10                  15

Lys

<210> SEQ ID NO 16
<211> LENGTH: 17
<212> TYPE: PRT
<213> ORGANISM: Homo sapiens

<400> SEQUENCE: 16

Arg Thr Gly Gln Tyr Lys Leu Gly Ser Lys Thr Gly Pro Gly Gln Lys
1               5                   10                  15

Ala

<210> SEQ ID NO 17
<211> LENGTH: 13
<212> TYPE: PRT
<213> ORGANISM: Homo sapiens

<400> SEQUENCE: 17

Met Ala Pro Thr Ser Ser Ser Thr Lys Lys Thr Gln Leu
1               5                   10
```

SUPRAMOLECULAR GLYCOSAMINOGLYCANS

CROSS REFERENCE TO RELATED APPLICATIONS

The present invention is a continuation of U.S. patent application Ser. No. 15/566,066, filed Oct. 12, 2017, now U.S. Pat. No. 10,792,327, claims priority to U.S. Provisional Patent Application 62/147,350, filed Apr. 14, 2015, each of which is incorporated by reference in its entirety.

STATEMENT REGARDING FEDERALLY SPONSORED RESEARCH OR DEVELOPMENT

This invention was made with government support under grant number DE015920 awarded by the National Institutes of Health. The government has certain rights in the invention.

FIELD

Provided herein are glycosylated peptide amphiphiles (GPAs), supramolecular glyconanostructures assembled therefrom, and methods of use thereof. In particular, provided herein are glycosaminoglycan (GAG) mimetic peptide amphiphiles (PAs) and supramolecular GAG mimetic nanostructures assembled therefrom that mimic the biological activities of GAGs, such as heparin, heparan sulfate, hyaluronic acid etc.

BACKGROUND

Glycosaminoglycans (GAGs) are heterogeneous polysaccharides ubiquitously found in mammalian tissues (ref. 1; incorporated by reference in its entirety). Heparan sulfate (HS) is a highly sulfated GAG with enormous structural diversity known to interact with a plethora of proteins to regulate many physiological processes (ref. 2; incorporated by reference in its entirety). In fact, more than 300 secreted or membrane bound proteins have been found to bind HS and their biological functions are associated with a broad range of phenomena including cell differentiation, morphogenesis and organogenesis during development, blood coagulation, lipid metabolism, inflammation, and response to injury, among many others. The proteins known to interact with HS include growth factors (GFs), chemokines, enzymes, enzyme inhibitors, extracellular matrix proteins, and membrane bound receptors. HS is known to potentiate key GFs responsible for cell proliferation and differentiation, including bone morphogenetic protein-2 (BMP-2) which is important in bone formation (ref. 3; incorporated by reference in its entirety), as well as vascular endothelial growth factor (VEGF) and fibroblast growth factor (FGF) which mediate the formation of blood vessels (ref. 2; incorporated by reference in its entirety).

The use of HS as a therapy to potentiate bioactivity of proteins has been hindered by its limited availability and its enormous chemical heterogeneity. The chemical heterogeneity of HS is put into perspective by the fact that a simple disaccharide in its sequence could have up to 48 possible structures (ref. 4; incorporated by reference in its entirety), and this biopolymer has molecular weights in the range of 20-100 kDa (ref. 2; incorporated by reference in its entirety). A close analog of HS is the biopolymer heparin with a more homogeneous structure than HS and lower molecular weights. Heparin can be easily isolated and is also known to potentiate some of the HS binding GFs (refs. 1, 3, 5; incorporated by reference in its entirety). However, heparin is a well-known anticoagulant in clinical use and this has been an obstacle to its broader application as a bioactive therapy. Hence, there is an unmet need for a new type of heparin and HS variant for the applications in regenerative medicine.

SUMMARY

Provided herein are glycosylated peptide amphiphiles (GPAs), supramolecular glyconanostructures assembled therefrom, and methods of use thereof. In particular, provided herein are glycosaminoglycan (GAG) mimetic peptide amphiphiles (PAs) and supramolecular GAG mimetic nanostructures assembled therefrom that mimic the biological activities of GAGs, such as heparin, heparan sulfate, hyaluronic acid etc. In some embodiments, GPAs are provided that self-assemble in aqueous conditions into high-aspect-ratio nanostructures presenting mono-, di-, or oligosaccharide units and mimic the activity of biologically-relevant polysaccharides.

In some embodiments, provided herein are supramolecular glyconanostuctures comprising a glycosylated peptide amphiphiles (GPAs) self-assembled into a nanofiber. In some embodiments, the supramolecular glyconanostuctures comprise a hydrophobic core, peptide surface, and saccharides displayed on the surface. In some embodiments, the GPAs comprise a hydrophobic non-peptide tail, a structured peptide segment, a charged peptide segment, and a terminal saccharide.

In some embodiments, supramolecular glyconanostucture further comprise filler peptide amphiphiles (PAs), wherein the filler PAs comprise a hydrophobic non-peptide tail, a structured peptide segment, and a charged peptide segment, but lack a terminal saccharide. In some embodiments, supramolecular glyconanostucture further comprise non-glycosylated bioactive PAs, wherein the non-glycosylated bioactive PAs comprise a hydrophobic non-peptide tail, a structured peptide segment, a charged peptide segment, and a non-saccharide bioactive terminal moiety.

In some embodiments, the saccharide of a supramolecular glyconanostucture is modified with a linker to facilitate conjugation to the peptide amphiphile. In some embodiments, the saccharide is selected from the group consisting of monosaccharide, disaccharide, and oligosaccharide. In some embodiments, the saccharide is selected from: (a) monosaccharides consisting of glucuronic acid (GlcA), N-acetylglucosamine (GlcNAc), N-sulfated glucosamine (GlcNS), glucosamine (GlcN), iduronic acid (IdoA), and sulfated versions thereof; (b) dissacharides of GlcA, GlcNAc, GlcNS, GlcN, IdoA, and sulfated versions thereof; (c) oligosaccharides of GlcA, GlcNAc, GlcNS, GlcN, IdoA, and sulfated versions thereof; (d) glycomimetics; and (e) sulfated fucoidan disaccharide and oligosaccharides. In some embodiments, the saccharide is a monosaccharide or disaccharide comprising a sulfated version of one of GlcA, GlcNAc, GlcNS, GlcN, or IdoA. In some embodiments, the saccharide is a monosaccharide of GlcNAc (3,4,6S).

In some embodiments, provided herein are supramolecular glycosaminoglycan (GAG) mimetics comprising the supramolecular glyconanostuctures, wherein the GPAs are GAG mimetic peptide amphiphiles (PAs). In some embodiments, supramolecular GAG mimetic exhibits a biological activity of heparin, heparin sulfate, and/or hyaluronic acid. In some embodiments, supramolecular GAG mimetics bind to one or more growth factors or a growth factor inhibitor.

In some embodiments, supramolecular GAG mimetics bind to a heparin binding domain of one or more of BMP-2, BMP-4, Noggin, VEGF, FGF-1, FGF-2, and sonic hedgehog (Shh).

In some embodiments, provided herein is synthetic extracellular matrix (sECM) comprising supramolecular GAG mimetics described herein. In some embodiments, the sECM comprises a composite of the supramolecular GAG mimetic and one or more additional nanostructures and/or polymers. In some embodiments, composites comprise non-glycosylated PA nanofibers. In some embodiments, the non-glycosylated PA nanofibers lack bioactive moieties. In some embodiments, the non-glycosylated PA nanofibers display non-saccharide bioactive moieties. In some embodiments, the non-glycosylated PA displays a "chemical handle" for chemical ligation. In some embodiments, composites comprise one or more polymers selected from the group consisting of collagen, chitosan, polyesters, alginate, fibrin, polyvinyl alcohol, carboxymethyl cellulose, hydroxypropyl cellulose, polyglycolic acid (PGA), polyamide, polyurethane, polylactic acid (PLA), poly(ethylene glycol) (PEG), poly(lactic acid-co-glycolic acid) (PLGA), poly-ε-caprolactone (PCL), poly(diol citrate), and combinations thereof. In some embodiments, composites comprise of synthetic or natural hydroxylapatite minerals. In some embodiments, the sECM further comprises one or more growth factors or other types of proteins. In some embodiments, one or more growth factors or other proteins are selected from the group consisting of BMP-2, BMP-4, Noggin, VEGF, FGF-1, FGF-2, and Shh.

In some embodiments, provided herein is a cell-growth or tissue-regeneration system comprising the sECM described herein and cells for growth thereon. In some embodiments, the cells are precursor or progenitor cells for a desired cell or tissue type.

In some embodiments, provided herein are methods of cell or tissue regeneration comprising administering the sECM or tissue regeneration systems described herein to a site in a subject comprising injured or diseased tissue in need of cell or tissue regeneration.

In some embodiments, compositions and methods within the scope herein are described in more detail in the Detailed Description.

BRIEF DESCRIPTION OF THE DRAWINGS

FIGS. 1A-D. Design of glycomimetic supramolecular assemblies. (A) Chemical structures of PAs that are functionalized with a series of monosaccharides (1-4), oligo (ethylene glycol) (5), or none (6). (B) Representative cryo-TEM image of filaments formed in 25 μM solutions of glycosylated PAs (scalebar: 200 nm). Also shown is a schematic representation of the glycosylated PA assembly. (C) In situ SAXS data showing the background subtracted scattered intensity versus the scattering vector q (log-log plot) for PAs 1-6 (6 mM) in saline. The data sets are offset vertically for clarity. (D) Zeta potential measurements of solutions of PAs 1-6 (1 mM) in saline.

FIGS. 6A-B. (A) Confocal images of PA 1 (top) or PA 4 (bottom) nanofibers which are co-assembled with fluorescently labeled PA (Cy3-PA) (left), after mixing with Cy5-labeled BMP-2 for 24 h (center). The merge images are also shown (right). (B) Confocal images of Cy5-labeled BMP-2, after mixing with non-fluorescent PA 1 (top) or PA 4 (bottom) nanofibers for 24 h.

FIGS. 17A-G. Glycopeptide nanofibers enhance bone formation. (A) In vitro anticoagulation activity of heparin and PA 1, evaluated by monitoring Factor Xa activity. (B—F) Evaluation of the glycopeptide nanofibers in a rat spinal fusion model. Each animal was treated with a sub-therapeutic dose of 100 ng BMP-2 with saline, PA 4 nano-fibers, or PA 1 nanofibers. (B) Fusion scores from blind manual palpation analysis at 8-week post-op (0=no fusion; 1=unilateral fusion; 2=bilateral fusion). (C) Fusion rates of each treatment, in which fusion scores ≥1 are considered solidly fused. (D-F) Representative volume renderings (blue background) from synchrotron micro-computed tomography. (F) Sagittal digital section through the fusion mass as indicated by the red dashed line on the volume rendering is shown on the right (black background).

DEFINITIONS

Figure 2A:
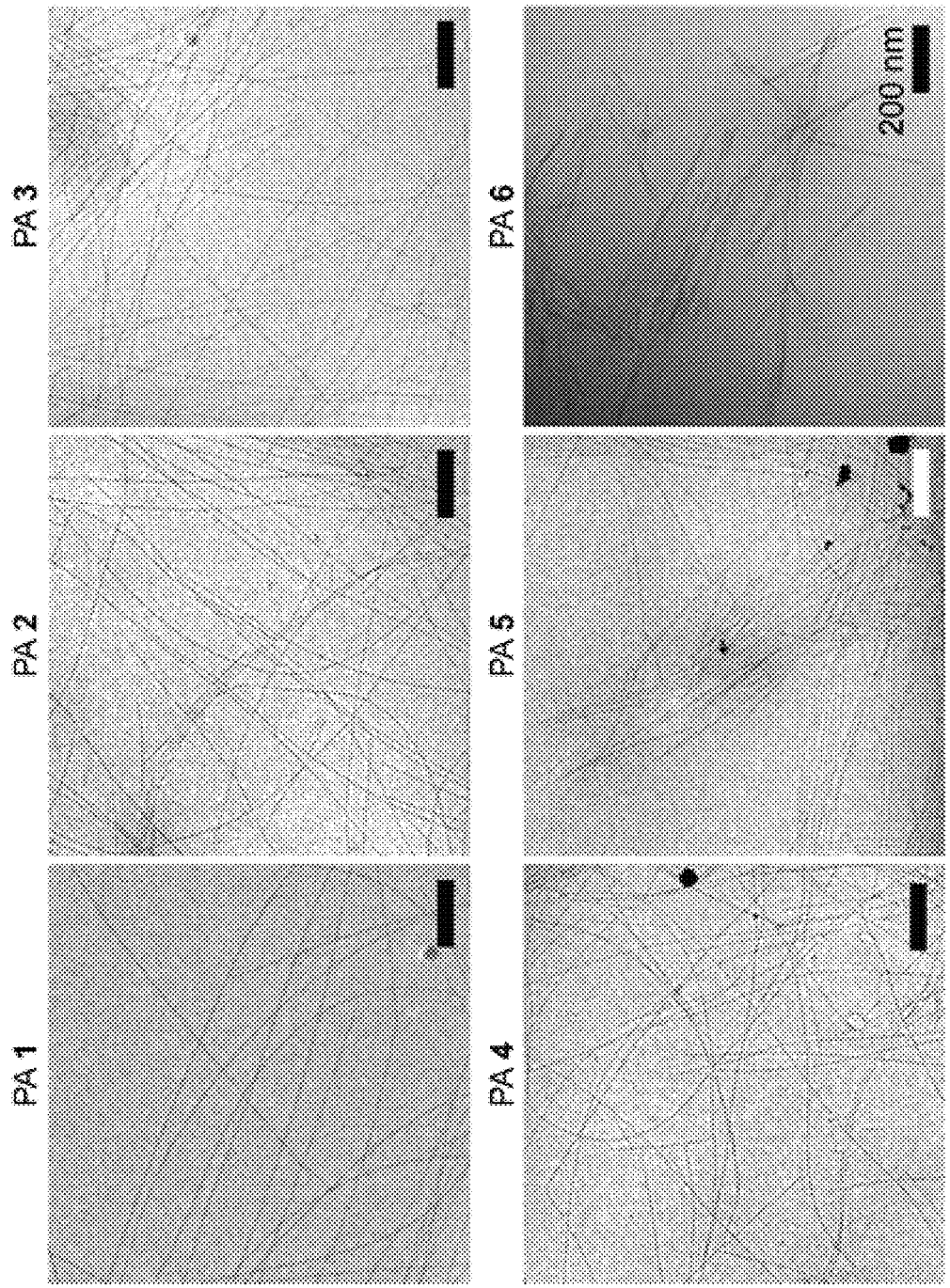
FIGS. 2A-B. (A) Representative cryo-TEM images of filaments of PAs 1-6 (25 μM) in saline with 2 mM $CaCl_2$) (scalebar: 200 nm). (B) Representative conventional TEM images of PA 1 and PA 4 nanofibers (200 nM) in SPR buffer (0.05% Tween-20) (scalebar: 500 nm).

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "saccharide" refers to the class of carbohydrates including "monosaccharides", "disaccharides" (i.e., two connected monosaccharide units), "oligosaccharides" (i.e., about 3-20 connected monosaccharide units), "polysaccharides" (i.e., over about 20 connected monosaccharide units), and "glycomimetics". Embodiments described herein as referring to "saccharides" may apply to any or all of mono-, di-, oligo-, and polysaccharides, and glycomimetics, all in their D and L stereoisomers, unless indicated otherwise.

As used herein, the term "glycosaminoglycan" refers to a class of complex polysaccharides having repeating units of mono- or di-saccharides. Non-limiting examples of glycosaminoglycans include dermatan surfate, hyaluronic acid, the chondroitin sulfates, chitin, heparin, heparin sulfate, keratan surfate, keratosulfate, and derivatives thereof.

As used herein, the term "mimetic" refers to a compound or complex which has substantially the same structural and/or functional characteristics as the reference molecule (e.g., binds to the protein). For example, "glycosaminoglycan mimetic" exhibits similar structural and/or functional (e.g., binds growth factors) features as glycosaminoglycans.

As used herein, the term "glycosylated" refers to a compound, polymer, complex, etc. having a carbohydrate residue such as a monosaccharide, disaccharide, oligosaccharide, polysaccharide, or a glycomimetic appended to the reference compound, polymer, complex, etc. For example, a "glycosylated peptide amphiphile" is a peptide amphiphile having a mono-, di-, oligo-, polysaccharide, or glycomimetic appended thereto.

As used herein, the term "glycomimetic" refers to molecular entities that exhibit structural and/or physical properties similar to carbohydrates and/or that exhibit similar or improved binding activity, biological activity, and/or stability.

As used herein, the term "fucodian" or "sulfated fucodian" refers to sulfated di-, oligo-, or polysaccharides that have a backbone built of (1→3)-linked α-1-fucopyranosyl or of alternating (1→3)- and (1→4)-linked α-1-fucopyranosyl residues, but also include sulfated galactofucans with backbones built of (1→6)-β-d-galacto- and/or (1→2)-β-d-mannopyranosyl units with fucose or fuco-oligosaccharide branching, and/or glucuronic acid, xylose or glucose substitutions. There are at least two distinct forms of fucoidan: F-fucoidan, which is >95% composed of sulfated esters of fucose, and U-fucoidan, which is approximately 20% glucuronic acid.

Carbohydrate mimetics include, but are not limited to, aza-sugars, c-glycosides, carbasugars, thiosugars, thioglycosides, sulfosugars, iminosugars, phospha sugars, glycosylamines, lactones, pseudo-sugars, aminocyclitols, cyclitols, polyols, inositols such as myo-inositol and scyllo-inositols.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, the term "peptoid" refers to a class of peptidomimetics where the side chains are functionalized on the nitrogen atom of the peptide backbone rather than to the α-carbon.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence "having at least Y % sequence identity with SEQ ID NO:Z" may have up to X substitutions relative to SEQ ID NO:Z, and may therefore also be expressed as "having X or fewer substitutions relative to SEQ ID NO:Z."

As used herein, the term "nanofiber" refers to an elongated or threadlike filament (e.g., having a significantly greater length dimension that width or diameter) with a diameter typically less than 100 nanometers.

As used herein, the term "supramolecular" (e.g., "supramolecular complex," "supramolecular interactions," "supramolecular fiber," "supramolecular polymer," etc.) refers to the non-covalent interactions between molecules (e.g., polymers, macromolecules, etc.) and the multicomponent assemblies, complexes, systems, and/or fibers that form as a result.

As used herein, the term "physiological conditions" refers to the range of conditions of temperature, pH and tonicity (or osmolality) normally encountered within tissues in the body of a living human.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and/or charged peptide segment (often both), and optionally a functional segment (e.g., linker segment, bioactive segment, etc.). The peptide amphiphile may express a net charge at physiological pH, either a net positive or negative net charge, or may be zwitterionic (i.e., carrying both positive and negative charges). Certain peptide amphiphiles consist of or comprise: (1) a hydrophobic, non-peptide segment (e.g., comprising an acyl group of six or more carbons), (2) a structural peptide segment (e.g., β-sheet forming); (3) a charged peptide segment, and (4) a functional segment (e.g., linker segment).

As used herein and in the appended claims, the term "lipophilic moiety" or "hydrophobic moiety" refers to the moiety (e.g., an acyl, ether, sulfonamide, or phosphodiestermoiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in the context of the embodiments described herein, the hydrophobic component preferably comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. However, other lipophilic groups may be used in place of the acyl chain such as steroids, phospholipids and fluorocarbons.

As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by circular dichroism (CD).

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

DETAILED DESCRIPTION

Provided herein are glycosylated peptide amphiphiles (GPAs), supramolecular glyconanostructures assembled therefrom, and methods of use thereof. In particular, provided herein are glycosaminoglycan (GAG) mimetic peptide amphiphiles (PAs) and supramolecular GAG mimetic nanostructures assembled therefrom that mimic the biological activities of GAGs, such as heparin, heparan sulfate, hyaluronic acid etc. In some embodiments, GPAs are provided that self-assemble in aqueous conditions into high-aspect-ratio nanostructures presenting mono-, di-, oligosaccharide, polysaccharides, or glycomimetic units.

As experiments conducted during development of embodiments herein demonstrate, self-assembled GPA nanostructures (e.g., nanofibers of highly-sulfated monosaccharide) exhibit strong binding affinities to, for example, heparin-binding growth factors. For example, highly-sulfated GPA nanostructures were found to interact with BMP-2 via its heparin-binding domain to enhance BMP-2 induced osteoblast differentiation in vitro. In addition, the GPAs exhibited minimal anticoagulant activity, a characteristic that makes the compositions described herein highly useful for tissue engineering and regenerative medicine.

In some embodiments, provided herein are supramolecular glycosaminoglycan mimetics (e.g., GPA nanostructures), in which synthetic monosaccharides are displayed on the surface of a nanoscale fiber. The internal structure of this nanofiber was built by self-assembly of peptide amphiphiles (PAs), which form supramolecular polymers that mimic extracellular matrix filaments (refs. 6, 7; incorporated by reference in their entireties).

In some embodiments, compositions herein comprise peptide amphiphiles. In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus of the peptide, in order to create the lipophilic segment. Synthesis typically starts from the C-terminus, to which amino acids are sequentially added using either a Rink amide resin (resulting in an —NH$_2$ group at the C-terminus of the peptide after cleavage from the resin), or a Wang resin (resulting in an —OH group at the C-terminus), or variants thereof. Accordingly, embodiments described herein encompasses peptide amphiphiles having a C-terminal moiety that may be selected from the group consisting of —H, —OH, —COOH, —CONH$_2$, and —NH$_2$.

In some embodiments, peptide amphiphiles comprise a hydrophobic (non-peptide) segment linked to a peptide. In some embodiments, the peptide comprises a structural segment (e.g., hydrogen-bond-forming segment, beta-sheet-forming segment, etc.), and a charged segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more functional groups (e.g., alkene, alkyne, azide, thiol, etc.) for the attachment of a mono-, di-, oligo-, or polysaccharide, or glycomimetic residue. In some embodiments, various segments may be connected by linker segments (e.g., peptide (e.g., GG) or non-peptide (e.g., alkyl, OEG, PEG, etc.) linkers).

The lipophilic or hydrophobic segment is typically incorporated at the N-terminus of the peptide after the last amino acid coupling, and is composed of a fatty acid or other acid that is linked to the N-terminal amino acid through an acyl bond (although embodiments herein are not limited to such methods). In aqueous solutions, PA molecules self-assemble (e.g., into cylindrical micelles (a.k.a nanofibers)) that bury the lipophilic segment in their core and display the functional peptide and/or saccharide on the surface. The structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between) is covalently coupled to peptide segment (e.g., a peptide comprising a segment having a preference for beta-strand conformations) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture. In various embodiments, hydrophobic segments pack in the center of the assembly with the peptide/saccharide segments exposed to an aqueous or hydrophilic environment to form cylindrical nanostructures that resemble filaments. Such nanofilaments display the peptide or saccharide regions on their exterior and have a hydrophobic core.

In some embodiments, to induce self-assembly of an aqueous solution of peptide amphiphiles, the pH of the solution may be changed (raised or lowered) or mono-/multivalent ions, such as sodium or calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30).

In some embodiments, PAs comprise one or more peptide segments. Peptide segment may comprise natural amino acids, modified amino acids, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises EE.

In some embodiments, peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural and/or beta-sheet-forming segment. In some embodiments, the structural segment is rich in H, I, L, F, V, and A residues. In some embodiments, the structural and/or beta-sheet-forming segment comprises an alanine- and valine-rich peptide segment (e.g., AAVV (SEQ ID NO: 1), AAAVVV (SEQ ID NO: 2), or other combinations of V and A residues, etc.). In some embodiments, the structural and/or beta sheet peptide comprises 4 or more consecutive A and/or V residues, or conservative or semi-conservative substitutions thereto. In some embodiments, the structural and/or beta-sheet forming peptide segment comprises 4 or more consecutive non-polar aliphatic residues (e.g., alanine (A), valine (V), leucine (L), isoleucine (I), methionine (M)). In some embodiments, the structural and/or beta-sheet forming peptide segment comprises 2-16 amino acids in length and comprises 4 or more (e.g., 2, 3, 4, 5, 6, 7, 8, 9, 10, 11, 12, 13, 14, 15, 16, or ranges there between) non-polar aliphatic residues.

In some embodiments, peptide amphiphiles comprise a non-peptide spacer or linker segment. In some embodiments, the non-peptide spacer or linker segment is located at the opposite terminus of the peptide from the hydrophobic segment. In some embodiments, the spacer or linker segment provides the attachment site for a functional group. In some embodiments, the spacer or linker segment provides a reactive group (e.g., alkene, alkyne, azide, thiol, maleimide etc.) for functionalization (e.g., glycosylation) of the PA. In some embodiments, the spacer or linker is a substantially linear chain of CH2, O, $(CH_2)_2O$, $O(CH_2)_2$, NH, and C=O groups (e.g., $CH2(O(CH_2)_2)_2NH$, $CH2(O(CH_2)_2)_2NHCO(CH_2)_2CCH$, etc.). In some embodiments, a spacer or linker further comprises additional functional groups, substituents, branches, etc.

Suitable peptide amphiphiles, PA segments, PA nanostructures, and associated reagents and methods are described, for example in U.S. Pat. Nos. 8,512,693; 8,450,271; 8,138,140; 8,124,583; 8,114,835; 8,114,834; 8,080,262; 8,063,014; 7,851,445; 7,838,491; 7,745,708; 7,683,025; 7,554,021; 7,544,661; 7,534,761; 7,491,690; 7,452,679; 7,390,526; 7,371,719; 6,890,654; herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural segment, functional segment, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a peptide amphiphile comprises: (a) a hydrophobic tail comprising an alkyl chain of 8-24 carbons; (b) a structural segment (e.g., comprising VVAA); and (c) a charged segment (e.g., comprising EE). In some embodiments, the peptide amphiphile further comprises an attachment segment (e.g., K) for attachment of a functional group (e.g., attachment of a spacer, glycosylation, etc.). An exemplary peptide amphiphile is PA 7 (e.g., $CH_3(CH_2)_{14}$-VVAAEEK-$COCH_2(O(CH_2)_2)_2NHCO(CH_2)_2CCH$) (SEQ ID NO: 3); although, in some embodiments, any PAs within the scope described herein, comprising the components described herein, or within the skill of one in the field, may find use herein.

In some embodiments, provided herein are glycosylated peptide amphiphiles and self-assembled nanostructures (e.g., nanofibers) thereof. Glycosylated PAs display a mono, di-, oligo-, or polysaccharide, or glycomimetic at one terminus (e.g., opposite terminus as the hydrophobic segment).

In some embodiments, the saccharide is a mono, di-, oligosaccharide, or glycomimetic that mimics the function of a particular polysaccharide in a biological context (e.g., protein binding (e.g., to the heparin binding site of growth factors, etc.), etc.). In some embodiments, the saccharide is a mono, di-, oligosaccharide that mimics a glycosaminoglycan.

In some embodiments, glycosylated peptide amphiphiles are provided displaying a monosaccharide (e.g., at the terminus opposite the hydrophobic tail). Suitable monosaccharides include 1,2-cis/1,2-trans glycosides (alfa/beta anomers) from pentoses, hexoses, heptoses, octoses, and nonoses in the form of pyranoses and furanoses in both L- and D-form. Exemplary monosaccharides for conjugation to PAs and nanostructures herein include, but are not limited to: (i) hexoses such as galactose, glucose, mannose, talose, (ii) hexosamines such as galactosamine, glucosamine, mannosamine, talosamine; (iii) hexosamine derivatives such as N-acetylation of galactosamine, glucosamine, mannosamine, talosamine, (iv) ulosonic- and uronic acids such as KDO (3-Deoxy-D-manno-oct-2-ulosonic acid), glucuronic acid and iduronic acids, (v) sialic acids such as neuraminic acid, N-acetylneuraminic acid and N-glycolylneuraminic acid; (vi) deoxy sugars such as rhamnose, fucose; (vii) pentoses such as arabinose, ribose, and xylose; (viii) heptoses such as L-glycero-D-mannoheptulose. Other suitable classes of glycomimetics for conjugation to the PAs herein include, but are not limited to: (i) aza-sugars, (ii) c-glycosides, (iii) carbasugars, (iv) thiosugars, (v) sulfosugars, (vi) thioglycosides, (vii) iminosugars, (viii) phospha sugars, (ix) glycosylamines, (x) lactones, (xi) pseudo-sugars, (xii) aminocyclitols, (xiii) cyclitols, (xiv) polyols, (xv) inositols such as myo-inositol and scyllo-inositols.

In some embodiments, the monosaccharides are functionalized to include one or more additional or alternative functional groups. For example, exemplary functionalizations of the monosaccharides and possible salts thereof include, but not limited to: (i) amino groups, (ii) acetamides, (iii) carboxymethylates, (iv) phosphates, (v) O-/N-sulfates, and (vi) bioisosteres such as sulfonamides, fluorine etc, and (vii) radiolabeling with for instance 18F or para-magnetic with 19F. The degree of sulfation per saccharide unit can vary from mono-sulfation, di-sulfation, tri-sulfation, and tetra-sulfation (e.g., with a defined functionalization pattern).

In some embodiments, PAs are conjugated with di-, oligo, or polysaccharides, or glycomimetics. The aforementioned monosacchardies may be combined in any suitable combinations to yield di-, oligo, or polysaccharides with different structures, bioactivities, and applications. Exemplary di-, oligo, or polysaccharides, or glycomimetics include, but not limited to: (i) disaccharides such as Hylauronic acid disaccharides (e.g., D-glucuronic acid and D-N-acetylglucosamine), heparin-/heparan sulfate disaccharides (e.g., GlcA-GlcNAc, GlcA-GlcNS, IdoA-GlcNS, IdoA(2S)-GlcNS, IdoA-GlcNS(6S), IdoA(2S)-GlcNS(6S), etc.), cellobiose, maltose, lactulose, chitobiose; (ii) oligosaccharides such as Sialyl Lewis$^x$, glycosylphosphatidylinositol (GPI-anchors), GAG-oligosaccharides, globotriose, sulfated GAG-oligosaccharides, fucoidan oligosaccharides, and sulfated fucoidan oligosaccharides; (iii) glycomimetics such as kanamycin, neomycin, streptomycin. In some embodiments, oligosaccharides or polysaccharides of Hylauronic acid disaccharides (e.g., D-glucuronic acid and D-N-acetylglucosamine), heparin-/heparan sulfate disaccharides (e.g., GlcA-GlcNAc, GlcA-GlcNS, IdoA-GlcNS, IdoA(2S)-GlcNS, IdoA-GlcNS(6S), IdoA(2S)-GlcNS(6S), etc.) are provided.

In some embodiments, in addition to the core saccharide structure, the saccharides for conjugation to a PA further comprise a linker, attachment moiety, or reactive functional group. In some embodiments, the saccharide is attached to a spacer or linker segment on the peptide amphiphile. In some embodiments, the spacer or linker segment displays a functional group that will react to form a covalent bond with a functional group on the saccharide (or a compound comprising the saccharide (and a linker)). Linkers and suitable reaction chemistries are described herein. Exemplary pairs of functional groups for attaching the saccharide to the PA are alkyne/azide, thiol/maleimide, thiol/haloacetyl (e.g., iodoacetyl, etc.), azide/phosphine (Staudinger ligation), thiol/pyridyl disulfide (e.g. pyridyldithiol, etc.), sulphonyl azides/thio acids, transcyclooctene and tetrazine groups, dibenzocyclooctyne and azide groups, etc. In some embodiments, the saccharide (or compound comprising the saccharide) and the PA each display one of a reactive pair of functional groups capable of undergoing a Huisgen cycloaddition or alkene hydrothiolation.

For example monosaccharide 1 and monosaccharide 2 comprise glycopyranoside core while displaying (among other modifications) an azidoethyl group at the anomeric position. The azide group provides for conjugation of the saccharide to a terminal alkyne on the PA. Any other suitable conjugation chemistries, and functionalization of saccharides to facilitate such chemistries, described herein or otherwise understood in the field will find use in embodiments herein.

In some embodiments, an appropriate saccharide, in terms of both identity and length, is selected for a particular target and/or application. Exemplary targets/applications of glycosylated PAs and supramolecular glyconanostructures include: (i) the use of fluorodeoxyglucose (FGD) in a glycoconjugated supramolecular fashion to increase the contrast and/or target specificity for positron emission tomography (PET); (ii) the supramolecular nanostructures conjugated to specific antigens as an efficient platform for the development of antibodies against bacterial strains (e.g., E. Coli), (iii) to combine the anti-inflammatory and/or anti-viral behavior of sulfated fucoidans with the peptide, (iv) GAG mimetics (e.g., mono-, di-, or oligosaccharides) that potentiate growth factors, for example, for regenerative medicine purposes, and (v) the use of conjugated glycomimetic to for antibiotic uses.

In some embodiments, provided herein are glycosylated peptide amphiphiles (e.g., GAG mimetic PAs) comprising any combination of peptide amphiphile elements (e.g., the hydrophobic segments, structural segments, charged segments, linkers, spacers, and functional groups described herein, incorporated by reference, or understood in the field), saccharides, linkers, and connection chemistries (e.g., alkyne/azide, etc.).

In some embodiments, the GPA is a GAG mimetic PA. A GAG mimetic PA is a peptide amphiphile that is conjugated to a mono-, di-, oligo-, or polysaccharide, or glycomimetic and is capable of exerting a bioactivity (e.g., growth factor binding) of a glycosaminoglycan (e.g., hyaluronic acid, heparin, heparin sulfate, etc.) in a relevant context (e.g., in vitro, in vivo, in a subject (e.g., at the site of injured or diseased tissue), etc.). In some embodiments, a GAG mimetic displays a saccharide (e.g., monosaccharide, disaccharide, oligosaccharide, etc.) that is found in natural GAGs (e.g., monosaccharides such as GlcA, GlcNAc, GlcNS, IdoA, IdoA (2S), GlcNS (6S), GlcNAc (3,4,6S), etc., and disaccharides/oligosaccharides combining such monosaccharides).

In some embodiments, GPAs, like the PAs they comprise and/or are formed from, self-assemble (e.g., in aqueous conditions, under known conditions, etc.) into supramolecular nanostructures (e.g., nanofibers) referred to herein as supramolecular glyconanostructures (or, for example, supramolecular glyconanofibers). In some embodiments, supramolecular glyconanostructures comprise a hydrophobic core and structured (e.g., supported by hydrogen bonding and/or beta-sheet structure) and charged peptide exterior, and display glycosylated features on the exterior. In some embodiments, the glycosylated terminus of the PAs are displayed on the exterior of the nanostructures.

In some embodiments, nanostructures are assembled from GPAs and filler peptide amphiphiles (e.g., non-glycosylated PAs, PAs not-labeled not displaying a bioactive moiety, etc.). In some embodiments, nanostructures (e.g., nanofibers) comprise: (i) less than 50% (e.g., 49%, 45%, 40%, 35%, 30%, 25%, 20%, 15%, 10%, 5%, 4%, 3%, 2%, 1%, or any ranges there between) GPAs; and/or (ii) less than 50% (e.g., 49%, 45%, 40%, 35%, 30%, 25%, 20%, 15%, 10%, 5%, 4%, 3%, 2%, 1%, or any ranges there between) bioactive peptide amphiphiles. Some embodiments, nanostructures (e.g., nanofibers) comprise and at least 2% (e.g., 2%, 3%, 4%, 5%, 10%, 15%, 20%, 25%, 30%, 35%, 40%, 45%, 50%, 55%, 60%, 65%, 70%, 75%, 80%, 85%, 90%, 95%, 98%, or any ranges there between) filler peptide amphiphiles. In some embodiments, nanofibers comprise at least 50% (e.g., 50%, 55%, 60%, 65%, 70%, 75%, 80%, 85%, 90%, 95%, 98%, or any ranges there between) filler peptide amphiphiles. In some embodiments, the ratio of GPAs to filler PAs determines the density of saccharides displayed on the nanostructure surface. In some embodiments, supramolecular glyconanostructures are assembled from PAs comprising (e.g., in addition to filler PAs) GAG mimetic PAs. Such supramolecular glyconanostructures are referred to herein as "supramolecular GAG mimetics" or "supramolecular GAG mimetic nanostructures." In some embodiments, supramolecular GAG mimetics comprise a hydrophobic core and structured (e.g., supported by hydrogen bonding and/or beta-sheet structure) and charged peptide exterior, and display saccharides on their exterior that are capable of mimicking one or more bioactivities of a GAG (e.g., binding to a heparin binding domain of growth factors, etc.).

In some embodiments, glycosylated PAs (e.g., supramolecular GAG mimetics) are provided that have a high binding affinity for a protein of interest (e.g., a growth factor) and/or a specific binding domain of a protein of interest (e.g., the heparin-binding domain). In some embodiments, glycosylated PAs (e.g., supramolecular GAG mimetics) are provided having binding affinity for the heparin binding domain of various proteins (e.g., BMP-2, BMP-4, Noggin, VEGF, FGF-1, FGF-2, Shh, etc.). The binding affinity ($K_d$) may be chosen from one of: less than 10 μM, less than 1 μM, less than 100 nM, less than 10 nM, less than 1 nM, less than 100 μM.

In some embodiments, the glycosylated PAs (e.g., supramolecular GAG mimetics, etc.) described herein and nanostructures self-assembled therefrom are used in the repair or regeneration of bodily tissue (e.g., soft tissue), bone regeneration, neural regeneration, skeletal tissue construction, repair of muscle injuries, the repair of cardio-vascular injuries, the expansion and self-renewal of embryonic- and adult stem cells, etc. In some embodiments, the scope is not limited by the identity of the particular cells/tissues/systems in which the compositions and methods herein find use. Accordingly, compositions described herein may be used to prevent or treat a wide range of diseases and injuries, including: soft tissue wound repair, post-surgical healing, osteoarthritis, cartilage replacement, broken bones of any kind (e.g. spinal disc fusion treatments, long bone breaks, cranial defects, etc.), critical or non-union bone defect regeneration, etc.

The use of glycosylated PAs (e.g., supramolecular GAG mimetics, etc.) and nanostructures self-assembled therefrom in the repair, regeneration or replacement of tissue may involve use in wound healing, e.g. acceleration of wound healing, healing of scar or bone tissue and tissue grafting.

In some embodiments, provided herein is synthetic extracellular matrix (sECM) comprising supramolecular assemblies (e.g., nanofibers) of glycosylated PAs (e.g., GAG mimetics, etc.). In some embodiments, sECM comprises glycosylated PAs (e.g., GAG mimetics, etc.) and non-glycosylated PAs (e.g., unfunctionalized PAs (e.g., structural PAs), PAs functionalized with a non-saccharide agent). In some embodiments, sECM comprises PA nanofibers comprising GAG mimetic PAs. In some embodiments, GAG mimetic PAs of the sECM recruit, localize, bind, etc. growth factors that facilitate cell differentiation, tissue regeneration, bone formation, etc. In some embodiments, deploying sECM comprising GAG mimetic PAs to the site of an injury or disease in a subject facilitates regeneration of healthy tissue/cells at that location. In some embodiments, the sECM recruits growth factors (GFs) from within the subject (e.g., endogenous GFs) and localizes the GFs to the treatment location. In some embodiments, the sECM is doped with exogenous GFs (e.g., BMP-2, BMP-4, Noggin, VEGF, FGF-1, FGF-2, Shh, etc.) and the sECM and GFs are deployed/implanted within the subject. In some embodiments, sECM is doped with GFs that are specific to the desired treatment outcome (e.g., cell differentiation, bone formation, soft tissue regeneration, etc.). In some embodiments, sECM is further supplied with additional agents to facilitate the desired outcomes. Such additional agents may include: stem cells, cell differentiation factors (e.g., OCT4, SOX2, etc.), cytokines/chemokines, antibodies, pharmaceutical agents (e.g., antibiotics, etc.), etc.

In another aspect, provided herein are biological scaffolds comprising glycosylated PAs (e.g., supramolecular GAG mimetics, etc.). In some embodiments, the biological scaffolds may be used in orthopedic, vascular, prosthetic, skin and corneal applications. The biological scaffolds include extended-release drug delivery devices, catheters, tissue valves, tissue valve leaflets, drug-eluting stents, vascular grafts, wound healing or skin grafts and orthopedic prostheses such as bone, ligament, tendon, cartilage and muscle. In some embodiments, the biological scaffold comprises one or more glycosylated PAs (e.g., GAG mimetic PAs, etc.) and/or nanostructures self-assembled therefrom attached to a surface thereof.

In some embodiments, a pharmaceutical or medical composition or medicament comprising glycosylated PAs (e.g., GAG mimetic PA, etc.) or nanostructures self-assembled therefrom is provided, optionally in combination with a pharmaceutically acceptable carrier, adjuvant or diluent. In some embodiments pharmaceutical compositions or medicaments may further comprise other agents useful in regenerative medicine. Pharmaceutical compositions or medicaments comprising are provided for use in, for example, the prevention or treatment of injury or disease, tissue regeneration, etc. The use of glycosylated PAs (e.g., supramolecular GAG mimetics, etc.) in the manufacture of a medicament for the prevention or treatment of injury or disease, tissue regeneration, etc. is also provided. In some embodiments, a pharmaceutical composition comprises supramolecular assemblies (e.g., nanoparticles, nanofibers, etc.) of glycosylated PAs (e.g., GAG mimetic PAs). In some embodiments, the pharmaceutical composition further comprises additional therapeutic agents. In some embodiments, the pharmaceutical composition is administered locally to a treatment site (e.g., location of wound or diseased tissue, bone, cells, etc.). In some embodiments, the pharmaceutical composition is administered systemically.

In some embodiments, the glycosylated PAs (e.g., GAG mimetic PA, etc.) described herein and/or nanostructures self-assembled therefrom are useful in a range of applications, in vitro and/or in vivo, for example, stimulation of cell (e.g., mesenchymal stem cells, induced pluripotent cells, etc.) or tissue growth and/or proliferation and/or differentiation either in cell or tissue culture in vitro, or in cells or tissue in vivo.

In some embodiments, a method of preventing or treating injury or disease, tissue regeneration, etc. in a subject in need of such treatment is provided, the method comprising administering an effective amount of or nanostructures self-assembled therefrom to the subject. The administered supramolecular glyconanostructures (e.g., supramolecular GAG mimetics) may be formulated in a suitable pharmaceutical composition or medicament and may further comprise a pharmaceutically acceptable carrier, adjuvant or diluent.

In some embodiments, methods are useful for promoting osteogenesis (the formation of bone cells and/or bone tissue), for example, by administering supramolecular glyconanostructures (e.g., supramolecular GAG mimetics) to bone precursor cells or bone stem cells.

In some embodiments, methods are useful for promoting the formation of cartilage tissue (chondrogenesis), for example, by administering glycosylated PAs (e.g., GAG mimetic PA, etc.) described herein and/or nanostructures self-assembled therefrom to cartilage precursor cells or cartilage stem cells.

In some embodiments, methods are useful for promoting the formation of soft tissues (e.g., tendons, ligaments, fascia, skin, fibrous tissues, fat, synovial membranes, muscles, nerves, blood vessels, etc.), for example, by administering glycosylated PAs (e.g., GAG mimetic PA, etc.) described herein and/or nanostructures self-assembled therefrom to precursor cells or progenitor cells (e.g., stem cells) for the desired soft tissue.

In some embodiments, methods are useful for promoting the formation of tissues (e.g., soft tissues, connective tissues, etc.) such as bone, cartilage, muscle, fat, ligament or tendon. The prevention or treatment of disease using the PAs and supramolecular nanostructures herein may involve the repair, regeneration or replacement of tissue, particularly soft or connective tissue such as bone, cartilage, muscle, fat, ligament or tendon. In subjects having a deterioration of one of these tissues (e.g., due to disease or injury), administration of glycosylated PAs (e.g., GAG mimetic PA, etc.) described herein and/or nanostructures self-assembled therefrom to the site of deterioration may be used to stimulate the growth, proliferation and/or differentiation of tissue at that site. For example, stimulation of mesenchymal stem cells present at, or near to, the site of administration may lead to the proliferation and differentiation of the mesenchymal stem cells into the appropriate tissue, thereby providing for replacement/regeneration of the damaged tissue and treatment of the injury.

Alternatively, cells or tissue obtained from culture (e.g., of mesenchymal stem cells, of soft tissue cells or precursor cells, etc.) in contact with glycosylated PAs (e.g., GAG mimetics) or nanostructures thereof is collected and implanted at the site of injury or disease to replace damaged or deteriorated tissue. The damaged or deteriorated tissue may optionally first be excised from the site of injury or disease. A method of implantation of cells and/or tissues is provided comprising the steps of: (a) culturing cells and/or tissues in vitro in contact with the glycosylated PAs (e.g., GAG mimetics) or nanostructures thereof; (b) collecting the cells and/or tissues; and (c) implanting the cells and/or tissues into a human or animal subject in need of treatment (e.g., at a site in need of tissue regeneration). In some embodiments, the cells/tissues are cultured in part in contact with supramolecular GAGs (e.g., glycosylated PAs) for a period of time sufficient to allow growth, proliferation or differentiation of the cells or tissues. For example, the period of time may be chosen from: at least 5 days, at least 10 days, at least 20 days, at least 30 days or at least 40 days. In some embodiments, the cells/tissues are grown in a matrix comprising the nanostructures (e.g., nanofibers described herein).

In some embodiments, a composition is provided containing stem cells (e.g., mesenchymal stem cells), and glycosylated PAs (e.g., GAG mimetic PAs) or supramolecular nanostructures (e.g., glyconanostructures, GAG mimetics, etc.). Administration, e.g. injection, of the composition at the site of injury, disease or deterioration provides for the regeneration of tissue at the site. In some embodiments, a composite of glycosylated PAs and a supporting matrix such as collagen (in all of its forms) administrated locally at the site of injury, disease or deterioration provides for the regeneration of tissue at the site.

EXPERIMENTAL

Example 1

Synthesis

2-Azidoethyl 2-acetamido-3,4,6-tri-O-sulfo-2-de-oxy-β-D-glycopyranoside (monosaccharide I)

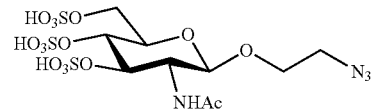

To a solution of 2-Azidoethyl 2-acetamido-2-deoxy-β-D-glucopyranoside (34) (1.00 g, 3.45 mmol) in dry DMF (60.0 mL) Me$_3$NSO$_3$ (7.19 g, 51.7 mmol) was added and stirred overnight at 50° C. MeOH (10.0 mL) was added and the reaction mixture was stirred for 1 h at room temperature when the solution was evaporated and co-concentrated. FC (MeCN/H$_2$O/NH$_3$ 6:1:0.5) gave title compound monosaccharide 1 (1.62 g, 3.05 mmol, 89%) as a colorless solid. $R_f$=0.36 (MeCN/H$_2$O/NH$_3$ 6:1:0.5); ATR-IR $v_{max}$cm$^{-1}$: 3197 (strong, broad), 3070 (strong, broad), 2110 (medium) 1633 (medium), 1565 (medium), 1423 (strong), 1161 (strong), 1039 (strong), 793 (strong); $^{13}$C-NMR (100 MHz, D$_2$O): δ=22.3 (CH$_3$), 50.3 (OCH$_2$CH$_2$N), 54.4 (C-5), 67.5 (C-6), 69.2 (OCH$_2$CH$_2$N), 72.5 (C-2), 74.4 (C-4), 78.3 (C-3), 100.4 (C-1), 174.7 (CH$_3$CO); $^1$H-NMR (500 MHz, D$_2$O): δ=2.01 (s, 3H, CH$_3$), 3.46 (1H, ddd, J=3.0, 5.6, 13.8 Hz, OCH$_2$CH$_2$N), 3.57 (ddd, 1H, J=3.0, 7.8, 13.8 Hz, OCH$_2$CH$_2$N), 3.87 (ddd, 1H, J=3.0, 7.8, 11.4 Hz, OCH$_2$CH$_2$N), 3.97-4.02 (m, 2H, H-2, H-5), 4.12 (ddd, 1H, J=3.0, 5.6, 11.4 Hz, OCH$_2$CH$_2$N), 4.19 (dd, 1H, J=7.8, 11.5 Hz, H-6a), 4.31 (dd, 1H, J=8.9, 9.7 Hz, H-4), 4.56 (dd, 1H, J=8.9, 10.2 Hz, H-3), 4.64 (d, 1H, J=2.3, 11.5 Hz, H-6b), 4.79 (d, 1H, J=8.1 Hz, H-1); HRMS-ESI [M−H]: calcd for C$_{10}$H$_{18}$N$_4$O$_{15}$S$_3$, 528.9853; found, 528.9850.

2-Azidoethyl 2-acetamido-6-O-sulfo-2-deoxy-β-D-glucopyranoside (monosaccharide 2)

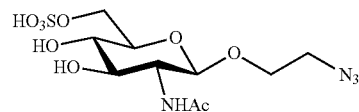

2-Azidoethyl 2-acetamido-2-deoxy-β-D-glucopyranoside (34) (0.50 g, 1.72 mmol) was dissolved in dry DMF (20.0 mL) whereupon Me$_3$NSO$_3$ (1.20 g, 8.61 mmol) was added and the solution was stirred at 50° C. After 2 h, the solution quenched with MeOH (10.0 mL) and solution was stirred at room temperature for 1 h when the mixture was evaporated and co-concentrated. FC (MeCN/H$_2$O/NH$_3$ 6:1:0.5) gave title compound monosaccharide 2 (0.53 g, 1.42 mmol, 83%) as a colorless solid. $R_f$=0.49 (MeCN/H$_2$O/NH$_3$ 6:1:0.5); ATR-IR $v_{max}$cm$^{-1}$: 3189 (strong, broad), 3095 (strong, broad), 2107 (strong), 1633 (medium), 1560 (medium), 1430 (strong), 1197 (strong), 1056 (medium), 991 (strong), 759 (strong); $^{13}$C-NMR (100 MHz, D$_2$O): δ=22.3 (CH$_3$CO), 50.3 (OCH$_2$CH$_2$N), 55.4 (C-2), 67.0 (C-6), 68.9 (OCH$_2$CH$_2$N), 69.9 (C-4), 73.0 (C-5, C-3), 101.1 (C-1), 174.6

(CH₃CO); ¹H-NMR (500 MHz, D₂O): δ 2.11 (s, 3H, C$\underline{H}_3$), 3.49 (ddd, 1H, J=3.0, 5.5, 13.7 Hz, OCH₂C$\underline{H}_2$N), 3.53-3.57 (m, 1H, OCH₂C$\underline{H}_2$N), 3.59 (at, 1H, J=9.3 Hz, H-4), 3.64 (at, 1H, J=9.4 Hz, H-3), 3.75 (m, 1H, H-5), 3.79-3.87 (m, 2H, H-2, OC$\underline{H}_2$CH₂N, overlap with residual MeOSO₃H), 4.11 (ddd, 1H, J=3.0, 5.5, 11.4, Hz, OC$\underline{H}_2$CH₂N), 4.31 (add, 1H, J=5.2, 11.2 Hz, H-6b), 4.42 (add, 1H, J=1.9, 11.2 Hz, H-6a), 4.68 (d, 1H, J=8.5 Hz, H-1); HRMS-ESI [M+H]: calcd for C₁₀H₁₈N₄O₉S, 371.0873; found, 371.0866.

3,4,6S-GlcNAc PA (PA 1)

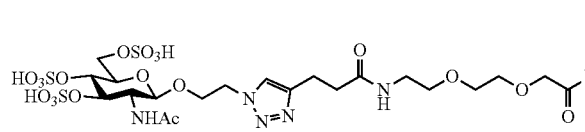

PA 1 was prepared by conjugating Alkyne PA and monosaccharide 1 using general procedure for Click-reaction. ATR-IR $v_{max}$cm⁻¹: 3277 (strong, broad), 2919 (medium), 2850 (weak), 1627 (strong), 1543 (strong), 1399 (medium), 1227 (strong), 1020 (medium), 987 (weak); ¹³C-NMR (125 MHz, DMF-d₇): δ 13.7 (Pal-CH₃), 16.2 (Ala-$\underline{C}_{(\beta)}$H₃), 17.6 (Ala-$\underline{C}_{(\beta)}$H₃), 18.0 (2×Val-$\underline{C}_{(\gamma)}$H₃), 19.1 (Val-$\underline{C}_{(\beta)}$H₃), 19.3 (Val-$\underline{C}_{(\beta)}$H₃), 21.8 (triazolyl-$\underline{C}_{(\alpha)}$H₂), 22.5 (several Pal-CH₂), 22.6 (acetyl-C$\underline{H}_3$), 23.7 (Lys-$\underline{C}_{(\delta)}$H₂), 25.9 (Pal-$\underline{C}$H₂), 26.8 (Lys-$\underline{C}_{(\beta)}$H₂), 27.5 (Glu-$\underline{C}_{(\beta)}$H₂), 29.2 (Pal-$\underline{C}$H₂, overlaps with solvent peak), 29.2-29.9 (several Pal-$\underline{C}$H₂, overlaps with solvent peak), 30.5 (Val-$\underline{C}_{(\gamma)}$H), 30.5 (Val-$\underline{C}_{(\gamma)}$H), 30.9 (Glu-$\underline{C}_{(\gamma)}$H₂), 30.9 (Glu-$\underline{C}_{(\beta)}$H₂), 31.8 (several Pal-$\underline{C}$H₂), 34.2-35.8 (Glu-$\underline{C}_{(\gamma)}$H₂, Lys-$\underline{C}_{(\gamma)}$H₂, Pal-$\underline{C}_{(\alpha)}$H₂, overlaps with solvent peak), 35.2 (triazolyl-$\underline{C}_{(\beta)}$H₂), 38.5 (Lys-$\underline{C}_{(\epsilon)}$H₂), 38.8 (OEG-$\underline{C}$H₂), 48.7 (Ala-$\underline{C}_{(\alpha)}$H), 49.8 (OCH₂$\underline{C}$H₂N), 50.8 (Ala-$\underline{C}_{(\alpha)}$H), 52.9 (Glu-$\underline{C}_{(\alpha)}$H), 53.6 (Glu-$\underline{C}_{(\alpha)}$H), 55.4 (C-2), 56.7 (Lys-$\underline{C}_{(\alpha)}$H), 58.5 (Val-$\underline{C}_{(\alpha)}$H), 58.7 (Val-$\underline{C}_{(\alpha)}$H), 67.6 (C-6), 67.6 (O$\underline{C}$H₂CH₂N), 69.4 (OEG-$\underline{C}$H₂), 69.8 (OEG-$\underline{C}$H₂), 70.3 (OEG-$\underline{C}_{(\alpha)}$H₂), 70.6 (OEG-$\underline{C}$H₂), 73.4 (C-4), 75.1 (C-5), 75.5 (C-3), 100.9 (C-1), 123.5 (triazolyl-$\underline{C}$CH), 146.3 (triazolyl-$\underline{C}$H), 170.0 ($\underline{C}$O), 170.6 ($\underline{C}$O), 171.3 ($\underline{C}$O), 172.1 ($\underline{C}$O), 172.5 ($\underline{C}$O), 172.7 ($\underline{C}$O), 173.5 ($\underline{C}$O), 173.8 ($\underline{C}$O), 173.9 ($\underline{C}$O), 175.0 ($\underline{C}$O), 175.0 ($\underline{C}$O), 178.0 ($\underline{C}$O), 178.0 ($\underline{C}$O); ¹H-NMR (600 MHz, DMF-d₇): δ 0.86 (t, 3H, J=6.4 Hz, Pal-C$\underline{H}_3$), 0.90 (at, 12H, J=6.9 Hz, Val-$\underline{C}_{(\gamma)}\underline{H}_3$), 1.22-1.30 (m, 20H, Pal-C$\underline{H}_2$), 1.31-1.36 (m, 2H, Pal-C$\underline{H}_2$), 1.38 (d, 3H, J=7.2 Hz, Ala-$\underline{C}_{(\beta)}\underline{H}_3$), 1.43 (d, 3H, J=7.3 Hz, Ala-$\underline{C}_{(\beta)}\underline{H}_3$), 1.48-1.59 (m, 6H, Lys-$\underline{C}_{(\delta)}$H₂, Pal-C$\underline{H}_2$), 1.77-1.84 (m, 2H, Glu-$\underline{C}_{(\beta)}$H₂), 1.89 (s, 3H, acetyl-C$\underline{H}_3$), 1.89-1.92 (m, 2H, Glu-$\underline{C}_{(\gamma)}$H₂), 1.95-1.95 (m, 2H, Lys-$\underline{C}_{(\beta)}$H₂), 2.10-2.16 (m, 4H, Glu-$\underline{C}_{(\beta)}$H₂, Val-$\underline{C}_{(\beta)}$H, Val-$\underline{C}_{(\beta)}$H), 2.19-2.36 (m, 6H, Glu-$\underline{C}_{(\gamma)}$H₂, Lys-$\underline{C}_{(\gamma)}$H₂, Pal-$\underline{C}_{(\alpha)}$H₂), 2.60 (t, 2H, J=7.9 Hz, triazolyl-$\underline{C}_{(\beta)}$H₂), 2.93-2.96 (m, 2H, triazolyl-$\underline{C}_{(\alpha)}$H₂), 3.17-3.23 (m, 2H, Lys-$\underline{C}_{(\epsilon)}$H₂), 3.33 (t, 2H, J=6.0 Hz, OEG-C$\underline{H}_2$), 3.50 (t, 2H, J=6.0 Hz, OEG-C$\underline{H}_2$), 3.60-3.62 (m, 2H, OEG-C$\underline{H}_2$), 3.64-3.65 (m, 2H, OEG-C$\underline{H}_2$), 3.85-3.90 (m, 1H, H6b, overlaps with H₂O), 3.92-3.95 (m, 1H, Lys-$\underline{C}_{(\alpha)}$H, overlaps with H₂O), 3.96 (s, 2H, OEG-$\underline{C}_{(\alpha)}$H₂), 4.05-4.10 (m, 3H, H-2, H-5, Glu-$\underline{C}_{(\alpha)}$H), 4.15-4.22 (m, 4H, OC$\underline{H}_2$CH₂N, Ala-$\underline{C}_{(\alpha)}$H, Glu-$\underline{C}_{(\alpha)}$H), 4.30-4.34 (m, 3H, H-3, 2×Val-$\underline{C}_{(\alpha)}$H), 4.44 (dd, 1H, J=2.6, 11.1 Hz, H6a), 4.51-4.55 (m, 2H, H-3, Ala-$\underline{C}_{(\alpha)}$H), 4.60-4.65 (m, 3H, H-1, OCH₂C$\underline{H}_2$N), 8.01 (s, 1H, triazole-C$\underline{H}$); HRMS-ESI [M−2H]/2: calcd for C₆₉H₁₂₀N₁₄O₃₁S₃, 867.3625; found 867.3623; [Cu]: 6.00 ng/mg.

6S-GlcNAc PA (PA 2)

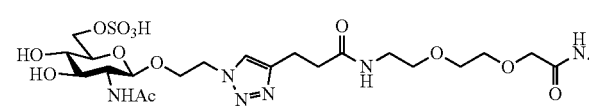

PA 2 was prepared by conjugating Alkyne PA and monosaccharide 2 using general procedure for Click-reaction. ATR-IR $v_{max}$cm⁻¹: 3276 (strong, broad), 2919 (medium), 2850 (weak), 1628 (strong), 1544 (weak), 1398 (medium), 1225 (strong), 1061 (medium), 1006 (medium); ¹³C-NMR (125 MHz, DMF-d₇): δ 13.7 (Pal-$\underline{C}$H₃), 16.7 (Ala-$\underline{C}_{(\beta)}$H₃), 16.8 (Ala-$\underline{C}_{(\beta)}$H₃), 18.2 (Val-$\underline{C}_{(\gamma)}$H₃), 18.2 (Val-$\underline{C}_{(\gamma)}$H₃), 19.0 (Val-$\underline{C}_{(\gamma)}$H₃), 19.0 (Val-$\underline{C}_{(\gamma)}$H₃), 21.7 (triazolyl-$\underline{C}_{(\alpha)}$H₂), 22.5 (several Pal-$\underline{C}$H₂), 22.5 (acetyl-$\underline{C}$H₃), 23.3 (Pal-$\underline{C}$H₂), 25.1 (Pal-$\underline{C}$H₂), 26.7 (Glu-$\underline{C}_{(\beta)}$H₂) 26.9 (Lys-$\underline{C}_{(\gamma)}$H₂), 29.1 (Lys-$\underline{C}_{(\delta)}$H₂), 29.1-29.8 (several Pal-$\underline{C}$H₂, overlap with solvent peak), 30.0 (Val-$\underline{C}_{(\beta)}$H), 30.0 (Val-$\underline{C}_{(\beta)}$H), 30.8 ($\underline{C}_{(\gamma)}$H₂/Lys-$\underline{C}_{(\beta)}$H₂), 30.9 ($\underline{C}_{(\gamma)}$H₂/Lys-$\underline{C}_{(\beta)}$H₂), 30.9 ($\underline{C}_{(\gamma)}$H₂/Lys-$\underline{C}_{(\beta)}$H₂), 31.4 (Glu-$\underline{C}_{(\beta)}$H₂, Pal-$\underline{C}_{(\beta)}$H₂), 31.7 (several Pal-$\underline{C}$H₂), 35.0 (triazolyl-$\underline{C}_{(\beta)}$H₂, overlaps with solvent peak), 35.5 (Pal-$\underline{C}_{(\alpha)}$H₂, overlaps with solvent peak), 38.3 (Lys-$\underline{C}_{(\epsilon)}$H₂), 38.8 (OEG-$\underline{C}$H₂), 49.0 (OCH₂$\underline{C}$H₂N), 49.0 (Ala-$\underline{C}_{(\alpha)}$H), 50.4 (Ala-$\underline{C}_{(\alpha)}$H), 53.4 (Glu-$\underline{C}_{(\alpha)}$H), 53.5 (Glu-$\underline{C}_{(\alpha)}$H), 54.1 (Lys-$\underline{C}_{(\alpha)}$H), 55.6 (C-2), 59.3 (Val-$\underline{C}_{(\alpha)}$H), 59.4 (Val-$\underline{C}_{(\alpha)}$H), 66.3 (C-6), 67.7 (O$\underline{C}$H₂CH₂N), 69.3 (OEG-$\underline{C}$H₂), 69.8 (OEG-$\underline{C}$H₂), 70.2 (OEG-$\underline{C}_{(\alpha)}$H₂), 70.7 (OEG-$\underline{C}$H₂), 70.9 (C-4), 74.4 (C-3), 75.2 (C-5), 101.6 (C-1), 123.1 (triazolyl-HC$\underline{C}_{(\gamma)}$CH$_2$), 146.2 (triazolyl-H$\underline{C}_{(\delta)}$CCH$_2$), 170.0 ($\underline{C}$O), 170.7 ($\underline{C}$O), 171.8 ($\underline{C}$O), 172.3 ($\underline{C}$O), 172.4 ($\underline{C}$O), 172.6 ($\underline{C}$O), 172.7 ($\underline{C}$O), 173.9 ($\underline{C}$O), 174.1 ($\underline{C}$O), 174.2 ($\underline{C}$O), 174.7 (2×$\underline{C}$O), 174.8 ($\underline{C}$O); $^1$H-NMR (600 MHz, DMF-d$_7$): δ 0.86 (t, 3H, J=7.0 Hz, Pal-C$\underline{H}_3$), 0.91-0.95 (m, 12H, 4×Val-C$_{(\gamma)}\underline{H}_3$), 1.22-1.30 (m, 20H, Pal-C$\underline{H}_2$), 1.32-1.36 (m, 1H, Pal-C$\underline{H}_2$), 1.39 (at, 6H, J=7.3 Hz, 2×Ala-C$_{(\beta)}\underline{H}_3$), 1.43-1.53 (m, 3H, Lys-C$_{(\delta)}\underline{H}_2$, Pal-C$\underline{H}_2$), 1.54-1.62 (m, 2H, Pal-C$\underline{H}_2$), 1.70-1.77 (m, 2H, Glu-C$_{(\beta)}\underline{H}_2$), 1.82-1.87 (m, 2H, Pal-C$\underline{H}_2$), 1.88 (s, 3H, acetyl-C$\underline{H}_3$), 2.01-2.18 (m, 6H, Glu-C$_{(\beta)}\underline{H}_2$, Lys-C$_{(\beta)}\underline{H}_2$, 2×Val-C$_{(\beta)}\underline{H}$), 2.27-2.35 (m, 2H, Pal-C$_{(\alpha)}\underline{H}_2$), 2.38-2.51 (m, 6H, Glu-C$_{(\gamma)}\underline{H}_2$, Lys-C$_{(\gamma)}\underline{H}_2$, Glu-C$_{(\gamma)}\underline{H}_2$), 2.59 (t, 2H, J=7.8 Hz, triazolyl-C$_{(\beta)}\underline{H}_2$), 2.93-2.97 (m, 2H, triazolyl-C$_{(\alpha)}\underline{H}_2$), 3.20 (t, 2H, J=7.0 Hz, Lys-C$_{(\epsilon)}\underline{H}_2$), 3.32-3.35 (m, 3H, H-4, OEG-C$\underline{H}_2$), 3.46-3.48 (m, 2H, H-3, H-5), 3.50-3.53 (m, 2H, OEG-C$\underline{H}_2$), 3.60-3.62 (m, 2H, OEG-C$\underline{H}_2$), 3.64-3.66 (m, 2H, OEG-C$\underline{H}_2$), 3.68 (dd, 1H, J=8.5, 10.2 Hz, H-2), 3.92 (m, 1H, OC$\underline{H}_2$CH$_2$N, overlaps with H$_2$O peak), 3.95 (s, 2H, OEG-C$_{(\alpha)}\underline{H}_2$, overlaps with H$_2$O peak), 4.05 (dd, 1H, J=6.2, 11.1 Hz, H-6b), 4.11 (dt, 1H, J=4.4, 11.3 Hz, OC$\underline{H}_2$CH$_2$N), 4.18 (d, 1H, J=7.0 Hz, Val-C$_{(\alpha)}\underline{H}$), 4.21 (d, 1H, J=7.2 Hz, Val-C$_{(\alpha)}\underline{H}$), 4.21-4.24 (m, 3H, Ala-C$_{(\alpha)}\underline{H}$, Glu-C$_{(\alpha)}\underline{H}$, Lys-C$_{(\alpha)}$H), 4.28 (dd, 1H, J=1.8, 11.1 Hz, H-6a), 4.30-4.34 (m, 2H, Ala-C$_{(\alpha)}\underline{H}$, Glu-C$_{(\alpha)}\underline{H}$), 4.48 (d, 1H, J=8.5 Hz, H-1), 4.56 (at, 2H, J=5.1 Hz, OCH$_2$C$\underline{H}_2$N), 7.87 (s, 1H, triazole-H$\underline{C}_{(\delta)}$CCH$_2$); HRMS-ESI [M+H]: calcd for C$_{69}$H$_{120}$N$_{14}$O$_{2}$S, 1577.8348; found 1577.8343; [Cu]: 6.67 ng/mg.

GlcA PA (PA 3)

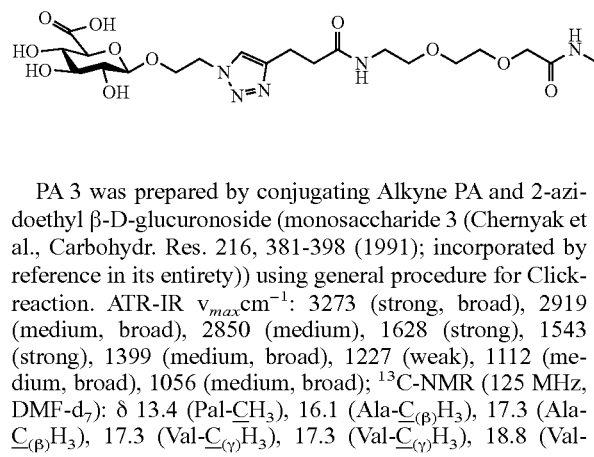

PA 3 was prepared by conjugating Alkyne PA and 2-azidoethyl β-D-glucuronoside (monosaccharide 3 (Chernyak et al., Carbohydr. Res. 216, 381-398 (1991); incorporated by reference in its entirety)) using general procedure for Click-reaction. ATR-IR $v_{max}$cm$^{-1}$: 3273 (strong, broad), 2919 (medium, broad), 2850 (medium), 1628 (strong), 1543 (strong), 1399 (medium, broad), 1227 (weak), 1112 (medium, broad), 1056 (medium, broad); $^{13}$C-NMR (125 MHz, DMF-d$_7$): δ 13.4 (Pal-$\underline{C}$H$_3$), 16.1 (Ala-$\underline{C}_{(\beta)}$H$_3$), 17.3 (Ala-$\underline{C}_{(\beta)}$H$_3$), 17.3 (Val-$\underline{C}_{(\gamma)}$H$_3$), 17.3 (Val-$\underline{C}_{(\gamma)}$H$_3$), 18.8 (Val-$\underline{C}_{(\gamma)}$H$_3$), 18.9 (Val-$\underline{C}_{(\gamma)}$H$_3$), 21.3 (triazolyl-$\underline{C}_{(\alpha)}$H$_2$), 22.2 (Pal-$\underline{C}$H$_2$), 23.2 (Pal-$\underline{C}$H$_2$), 25.6 (Pal-$\underline{C}$H$_2$), 26.9 (Glu-$\underline{C}_{(\beta)}$H$_2$), 27.6 (Glu-$\underline{C}_{(\beta)}$H$_2$), 28.6 (Lys-$\underline{C}_{(\delta)}$H$_2$), 28.7-29.7 (several Pal-$\underline{C}$H$_2$, overlaps with solvent peak), 30.4 (Val-$\underline{C}_{(\beta)}$H), 30.6 (Val-$\underline{C}_{(\beta)}$H), 30.6 (Lys-$\underline{C}_{(\beta)}$H$_2$, Lys-$\underline{C}_{(\gamma)}$H$_2$), 31.4 (Pal-$\underline{C}$H$_2$), 34.6 (Glu-$\underline{C}_{(\gamma)}$H$_2$), 34.8 (triazolyl-$\underline{C}_{(\beta)}$H$_2$), 35.3 (Glu-$\underline{C}_{(\gamma)}$H$_2$), 35.3 (Pal-$\underline{C}_{(\alpha)}$H$_2$), 38.2 (Lys-$\underline{C}_{(\epsilon)}$H$_2$), 38.6 (OEG-$\underline{C}$H$_2$), 48.4 (Ala-C$_{(\alpha)}$H), 49.8 (O$\underline{C}$H$_2$CH$_2$N), 50.5 (Lys-$\underline{C}_{(\alpha)}$H/Glu-C$_{(\alpha)}$H), 53.3 (Lys-$\underline{C}_{(\alpha)}$H/Glu-C$_{(\alpha)}$H), 54.9 (Ala-C$_{(\alpha)}$H), 56.0 (Glu-C$_{(\alpha)}$H), 58.2 (Val-C$_{(\alpha)}$H), 58.4 (Val-C$_{(\alpha)}$H), 67.9 (OEG-$\underline{C}_{(\alpha)}$H$_2$), 69.0 (OEG-$\underline{C}$H$_2$), 69.5 (OEG-$\underline{C}$H$_2$), 69.9 (O$\underline{C}$H$_2$CH$_2$N), 70.3 (OEG-$\underline{C}$H$_2$), 72.1 (C-4), 73.3 (C-2), 74.0 (C-5), 76.3 (C-3), 102.9 (C-1), 123.5 (triazolyl-H$\underline{C}\underline{C}_{(\gamma)}$CH$_2$), 146.0 (triazolyl-H$\underline{C}_{(\delta)}$CCH$_2$), 170.3 ($\underline{C}$O), 171.3 ($\underline{C}$O), 172.0 ($\underline{C}$O), 172.8 ($\underline{C}$O), 172.9 ($\underline{C}$O), 173.7 ($\underline{C}$O), 173.8 (2×$\underline{C}$O), 174.0 ($\underline{C}$O), 174.9 ($\underline{C}$O), 175.3 ($\underline{C}$O), 178.3 ($\underline{C}$O), 178.5 ($\underline{C}$O); $^1$H-NMR (600 MHz, DMF-d$_7$): δ 0.84 (t, 3H, J=6.9 Hz, Pal-C$\underline{H}_3$), 0.87-0.90 (m, 12H, Val-C$_{(\gamma)}\underline{H}_3$), 1.20-1.28 (m, 22H, Pal-C$\underline{H}_2$), 1.30-1.36 (m, 2H, Pal-C$\underline{H}_2$), 1.38 (d, 3H, J=7.2 Hz, Ala-C$_{(\beta)}\underline{H}_3$), 1.41 (d, 3H, J=7.1 Hz, Ala-C$_{(\beta)}\underline{H}_3$), 1.44-1.58 (m, 2H, Lys-C$_{(\delta)}\underline{H}_2$), 1.53-1.58 (m, 2H, Pal-C$\underline{H}_2$), 1.74-1.81 (m, 2H, Lys-C$_{(\beta)}\underline{H}_2$), 1.84-1.89 (m, 2H, Lys-C$_{(\gamma)}\underline{H}_2$), 1.93-2.01 (m, 2H, Glu-C$_{(\beta)}\underline{H}_2$), 2.06-2.13 (m, 4H, Glu-C$_{(\beta)}\underline{H}_2$, Val-C$_{(\beta)}\underline{H}$, Val-C$_{(\beta)}\underline{H}$), 2.17-2.32 (m, 6H, Glu-C$_{(\gamma)}\underline{H}_2$, Pal-C$_{(\alpha)}\underline{H}_2$, Glu-C$_{(\gamma)}\underline{H}_2$), 2.57 (t, 2H, J=7.7 Hz, triazolyl-C$_{(\beta)}\underline{H}_2$), 2.93-2.96 (m, 2H, triazolyl-C$_{(\alpha)}\underline{H}_2$, overlaps with solvent peak), 3.17-3.22 (m, 3H, H-2, Lys-C$_{(\epsilon)}\underline{H}_2$), 3.31-3.43 (m, 4H, H-3, H-4, OEG-C$\underline{H}_2$), 3.49-3.54 (m, 3H, H-5, OEG-C$\underline{H}_2$), 3.61-3.62 (m, 2H, OEG-C$\underline{H}_2$), 3.64-3.65 (m, 2H, OEG-C$\underline{H}_2$), 3.69-4.04 (m, 3H, OC$\underline{H}_2$CH$_2$N, Glu-C$_{(\alpha)}\underline{H}$), 4.12 (t, 2H, J=7.0 Hz, Glu-C$_{(\alpha)}\underline{H}$), 4.15-4.20 (m, 2H, Lys-C$_{(\alpha)}\underline{H}$, Ala-C$_{(\alpha)}\underline{H}$), 4.27-4.30 (m, 2H, 2×Val-C$_{(\alpha)}\underline{H}$, overlaps with H$_2$O), 4.27 (s, 2H, OEG-C$_{(\alpha)}\underline{H}$), 4.37 (d, 1H, J=7.8 Hz, H-1), 4.48 (q, 1H, J=7.0 Hz, Ala-C$_{(\alpha)}\underline{H}$), 4.59-4.65 (m, 2H, OCH$_2$C$\underline{H}_2$N), 8.16 (s, 1H, triazole-H$\underline{C}_{(\delta)}$CCH$_2$); HRMS-ESI [M+H]: calcd for C$_{67}$H$_{115}$N$_{13}$O$_{23}$, 1470.8307; found 1470.8284; [Cu]: 7.44 ng/mg.

GlcNAc PA (PA 4)

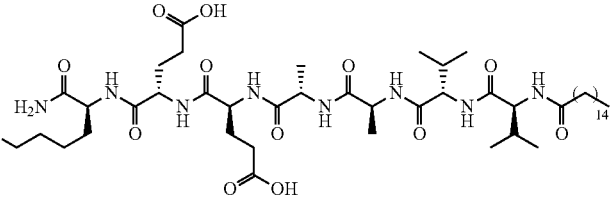

PA 4 was prepared by conjugating Alkyne PA and 2-Azidoethyl 2-acetamido-2-deoxy-β-D-glucopyranoside (monosaccharide 4 (Eklind et al. J. Carbohyd. Chem. 15, 1161-1178 (1996); incorporated by reference in its entirety)) following general procedure for Click-reaction. ATR-IR $v_{max}$cm$^{-1}$: 3273 (strong, broad), 2919 (medium), 2850 (weak), 1627 (strong), 1542 (strong), 1396 (medium, broad), 1226 (weak), 1075 (medium, broad), 1059 (medium, broad); $^{13}$C-NMR (125 MHz, DMF-d$_7$: δ 13.7 (Pal-$\underline{C}$H$_3$), 16.1 (Ala-$\underline{C}_{(\beta)}$H$_3$), 17.9 (Ala-$\underline{C}_{(\beta)}$H$_3$), 18.1 (2×Val-$\underline{C}_{(\gamma)}$H$_3$), 19.2 (Val-$\underline{C}_{(\gamma)}$H$_3$), 19.4 (Val-$\underline{C}_{(\gamma)}$H$_3$), 21.7 (triazolyl-$\underline{C}_{(\alpha)}$H$_2$), 22.5 (Pal-$\underline{C}$H$_2$), 22.6 (acetyl- $\underline{C}$H$_3$), 23.8 (Pal-$\underline{C}$H$_2$), 25.9 (Pal-$\underline{C}$H$_2$), 26.8 (Lys-$\underline{C}_{(\beta)}$H$_2$), 27.8 (Glu-$\underline{C}_{(\beta)}$H$_2$), 29.2 (Lys-$\underline{C}_{(\delta)}$H$_2$), 29.3-29.8 (several Pal-$\underline{C}$H$_2$, overlaps with solvent peak), 30.5 (Val-$\underline{C}_{(\beta)}$H), 30.8 (Glu-$\underline{C}_{(\beta)}$H$_2$), 30.9 (Pal-$\underline{C}_{(\beta)}$H$_2$), 31.0 (Val-$\underline{C}_{(\beta)}$H), 31.8 (Pal-$\underline{C}$H$_2$), 34.6-35.9 (2×Glu-$\underline{C}_{(\gamma)}$H$_2$, Lys-$\underline{C}_{(\gamma)}$H$_2$, Pal-$\underline{C}_{(\alpha)}$H$_2$), 35.1 (triazolyl-$\underline{C}_{(\beta)}$H$_2$), 38.5 (Lys-$\underline{C}_{(\epsilon)}$H$_2$), 38.9 (OEG-$\underline{C}$H$_2$), 48.6 (Ala-C$_{(\alpha)}$H), 49.9 (O$\underline{C}$H$_2$CH$_2$N), 51.2 (Ala-C$_{(\alpha)}$H/Glu-C$_{(\alpha)}$H), 53.7 (Ala-C$_{(\alpha)}$H/Glu-C$_{(\alpha)}$H), 55.6 (Glu-C$_{(\alpha)}$H), 55.6 (C-2), 57.2 (Lys-$\underline{C}_{(\alpha)}$H$_2$), 58.6 (Val-C$_{(\alpha)}$H), 58.9 (Val-C$_{(\alpha)}$H), 61.7 (C-6), 67.2 (O$\underline{C}$H$_2$CH$_2$N), 69.5 (OEG-CH$_2$), 69.9 (OEG-$\underline{C}$H$_2$), 70.3 (OEG-$\underline{C}_{(\alpha)}$H$_2$), 70.6 (OEG-$\underline{C}$H$_2$), 71.0 (C-4/C-5), 74.7 (C-3), 77.4 (C-4/C-5), 101.4 (C-1), 122.9 (triazolyl-H$\underline{CC}_{(\gamma)}$CH$_2$), 146.4 (triazolyl-H$\underline{C}_{(\delta)}$CCH$_2$), 169.9 ($\underline{C}$O), 170.8 ($\underline{C}$O), 171.3 ($\underline{C}$O), 172.1 ($\underline{C}$O), 172.2, 172.7 ($\underline{C}$O), 173.3 ($\underline{C}$O), 173.8 ($\underline{C}$O), 174.0 ($\underline{C}$O), 175.0 ($\underline{C}$O), 175.3 ($\underline{C}$O), 177.8 ($\underline{C}$O), 178.1 ($\underline{C}$O); $^1$H-NMR (600 MHz, DMF-d$_7$): δ 0.85 (t, 3H, J=6.9 Hz, Pal-C$\underline{H}_3$), 0.90 (at, 12H, J=7.1 Hz, 4×Val-C$_{(\gamma)}\underline{H}_3$), 1.22-1.37 (m, 20H, Pal-C$\underline{H}_2$), 1.40 (d, 3H, J=7.1 Hz, Ala-C$_{(\beta)}\underline{H}_3$), 1.45 (d, 3H, J=7.0 Hz, Ala-C$_{(\beta)}\underline{H}_3$), 1.48-1.59 (m, 6H, Lys-C$_{(\delta)}\underline{H}_2$, 2×Pal-C$\underline{H}$2), 1.78-1.85 (m, 2H, Glu-C$_{(\beta)}\underline{H}_2$), 1.85-1.90 (m, 2H, Pal-C$_{(\beta)}\underline{H}_2$), 1.90 (s, 3H, acetyl-C$\underline{H}_3$), 1.94-1.97 (m, 2H, Lys-C$_{(\beta)}\underline{H}_2$), 2.11-2.17 (m, 4H, Glu-C$_{(\beta)}\underline{H}_2$, 2×Val-C$_{(\beta)}\underline{H}$), 2.18-2.40 (m, 8H, Glu-C$_{(\gamma)}\underline{H}_2$, Glu-C$_{(\gamma)}\underline{H}_2$, Lys-C$_{(\gamma)}\underline{H}_2$, Pal-C$_{(\beta)}\underline{H}_2$), 2.95 (t, 2H, J=7.9 Hz, triazolyl-C$_{(\beta)}\underline{H}_2$), 2.75 (m, 2H, triazolyl-C$_{(\alpha)}\underline{H}_2$, overlaps with solvent peak), 3.19-3.22 (m, 2H, Lys-C$_{(\epsilon)}\underline{H}_2$), 3.29-3.31 (m, 2H, H-4, H-5), 3.33-3.35 (m, 2H, OEG-C$\underline{H}_2$), 3.50-3.52 (t, 2H, J=5.7 Hz, OEG-C$\underline{H}_2$), 3.54 (dd, 1H, J=8.3, 10.1 Hz, H-3), 3.58-3.66 (m, 5H, H-6b, OEG-C$\underline{H}_2$, OEG-C$\underline{H}_2$), 3.70 (dd, 1H, J=8.6, 10.1 Hz, H-2), 3.85 (m, 1H, H-6a, overlaps with H$_2$O peak), 3.88 (m, 1H, OC$\underline{H}_2$CH$_2$N, overlaps with H$_2$O peak), 3.90 (m, 1H, Lys-C$_{(\alpha)}\underline{H}$, overlaps with H$_2$O peak), 3.95 (s, 2H, OEG-C$_{(\alpha)}\underline{H}_2$), 4.06 (t, 1H, J=6.7 Hz, Glu-C$_{(\alpha)}\underline{H}$), 4.13-4.18 (m, 3H, OC$\underline{H}_2$CH$_2$N, Glu-C$_{(\alpha)}\underline{H}$, Ala-C$_{(\alpha)}\underline{H}$), 4.31 (ad, 2H, J=7.3 Hz, Val-C$_{(\alpha)}\underline{H}$), 4.48 (d, 1H, J=8.6 Hz, H-1), 4.51-4.61 (m, 3H, OCH$_2$C$\underline{H}_2$N, Ala-C$_{(\alpha)}\underline{H}$), 7.84 (s, 1H, triazole-$\underline{H}$C$_{(\delta)}$CCH$_2$); HRMS-ESI [M+H]: calcd for C$_{69}$H$_{120}$N$_{14}$O$_{22}$, 1497.8780; found 1497.8777; [Cu]: 6.99 ng/mg.

OEG PA (PA 5)

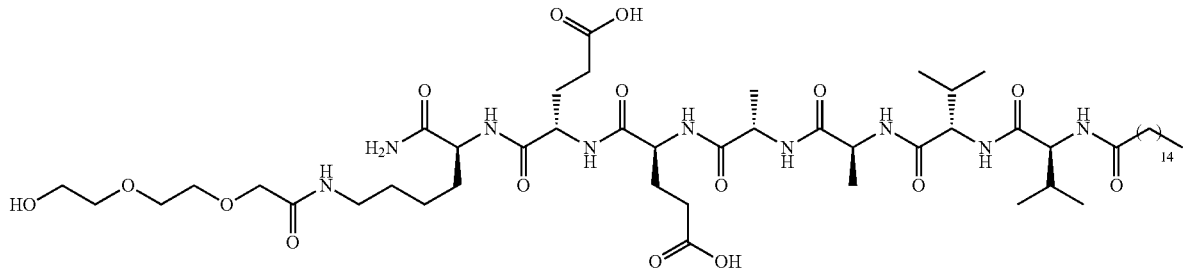

PA 5 was prepared using solid-phase peptide synthesis where Lys(Mtt) was selectively deprotected and coupled to HO-OEG$_2$-CH$_2$COOH (36). ATR-IR $v_{max}$cm$^{-1}$: 3276 (strong, broad), 2919 (strong), 2850 (medium), 1626 (strong), 1541 (strong), 1451 (weak), 1397 (weak), 1226 (medium), 1113 (weak); $^{13}$C-NMR (125 MHz, DMSO-d$_6$): δ 14.2 (Pal-$\underline{C}$H$_3$), 17.8 (2×Ala-$\underline{C}_{(\beta)}$H$_3$), 18.3 (Val-$\underline{C}_{(\gamma)}$H$_3$), 18.5 (Val-$\underline{C}_{(\gamma)}$H$_3$), 19.4 (Val-$\underline{C}_{(\gamma)}$H$_3$), 19.5 (Val-$\underline{C}_{(\gamma)}$H$_3$), 22.3 (Pal-C$\underline{H}_2$), 23.0 (Pal-$\underline{C}$H$_2$), 25.6 (Pal-$\underline{C}_{(\beta)}$H$_2$), 27.2 (Glu-$\underline{C}_{(\beta)}$H$_2$), 27.3 (Glu-$\underline{C}_{(\beta)}$H$_2$), 28.7 (Pal-$\underline{C}$H$_2$), 28.9 (Pal-$\underline{C}$H$_2$), 29.0 (Pal-$\underline{C}$H$_2$), 29.0 (Lys-$\underline{C}_{(\delta)}$H$_2$), 29.1-29.2 (several Pal-C$\underline{H}_2$), 30.2 (Glu-$\underline{C}_{(\gamma)}$H$_2$), 30.3 (Glu-$\underline{C}_{(\gamma)}$H$_2$), 30.4 (Val-$\underline{C}_{(\beta)}$H), 30.6 (Val-$\underline{C}_{(\beta)}$H), 31.5 (Pal-$\underline{C}$H$_2$), 31.5 (Lys-$\underline{C}_{(\gamma)}$H$_2$, Lys-$\underline{C}_{(\beta)}$H$_2$), 35.3 (Pal-$\underline{C}_{(\alpha)}$H$_2$), 38.1 (Lys-$\underline{C}_{(\epsilon)}$H$_2$), 48.3 (Ala-$\underline{C}_{(\alpha)}$H), 48.6 (Ala-$\underline{C}_{(\alpha)}$H), 52.0 (Glu-$\underline{C}_{(\alpha)}$H), 52.3 (Glu-$\underline{C}_{(\alpha)}$H), 52.7 (Lys-$\underline{C}_{(\alpha)}$H), 57.7 (Val-C$_{(\alpha)}$H), 58.1 (Val-C$_{(\alpha)}$H), 60.3 (OEG-$\underline{C}$H$_2$), 69.7 (OEG-$\underline{C}_{(\alpha)}$H$_2$), 70.1 (OEG-C$\underline{H}_2$), 70.5 (OEG-C$\underline{H}_2$), 72.4 (OEG-C$\underline{H}_2$), 169.5 ($\underline{C}$O), 170.9 ($\underline{C}$O), 171.0 ($\underline{C}$O), 171.4 ($\underline{C}$O), 171.5 ($\underline{C}$O), 172.3 (C$\underline{O}$), 172.7 ($\underline{C}$O), 172.9 ($\underline{C}$O), 173.8 ($\underline{C}$O), 174.2 ($\underline{C}$O), 174.2 ($\underline{C}$O); $^1$H-NMR (600 MHz, DMSO-d$_6$): δ 0.79-0.84 (m, 15H, Pal-CH$_3$, 4×Val-CH3), 1.18-1.26 (m, 30H, 2×Ala-C$\underline{H}_3$, Pal-C$\underline{H}_2$), 1.37-1.41 (m, 2H, Lys-C$_{(\delta)}\underline{H}_2$), 1.43-1.49 (m, 2H, Pal-C$_{(\beta)}\underline{H}_2$), 1.49-1.54 (m, 2H, Lys-C$_{(\beta)}\underline{H}_2$), 1.59-1.65 (m, 2H, Lys-C$_{(\gamma)}\underline{H}_2$), 1.72-1.78 (m, 2H, Glu-C$_{(\beta)}\underline{H}_2$), 1.86-1.97 (m, 4H, Glu-C$_{(\beta)}\underline{H}_2$, 2×Val-C$_{(\beta)}\underline{H}$), 2.08-2.18 (m, 2H, Pal-C$_{(\alpha)}\underline{H}_2$), 2.21-2.25 (m, 4H, 2×Glu-C$_{(\gamma)}\underline{H}_2$), 3.06 (t, 2H, J=7.3 Hz, Lys-C$_{(\epsilon)}\underline{H}_2$), 3.42 (t, 2H, J=5.1 Hz, OEG-C$\underline{H}_2$), 3.49 (t, 2H, J=5.1 Hz, OEG-C$\underline{H}_2$), 3.54 (m, 2H, OEG-C$\underline{H}_2$, overlap with H$_2$O peak), 3.55 (m, 2H, OEG-C$\underline{H}_2$, overlap with H$_2$O peak), 3.85 (s, 2H, OEG-C$_{(\alpha)}\underline{H}_2$), 4.07 (dd, 1H, J=5.4, 9.0 Hz, Lys-C$_{(\alpha)}\underline{H}$), 4.10 (d, 1H, J=6.9 Hz, Val-C$_{(\alpha)}\underline{H}$), 4.12 (d, 1H, J=7.2 Hz, Val-C$_{(\alpha)}\underline{H}$), 4.16-4.23 (m, 4$\underline{H}$, 2×Ala-C$_{(\alpha)}\underline{H}$, 2×Glu-C$_{(\alpha)}\underline{H}$); HRMS-ESI [M+H]: calcd for C$_{54}$H$_{97}$N$_9$O$_{16}$, 1128.7132; found 1128.7123.

E2 PA (PA 6)

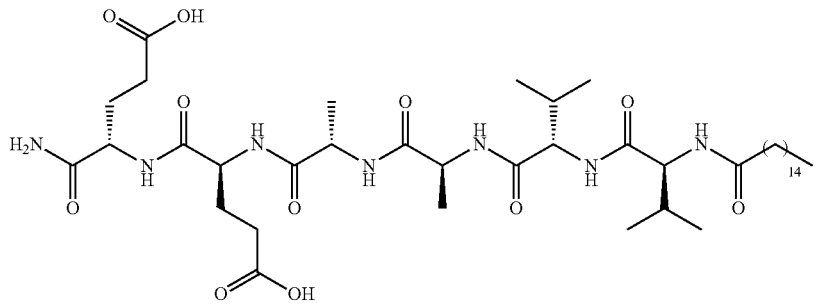

PA 6 was synthesized according to general procedures. ATR-IR $v_{max}$cm$^{-1}$: 3278 (strong, broad), 2919 (strong), 2851 (medium), 1627 (strong), 1539 (strong), 1451 (weak), 1398 (weak), 1226 (medium), 1162 (weak); $^{13}$C-NMR (125 MHz, DMSO-d$_6$): δ=14.2 (Pal-CH$_3$), 17.8 (Ala-C$_{(β)}$H$_3$), 17.8 (Ala-$\underline{C}_{(β)}$H$_3$), 18.3 (Val-$\underline{C}_{(γ)}$H$_3$), 18.5 (Val-$\underline{C}_{(γ)}$H$_3$), 19.3 (Val-$\underline{C}_{(γ)}$H$_3$), 19.4 (Val-$\underline{C}_{(γ)}$H$_3$), 22.3 (Pal-$\underline{C}$H$_2$), 25.6 (Pal-$\underline{C}$H$_2$), 27.1 (Glu-$\underline{C}_{(β)}$H$_2$), 27.3 (Glu-$\underline{C}_β$H$_2$), 28.7 (Pal-$\underline{C}$H$_2$), 28.9 (Pal-$\underline{C}$H$_2$), 28.9 (Pal-$\underline{C}$H$_2$), 29.1-29.2 (several Pal-$\underline{C}$H$_2$), 30.1 (Val-$\underline{C}_{(β)}$H), 30.2 (Glu-$\underline{C}_{(γ)}$H$_2$), 30.5 (Val-$\underline{C}_{(β)}$H), 30.6 (Glu-$\underline{C}_{(γ)}$H$_2$), 31.5 (Pal-$\underline{C}$H$_2$), 35.3 (Pal-$\underline{C}_{(α)}$), 48.3 (Ala-C$_{(α)}$), 48.6 (Ala-$\underline{C}_{(α)}$H), 51.8 (Glu-$\underline{C}_{(α)}$H), 52.2 (Glu-$\underline{C}_{(α)}$), 57.7 (Val-$\underline{C}_{(α)}$H), 58.1 (Val-$\underline{C}_{(α)}$H), 170.8 ($\underline{C}$O), 171.1 ($\underline{C}$O), 171.5 ($\underline{C}$O), 172.2 ($\underline{C}$O), 172.6 ($\underline{C}$O), 172.6 ($\underline{C}$O), 172.7 ($\underline{C}$O), 173.1 ($\underline{C}$O), 174.1 ($\underline{C}$O); $^1$H-NMR (600 MHz, DMSO-d$_6$): δ=0.78-0.83 (15H, m, Pal-CH$_3$, 4×Val-CH3), 1.16-1.22 (30H, m, Pal-CH$_2$, 2×Ala-CH$_3$), 1.42-1.48 (2H, m, Pal-CH$_2$), 1.69-1.77 (2H, m, Glu-C$_{(β)}$H$_2$), 1.86-1.91 (2H, m, Glu-C$_{(β)}$H$_2$), 1.91-1.96 (2H, m, 2×Val-C$_{(β)}$H), 2.06-2.17 (2H, m, Pal-C$_{(α)}$H$_2$), 2.17-2.23 (4H, m, 2×Glu-C$_{(γ)}$H$_2$), 4.09 (1H, d, J=6.8 Hz, Val-C$_{(α)}$H), 4.10-4.12 (2H, m, Glu-C$_{(α)}$H, Val-C$_{(α)}$H), 4.14-4.18 (2H, m, Glu-C$_{(α)}$H, Ala-C$_{(α)}$H), 4.21 (1H, q, J=7.1 Hz, Ala-C$_{(α)}$H); HRMS-ESI [M+H]: calcd for C$_{42}$H$_{75}$N$_7$O$_{11}$, 854.5603; found 854.5606.

Alkyne-PA (PA 7)

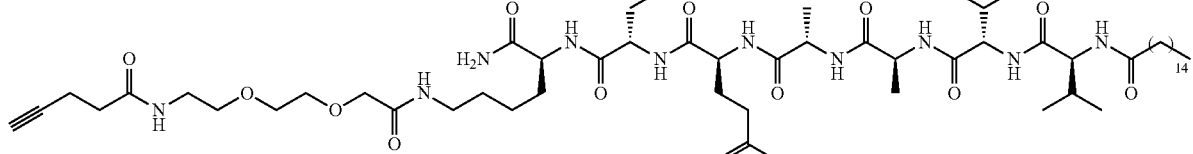

PA 7 was synthesized using solid-phase peptide synthesis. The lysyl-(Mtt) was selectively deprotected and Fmoc-NH-OEG$_2$-CH$_2$COOH was coupled using general procedure. Fmoc-deprotection followed by subsequent coupling of 4-pentynoic acid generated the resin-bound PA 7 which was cleaved from resin using general procedures. ATR-IR $v_{max}$cm$^{-1}$: 3199 (medium, broad), 3049 (strong, broad), 2895 (strong, broad), 1628 (strong), 1546 (medium), 1469 (medium), 1435 (medium), 1177 (strong), 1124 (strong), 840 (strong), 801 (strong), 725 (strong); $^{13}$C-NMR (125 MHz, DMF-d$_7$): δ 13.7 (Pal-CH$_3$), 14.5 (Alkyne-$\underline{C}_{(β)}$H$_2$), 16.4 (Ala-$\underline{C}_{(β)}$H$_3$), 16.5 (Ala-$\underline{C}_{(β)}$H$_3$), 18.6 (Val-$\underline{C}_{(γ)}$H$_3$), 18.8 (Val-$\underline{C}_{(γ)}$H$_3$), 19.0 (Val-$\underline{C}_{(γ)}$H$_3$), 19.0 (Val-$\underline{C}_{(γ)}$H$_3$), 22.5 (several peaks Pal-$\underline{C}$H$_2$), 23.4 (2×Val-$\underline{C}_{(β)}$H), 25.7 (Pal-$\underline{C}_{(β)}$H$_2$), 26.5 (Glu-$\underline{C}_{(β)}$H$_2$), 26.8 (Glu-$\underline{C}_{(β)}$H$_2$), 29.0 (Lys-$\underline{C}_{(δ)}$H$_2$, overlaps with solvent peak), 29.3-29.7 (several peaks Pal-$\underline{C}$H$_2$, overlaps with solvent peak), 29.7 (Alkyne-H$\underline{C}_{(δ)}$CCH$_2$, overlaps with solvent peak), 30.5 (Glu-$\underline{C}_{(γ)}$H$_2$), 30.6 (Glu-$\underline{C}_{(γ)}$H$_2$), 31.1 (Pal-$\underline{C}$H$_2$), 31.3 (Lys-$\underline{C}_{(γ)}$H$_2$), 31.5 (Lys-$\underline{C}_{(β)}$H$_2$), 31.8 (Pal-$\underline{C}$H$_2$), 34.5 (Alkyne-$\underline{C}_{(α)}$H$_2$, overlaps with solvent peak), 35.5 (Pal-$\underline{C}_{(α)}$H$_2$), 38.4 (Lys-$\underline{C}_{(ε)}$H$_2$), 39.0 (OEG-$\underline{C}$H$_2$), 50.6 (Lys-$\underline{C}_{(α)}$), 50.7 (Ala-C$_{(α)}$H), 53.6 (Val-C$_{(α)}$H), 53.7 (Val-C$_{(α)}$H), 54.3 (Ala-C$_{(α)}$H), 60.7 (Glu-C$_{(α)}$H), 60.8 (Glu-C$_{(α)}$H), 69.5 (OEG-CH$_2$), 69.9 (OEG-CH$_2$), 70.3 (OEG-C$_{(α)}$H$_2$), 70.7 (OEG-CH$_2$), 83.6 (Alkyne-HC$\underline{C}_{(γ)}$CH$_2$), 169.9 ($\underline{C}$O), 171.2 ($\underline{C}$O), 171.9 ($\underline{C}$O), 173.4 ($\underline{C}$O), 172.9 ($\underline{C}$O), 174.2 ($\underline{C}$O), 174.3 ($\underline{C}$O), 174.3 ($\underline{C}$O), 174.6 ($\underline{C}$O), 174.6 ($\underline{C}$O), 174.7 ($\underline{C}$O), 174.7 ($\underline{C}$O); $^1$H-NMR (600 MHz, DMF-d$_7$): δ 0.86 (t, 3H, J=6.8 Hz, Pal-CH$_3$), 0.92 (d, 3H, J=6.8 Hz, Val-CH3), 0.96 (ad, 6H, J=6.7 Hz, Val-CH3), 0.99 (d, 3H, J=6.8 Hz, Val-CH$_3$), 1.22-1.31 (m, 24H, Pal-CH$_2$), 1.34-1.38 (m, 1H, Val-C$_{(β)}$H), 1.40 (d, 3H, J=7.5 Hz, Ala-CH$_3$), 1.43 (d, 3H, J=7.2 Hz, Ala-CH$_3$), 1.47-1.53 (m, 3H, Lys-C$_{(δ)}$H$_2$, Val-C$_{(β)}$H), 1.57-1.61 (m, 2H, Pal-C$_{(β)}$H$_2$), 1.72-1.79 (2H, m, Lys-C$_{(β)}$H$_2$), 1.83-1.88 (2H, m, Lys-C$_{(γ)}$H$_2$), 2.05-2.19 (m, 5H, Alkyne-$\underline{H}$C$_{(δ)}$CCH$_2$, Glu-C$_{(β)}$H$_2$), 2.31 (dd, 1H, J=7.1, 14.7 Hz, Pal-C$_{(α)}$H$_2$), 2.36 (dd, 1H, J=7.4, 14.7 Hz, Pal-C$_{(α)}$H$_2$), 2.39-2.46 (m, 5H, Alkyne-C$_{(α)}$H$_2$, Alkyne-C$_{(β)}$H$_2$, Glu-C$_{(γ)}$H$_2$), 2.54-2.61 (m, 3H, Glu-C$_{(γ)}$H$_2$), 3.18-3.22 (m, 2H, Lys-C$_{(ε)}$H$_2$), 3.34 (t, 2H, J=5.7 Hz, OEG-CH$_2$), 3.52 (t, 2H, J=5.7 Hz, OEG-CH$_2$), 3.60-3.62 (m, 2H, OEG-CH$_2$), 3.64-3.65 (m, 2H, OEG-CH$_2$), 3.95 (s, 2H, OEG-C$_{(α)}$H$_2$), 4.06 (at, 2H, J=6.8 Hz, 2×Glu-C$_{(α)}$H), 4.14-4.23 (m, 3H, Lys-C$_{(α)}$H, 2×Ala-C$_{(α)}$H), 4.28 (d, 1H, J=5.1 Hz, Val-C$_{(α)}$H), 4.29 (d, 1H, J=4.5 Hz, Val-C$_{(α)}$H); HRMS-ESI [M+H]: calcd for C$_{59}$H$_{102}$N$_{10}$O$_{16}$, 1207.7554; found 1207.7542.

Cy3-PA

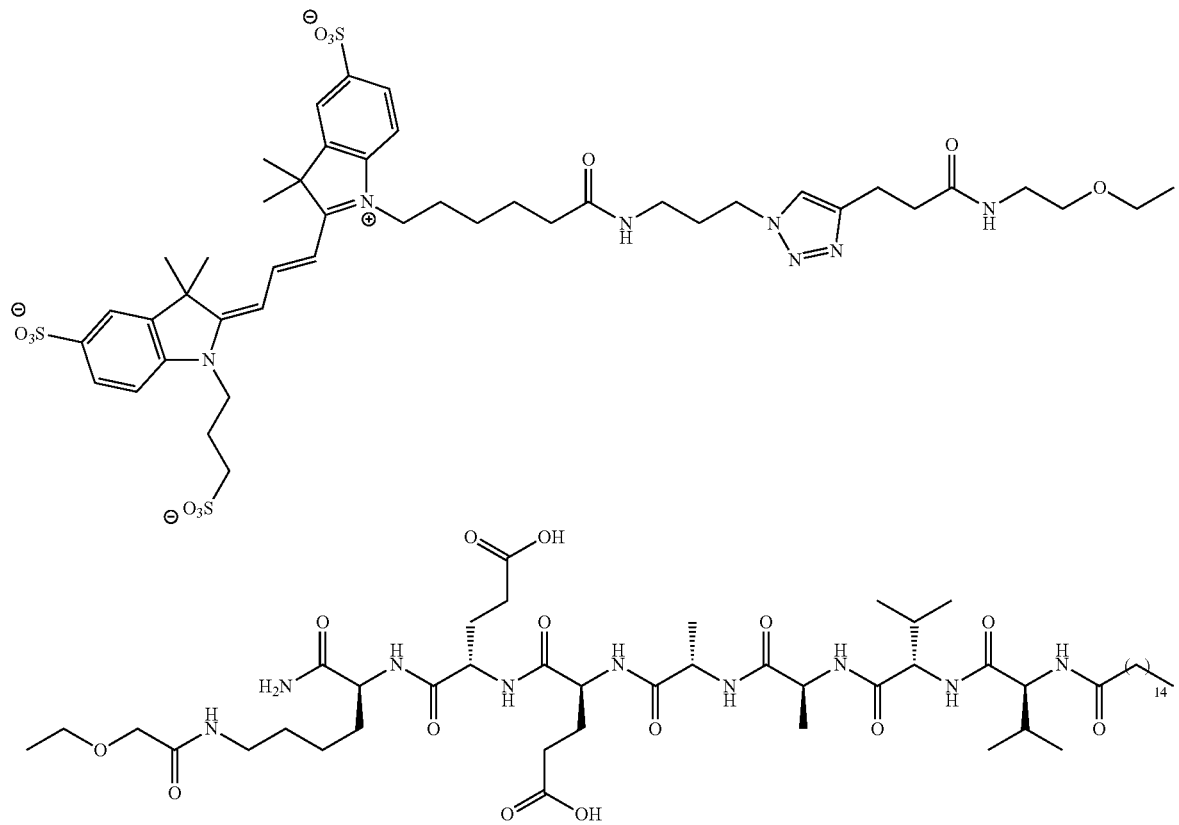

Cy3 conjugated PA (Cy3-PA) was synthesized on a 1 mg scale using Alkyne PA and commercially available Cy3-Azide (Click Chemistry Tools) as starting material following general procedure for click reaction. HRMS-ESI [M−2H]: calcd for $C_{94}H_{148}N_{16}O_{26}S_3$, 2012.9933; found 2012.9913.

Cy5-BMP-2

Cy5 conjugated BMP-2 was prepared by gently mixing 50 μL BMP-2 (1.5 mg/mL or 57 μM) with commercially available Cy5—NHS (Click Chemistry Tools) in 50 μL Milli-Q water (23.9 mM) and "rocked" overnight at room temperature. The mixture was transferred to a Centrifugal Filter Units (Millipore, 3 kDa cut-off) and centrifuged for 30 min at 14.000 g (4° C.). 100 μL Milli-Q water was added and the centrifugation step was repeated. The final Cy5-labeled protein solution was adjusted with Milli-Q water to be exactly 50 μL (57 μM). See Maldi-TOF spectra for verification of conjugation.

Example 2

Materials and Methods

Materials: Unless stated otherwise, recombinant human bone morphogenetic protein 2 (BMP-2) (ref. 11; incorporated by reference in its entirety), BMP-4 (ref. 12; incorporated by reference in its entirety), vascular endothelial growth factor (VEGF) (ref. 15; incorporated by reference in its entirety), acidic fibroblast growth factor (FGF-1) (ref. 16; incorporated by reference in its entirety), basic FGF (FGF-2) (ref. 17; incorporated by reference in its entirety), Sonic hedgehog (Shh) (ref. incorporated by reference in its entirety=14), and murine Noggin (ref. 13; incorporated by reference in its entirety) from *E. coli* were purchased from PeproTech, in their mature forms, highly pure (>98% pure), carrier free and lyophilized. For confocal fluorescence microscopy and C2C12 cell differentiation assays, recombinant human BMP-2 obtained from Medtronic Sofamor Danek (Minneapolis, Minn.) was used. GFs were reconstituted and stored according to the manufacturer's instructions. Heparin sodium (sodium: 9.5-12.5%) and heparan sulfate were purchased from Celsus Laboratory. To compare side-by-side with the glycopeptide assemblies, heparin's average molecular weight per monosaccharide was determined to be 279 g/mol by averaging the molecular weight of three dominant monosaccharides found in the biopolymer.

Cryogenic Transmission Electron Microscopy: PAs 1-5 were dissolved to 5 mM in saline (147 mM NaCl and 3 mM KCl) with 5 mM $CaCl_2$), pH 7.2, thermally annealed at 80° C. for 30 min and slowly cooled to room temperature. PA 6 was dissolved to 5 mM in saline with 1 mM $CaCl_2$, then thermally annealed. PA solutions were spun down, pipetted for homogeneous mixing, and diluted to 25 μM in saline with 2 mM $CaCl_2$. Cryo-TEM specimens were prepared using a Vitrobot Mark IV (FEI) by pipetting a 7 μL drop onto both sides of a lacey carbon grid at room temperature. PA samples were blotted twice at 100% humidity, plunge-froze in liquid ethane, and stored in liquid $N_2$ prior to imaging. Cryo-TEM was performed using a JEOL 1230 microscope at 100 kV accelerating voltage.

Figure 1A:
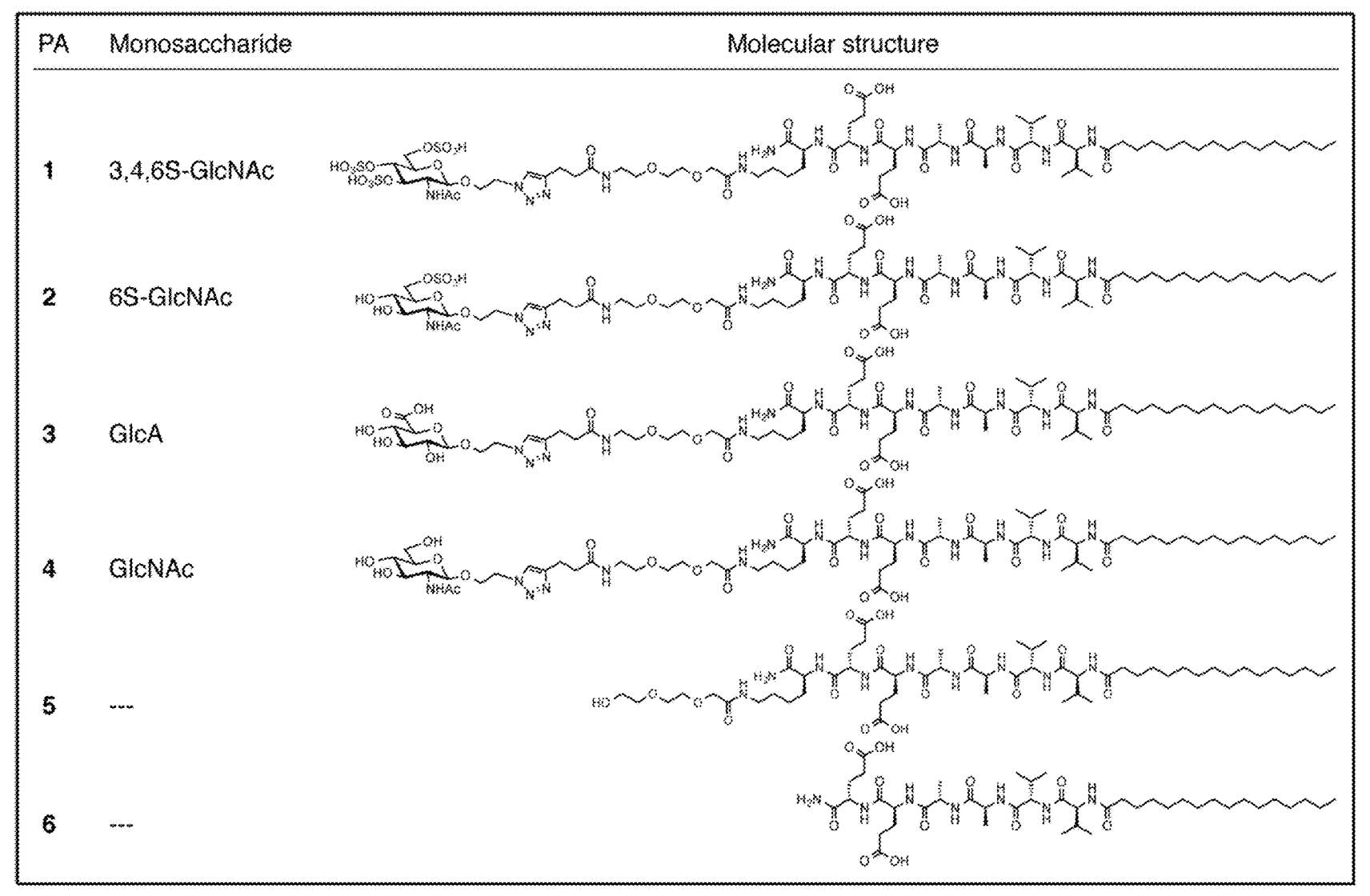

SAXS Studies: PAs 1-5 were dissolved to 6 mM in saline with 6 mM $CaCl_2$, pH 7.2, thermally annealed at 80° C. for 30 min and slowly cooled to room temperature. PA 6 was dissolved to 6 mM in saline with 2 mM $CaCl_2$, then thermally annealed. PA solutions were spun down and pipetted for homogeneous mixing. Small-angle X-ray scattering (SAXS) experiments were performed at the DuPoint-Northwestern-Dow Collaborative Access Team (DND-CAT) Synchrotron Research Center at the Advanced Photon Source, Argonne National Laboratory. A double-crystal monochromator was used to select the X-ray energy at 17 keV ($\lambda$=0.83 Å), and the SAXS CCD camera was placed 245 cm behind the samples to record the scattering intensity in the interval $0.002 < q < 0.146$ Å$^{-1}$. The wave vector q is defined as $=(4\pi/\lambda) \sin(\theta/2)$, where $\theta$ is the scattering angle. Here, the diameter of a nanostructure in solution d is defined as $=2\pi/q$. Samples were placed in 1.5 mm diameter quartz capillary tubes and irradiated with X-ray for 5 s. The 2D scattering images were averaged using azimuthal integration (Fit2D) to produce 1D profiles. Scattering profiles were plotted on a relative scale as a function of the wave vector. For nanostructure analysis (FIG. 1C), background scattering from saline was subtracted in IgorPro software, and the scattering profiles were plotted. For comparison of the self-assembly between PA 1 and monosaccharide 1 (FIG. 4), raw scattering data were plotted without background subtraction and plotted in IgorPro.

SAXS of PA-GF Mixture: To probe the influence of BMP-2 binding on self-assembly of supramolecular nanofibers, PAs 1 and 4 were dissolved to 6.6 mM in saline with 6.6 mM $CaCl_2$, pH 7.2, thermally annealed at 80° C. for 30 min and slowly cooled to room temperature. GFs were prepared at 1.32 mg/mL according to manufacturer's protocol. Solutions of PA and GF were mixed at 10:1 vol. ratio to yield [PA]=6 mM and [BMP-2]=120 µg/mL, incubated overnight at 37° C., and SAXS profiles were obtained using the procedures described above. Also, as control, PAs were mixed with blank buffer appropriate for each GF at equal vol. ratios. Scattering profile from 120 ug/mL GF in saline did not differ from that from blank saline (data not shown). Background subtracted scattering profiles were plotted on a relative scale as a function of the wave vector.

Circular Dichroism: PA samples (5 mM) were thermally annealed as described for Cryo-TEM, and diluted to 25 µm in 0.1×saline with 2 mM $CaCl_2$. Circular dichroism (CD) spectra of the PA samples were measured on a Jasco J-1500 CD spectrophotometer at 25° C. using a 1 mm path length cuvette with the following conditions: scan speed 100 nm/min, bandwidth 1 nm, and averaged 3 traces.

CD of PA-GF Mixture: PAs 1 and 4 (5 mM) were thermally annealed as described for Cryo-TEM. Working solution for CD was prepared by mixing 0.1×saline containing 2 mM $CaCl_2$ with the manufacturer's recommended buffer for each GF at 88:12 by volume. This working solution was used to prepare GF solutions at 11.2 or 2.8 µg/ml. Afterwards, the GF solution was mixed with each PA solution at 9:1 by volume to yield 160 µl, gently mixed, then incubated overnight at 37° C. Following, CD spectra was obtained at 37° C. as described above. The stability of the β-sheet was assessed by plotting the minimum peak at 220 nm.

Zeta Potential Measurements: Zeta ($\zeta$) potential was measured using a Malvern Zetasizer Nano ZS (n=3). PA samples were thermally annealed as described for Cryo-TEM. Following, PAs were diluted to 0.5 mM in DMEM. PA solutions were water-bath sonicated for 1 min prior to zeta potential measurement. Background reading from DMEM alone was subtracted from the final measurements.

Titration Curve: Titration curve of PA was obtained to determine the pKa of the charged side chains. PA was dissolved at 1 mM in saline with 1 mM $CaCl_2$, thermally annealed at 80° C. for 30 min, and cooled to RT. A 1 mL solution was then transferred to an eppendorf tube with a small magnetic stirrer bar, and set on a magnetic stirrer. The PA solution was titrated by incrementally adding 0.5 uL of 0.1 M HCl while allowing sufficient mixing at each step. The pH of the solution was measured using Mettler Toledo FE20 pH meter.

Surface Plasmon Resonance: The binding interactions between PAs (analytes) and growth factors (ligands) were analyzed via surface plasmon resonance (SPR) using a ProteON XPR36 system (Bio-Rad Laboratories). PA samples were thermally annealed as described for Cryo-TEM. PA solutions were spun down, pipetted for homogeneous mixing, and sequentially diluted to appropriate concentrations using Tween buffer (Milli-Q water, 0.05% Tween-20). Lyophilized powders of GFs were reconstituted to 5 µM without any carrier proteins according to the manufacturer's instructions. BMP-2, BMP-4, Shh, VEGF, and FGF-2 were further diluted to 200 nM in ProteOn Acetate Buffer pH 5.5, while FGF-1 was diluted to 200 nM in ProteOn Acetate Buffer pH 4.5. Noggin was diluted to 300 nM in ProteOn Acetate Buffer pH 5.5.

GFs were immobilized on a ProteOn GLC-Chip via amino coupling as described previously, with slight modifications (37). First, the alginate surface was activated with a freshly prepared mixture of 20 mM 1-Ethyl-3-[3-dimethylaminopropyl]carbodiimide hydrochloride (EDC) and 5 mM N-hydroxysulfosuccinimide (Sulfo-NHS) in Milli-Q water (vertical flow cells, 30 µL/min, 3 min). Following, GFs were immobilized on vertical flow cells 1 to 5 by perfusing a freshly prepared 200 nM (or 300 nM) solution over the activated alginate surface (30 µL/min, 5 min). Blank buffer was perfused on vertical cell 6 as a reference. The remaining esters were deactivated with 1 M ethanolamine (30 µL/min, 3 min). The association and dissociation phases were performed at 25° C. in Tween buffer. Prior to each analyte injection, the horizontal flow cells 1 to 6 were regenerated with 10 mM NaOH (100 µL/min, 30 sec) and washed once with Tween buffer (30 µL/min, 3 min). Varied analyte concentrations were injected to horizontal flow cells 1 to 5, with flow cell 6 as a reference (30 µL/min, 5 min), followed by dissociation with Tween buffer (30 µL/min, 10 min). For analysis, SPR sensorgram from the reference flow cell was subtracted from all measurement flow cells. Interaction data were evaluated using the BIAEvaluation 4.1 software. All measurements were performed in triplicates.

Confocal Fluorescence Imaging: PA 1, PA 4, and Cy3-PA were dissolved to 6.6 mM in saline with 6.6 mM $CaCl_2$, pH 7.2. PAs 1 and 4 were each co-assembled with Cy3-PA at 95:5 molar ratio, then thermally annealed at 80° C. for 30 min and slowly cooled to room temperature. Following, PA solutions were mixed with Cy5-BMP-2 (57 µM) at 10:1 vol. ratio to yield [PA]=6 mM and [BMP-2]=5.2 µM, and incubated overnight. For confocal imaging, 20 µl of the solutions containing Cy5-labeled protein and Cy3-Labeled PA nanofibers were coverslipped in IMMU-MOUNT (Termo Scientific) and visualized using a Nikon A1R confocal laser-scanning microscope with GaAsP detectors.

C2C12 Cell Culture: C2C12 mouse myoblasts (ATCC) were maintained in Dulbecco's Modified Eagle's Medium with high glucose and L-glutamine (DMEM, ATCC), supplemented with 100 U/mL of penicillin and 100 μg/mL streptomycin (P/S, Life Technologies) and 10% heat inactivated FBS (Life Technologies), and passaged at 80-90% confluence. Media was changed every 2 days. Passages 3 to 8 were used for experiments. Cells were grown at 37° C., 5% $CO_2$ in a humidified atmosphere. Cells were detached following a 3 minute incubation at 37° C. with 0.05% Trypsin-EDTA (Life Technologies), then resuspended in DMEM (10% FBS). Unless stated otherwise, cells were seeded at 75,000 cells/mL (400 μL/well in a 48-well plate), and allowed to attach for a minimum of 3 hours prior to experiments.

C2C12 Osteoblast Differentiation: PA samples were thermally annealed as described for Cryo-TEM. PA solutions were spun down, pipetted for homogeneous mixing, then diluted to 1 mM with DMEM (no FBS). In a 1.5 mL microcentrifuge tube, PA solutions were further diluted with DMEM (5% FBS), gently vortexed, and appropriate amounts of GFs (20 μg/mL) were added to yield [PA]=125 μM and [GF]=375 ng/mL. For mixing, the microcentrifuge tube was gently inverted several times by hand. Following, cells were treated by adding a 100 μl, of the PA/GF mixture per well (48-well plate), yielding a final 500 μl, differentiation medium with [PA]=25 μM and [GF]=75 ng/mL. For controls, the initial 5 mM PA solution was substituted with either PBS alone (saline) or heparin in PBS at appropriate concentrations. Cells were cultured for 3 days without changing the media, and osteoblast differentiation was assessed.

Alkaline Phosphatase Activity: Alkaline phosphatase (ALP) activity was measured as a marker of osteoblast differentiation (ref. 38; incorporated by reference in its entirety). On day 3, media was removed, and cells were lysed with a 100 μL, of M-PER Mammalian Protein Extraction Reagent (Life Technologies), supplemented with 1×Halt Protease Inhibitor Cocktail (Thermo Fisher Scientific), for 30 minutes on an orbital shaker. A 20 μL, volume of the cell lysate was incubated with 200 μL, of the QUANTI-Blue colorimetric ALP assay (InvivoGen) for 30 minutes to 2 hours at 37° C., in duplicates. The ALP activity was assessed by reading the OD at 630 nm with Cytation3 microplate reader (BioTek). Data were normalized to the respective endogenous DNA levels using Quant-iT PicoGreen dsDNA Assay Kit (Life Technologies). Two separate experiments with 4 replicates each were averaged for statistical analysis.

Alkaline Phosphatase Staining: The presence of ALP was stained using Fast Blue. On day 3, cells were fixed with 4% paraformaldehyde in PBS for 30 seconds, washed once with PBS and stained with Fast Blue for 30 minutes at room temperature. Following, the samples were washed twice with PBS. To prepare the Fast Blue staining solution, napthol AS-MX (10 mg/mL, Sigma Aldrich) was dissolved in a glass vial using DMF and added to a solution of 0.1M Tris-HCl, pH 8.2 containing Fast Blue BB hemizinc salt (1 mg/mL, Sigma Aldrich). The solution was vortexed and filtered immediately prior to staining.

Quantitative RT-PCR: The gene expression levels were determined by real-time, reverse-transcription-PCR using an iQ5 Real-Time PCR Detection System (Bio-Rad). On day 3, total RNAs were extracted from C2C12 cells with TRIzol (Invitrogen), followed by a reverse-transcription step using iScript Reverse Transcription Supermix (Bio-Rad), and finally PCR amplification with iQ SYBR Green Supermix (Bio-Rad). Each 25 μL reaction volume contained 12.5 ng of DNA. Primers for each target gene are as follows: glyceraldehyde-3-phosphate dehydrogenase (GAPDH), forward primer: 5'-TGA AGG TCG GTG TGA ACG GAT TGG C-3' (SEQ ID NO: 4), reverse primer: 5'-CAT GTA GGC CAT GAG GTC CAC CAC-3' (SEQ ID NO: 5); alkaline phosphatase (ALP), forward primer: 5'-GTT GCC AAG CTG GGA AGA ACA C-3' (SEQ ID NO: 6), reverse primer: 5'-CCC ACC CCG CTAT TCC AAA C-3' (SEQ ID NO: 7); and Osteocalcin (OCN), forward primer: 5'-CAA GTC CCA CAC AGC AGC TT-3' (SEQ ID NO: 8), reverse primer: 5'-AAA GCC GAG CTG CCA GAG TT-3' (SEQ ID NO: 9) (IDT) (refs. 21, 39; incorporated by reference in their entireties). PCR conditions were as follows: cDNA denaturation at 94° C. for 5 min, followed by 40 repeated cycles at 94° C. for 45 s, annealing at 55° C. for 1 min, and extension at 68° C. for 1 min. To confirm the specificity of the amplified products, melting curves were performed by cooling samples at 55° C. for 30 s and then increasing the temperature to 94° C. at 0.5° C./sec with continuous fluorescence measurement. Data were normalized to endogenous GAPDH levels using the ΔΔCt method, and then normalized to BMP-2 alone controls. Two separate experiments with 4 replicates each were averaged for statistical analysis.

BMP-2 Stability Assay: C2C12 cells were seeded at 150,000 cells/mL (500 μL/well in a 48-well plate) and incubated overnight. Following, the media was replaced with treatment media (75 ng/mL BMP-2 in the presence/absence of PA 1, PA 4, and monosaccharide 1. The media was collected at 0, 3, 9, and 24 h and stored at −80° C. prior to BMP-2 quantification. In addition, the cell monolayers were lysed at the indicated time with a 100 μL of M-PER Mammalian Protein Extraction Reagent, supplemented with 1×Halt Protease Inhibitor Cocktail, and also stored at −80° C. prior to BMP-2 quantification. The amount of BMP-2 present in the media and cell extracts was assayed using a BMP-2 Quantikine ELISA kit (R&D Systems) according to the manufacturer's specifications.

BaF3-FR1C Cell Proliferation Assay: Upon reception of a frozen vial, BaF3-FR1C cells were cultured and expanded in growth media as recommended (40). The cells were grown in RPMI1640 medium with 2 mM L-glutamine (Thermo Fisher) containing 10% newborn bovine calf serum (Thermo Fisher), 0.5 ng/mL of recombinant mouse IL-3 (Peprotech), 600 μg/mL of G418 sulfate (Thermo Fisher), 50 nM of 2-mercaptoethanol (Thermo Fisher), and 100 unit/mL penicillin and 100 μg/mL streptomycin (Thermo Fisher) at 37° C., 5% CO2. The medium was changed every 2 days. Experiments were performed using with 1-3 week old passaged cells. The BaF3-FR1C cells were first assessed with the CyQUANT direct cell proliferation assay (Thermo Fisher), but no change in fluorescent signal was observed from a 0 to 2 day old culture in growth conditions although the growth was evident under the microscope. Hence, the CellTiter 96 AQueous One Solution Cell Proliferation Assay (Promega, #G3581) was used, and a steady absorbance increase was observed after 1 and 2 days of BaF3-FR1C cells in growth media with 5,000-20,000 cells/well in a 96-well plate. For assays testing the effect of heparin and glycopeptide nanofibers FGF-2 induced proliferation, 10,000 cells/well were plated in 50 μl of growth media without G148 sulfate and recombinant mouse IL-3 (NT media) in a 96-well plate. We then added a 2×concentrated mixture of FGF-2 with heparin or glycopeptide nanofibers in the same NT media. After 2 days in culture, the 20 μl of the CellTiter 96 AQueous One Solution Cell Proliferation Assay was added to each well and the plate was incubated at 37° C. for 1-4 hours. The absorbance was read at 490 nm in a Cytation 3 instrument (BioTek) and cell growth was compared to cells in NT media. Each sample was run in quadruplicate and the experiment was run twice.

Anticoagulation Assay: PA 1 was dissolved to 5 mM in saline with 5 mM CaCl$_2$, pH 7.2, thermally annealed at 80° C. for 30 min and slowly cooled to room temperature. The PA solution was spun down, pipetted for homogeneous mixing, and diluted to 0.25, 2.5, 25, and 100 µM in saline with 2 mM CaCl$_2$). The anticoagulant activities of PA 1 and heparin were assessed by monitoring the activity of Factor Xa, a coagulation cascade enzyme inhibited by heparin-activated antithrombin. The assay was performed using the COATEST Heparin Kit (Chromogenix) according to the manufacturer's instructions. Values were represented as the relative bioactivity of Factor Xa when compared to treatment group treated with saline only.

Rat Posterolateral Lumbar Intertransverse Spinal Fusion: The study was approved by and conducted in line with the Institutional Animal Care and Use Committee (IACUC) policies and procedures. Forty female Sprague-Dawley rats at ages 12-16 weeks were utilized. Animals were assigned to the following treatment groups: 1) 100 ng BMP-2, n=8; 2) 100 ng BMP-2 with PA 4 nanofibers, n=12; and 3) 100 ng BMP-2 with PA 1 nanofibers, n=12. The denoted BMP-2 dose refers to total growth factor amount implanted via two absorbable collagen sponges per animal. For instance, in the 100 ng BMP-2 control group, two collagen sponges (1.75× 0.5×0.5 cm) were each impregnated with 50 ng BMP-2 in 100 uL saline containing 6 mM CaCl$_2$, then implanted adjoining the L4-L5 transverse processes on either side of the spine. For PA groups, 100 uL of PA solutions (6 mM) were used in place of saline.

PAs 1 and 4 were dissolved to 6.6 mM in sterile saline with 6.6 mM CaCl$_2$, thermally annealed at 80° C. for 30 min and slowly cooled to room temperature. PA solutions were spun down, pipetted for homogeneous mixing, then mixed with BMP-2 at 10:1 vol. ratio to yield 6 mM PA with appropriate BMP-2 concentrations.

Surgical Procedures: Rats were maintained on a heating pad under continuous anesthesia with an isoflurane inhalational anesthetic delivery system, and they were monitored by an assistant for cardiac or respiratory difficulties throughout the procedure. Utilizing a previously-described surgical technique (refs. 23, 41; incorporated by reference in their entireties), the L4 and L5 transverse processes were exposed, irrigated with sterile gentamicin/saline solution, the superficial cortical layer decorticated with a high-speed burr, then collagen sponges with appropriate treatments were implanted bilaterally in the paraspinal musculature between the transverse processes. Afterwards, the fascia and skin incisions were closed, and rats were housed in separate cages.

Manual Palpation: Fusion was assessed via manual palpation following euthanasia at 8 weeks post-surgery. Spines were scored by three blinded observers using a previously established scoring system: 0=no bridging; 1=unilateral bridging; and 2=bilateral bridging (23, 41). To assess fusion rate, spines that received an average score of 1.0 or greater were considered successfully fused.

Micro-Computed Tomography: Synchrotron micro-computed tomography (µCT) was performed on representative samples at station 2-BM of the APS (42, 43). Due to the size constraint of the µCT set-up, harvested spines were sagittally cut along the midline of the vertebrate body, using a slow-speed diamond saw (ref. 43; incorporated by reference in its entirety). Data were acquired with 27 keV photons, projections were recorded every 0.12° over 180°, and reconstruction was on a 2,048×2,048 grid with isotropic 1.45 µm voxels using TomoPy (44). For each sample, five overlapping regions of interest (1,300 slices each) were merged into one continuous stack of 5,980 slices using ImageJ. Volume renderings were obtained using 3D Viewer in ImageJ, and the sagittal digital section through the fusion mass was obtained using Orthogonal Views and Volume Viewer in ImageJ.

Example 3

Results

Figure 3:
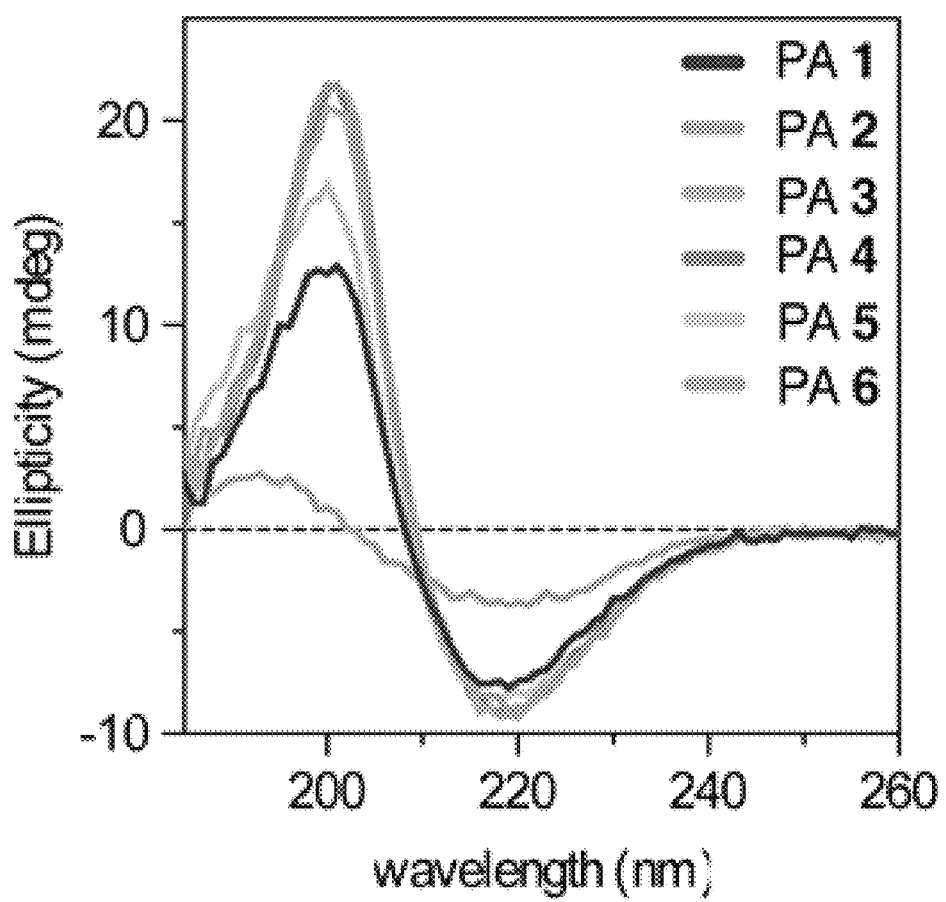
FIG. 3. Circular dichroism (CD) spectra of PAs 1-6. All six PAs show the beta-sheet secondary structure, as indicated by the negative peak between 216 nm and 222 nm.
Figure 4A:
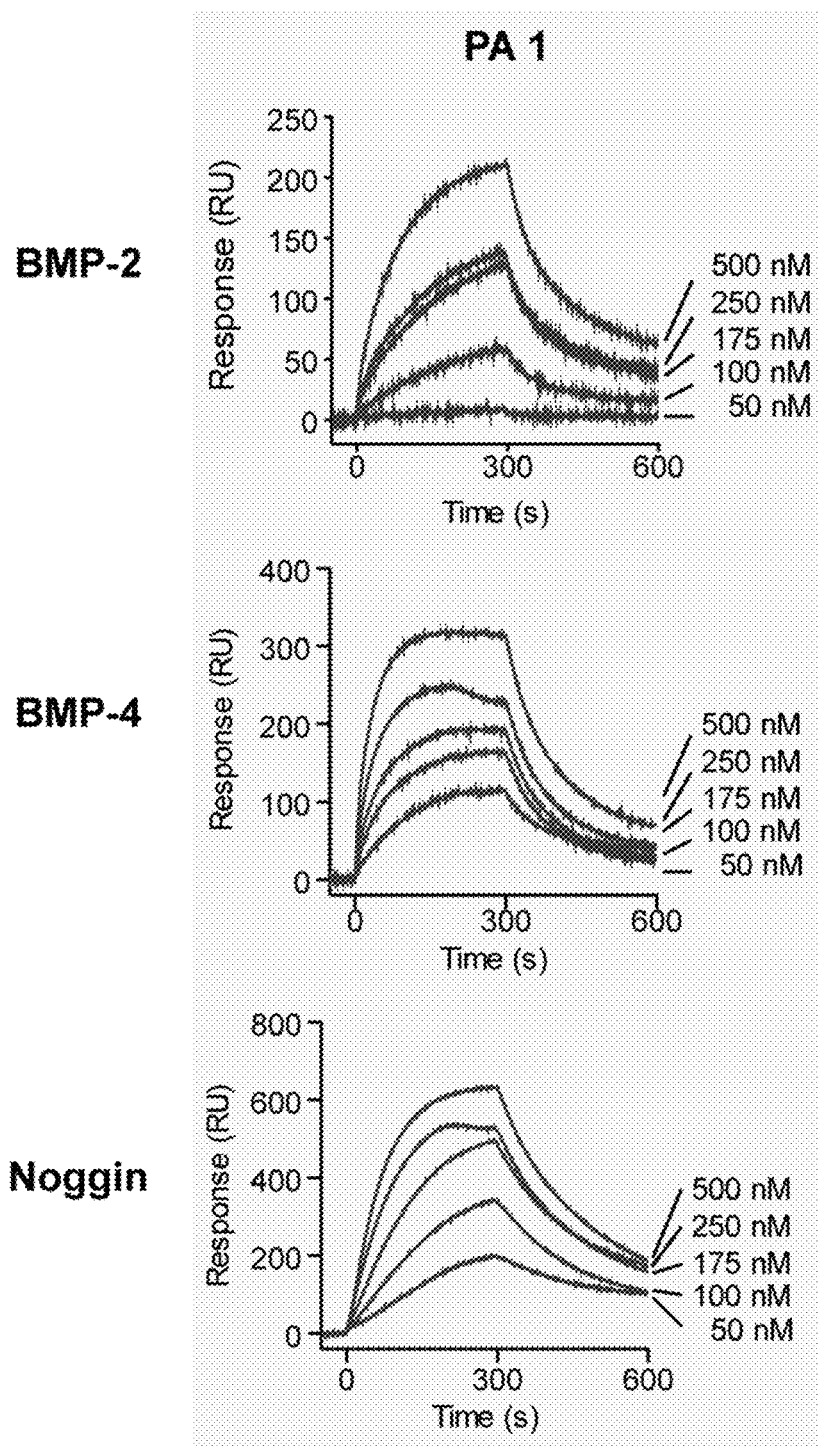
FIGS. 4A-D. Glycomimetic assemblies binding to GFs, measured by surface plasmon resonance (SPR) analysis. GFs or the GF inhibitor noggin were immobilized on the alginate/Au SPR surface, and the following analytes (50-500 nM) were injected for 300 s to monitor the association: (A) trisulfated PA 1, (B) nonsulfated PA 4, (C) trisulfated monosaccharide 1 lacking the PA backbone, and (D) heparin. After 300 s, blank buffer was injected to monitor dissociation.
Figure 4A:
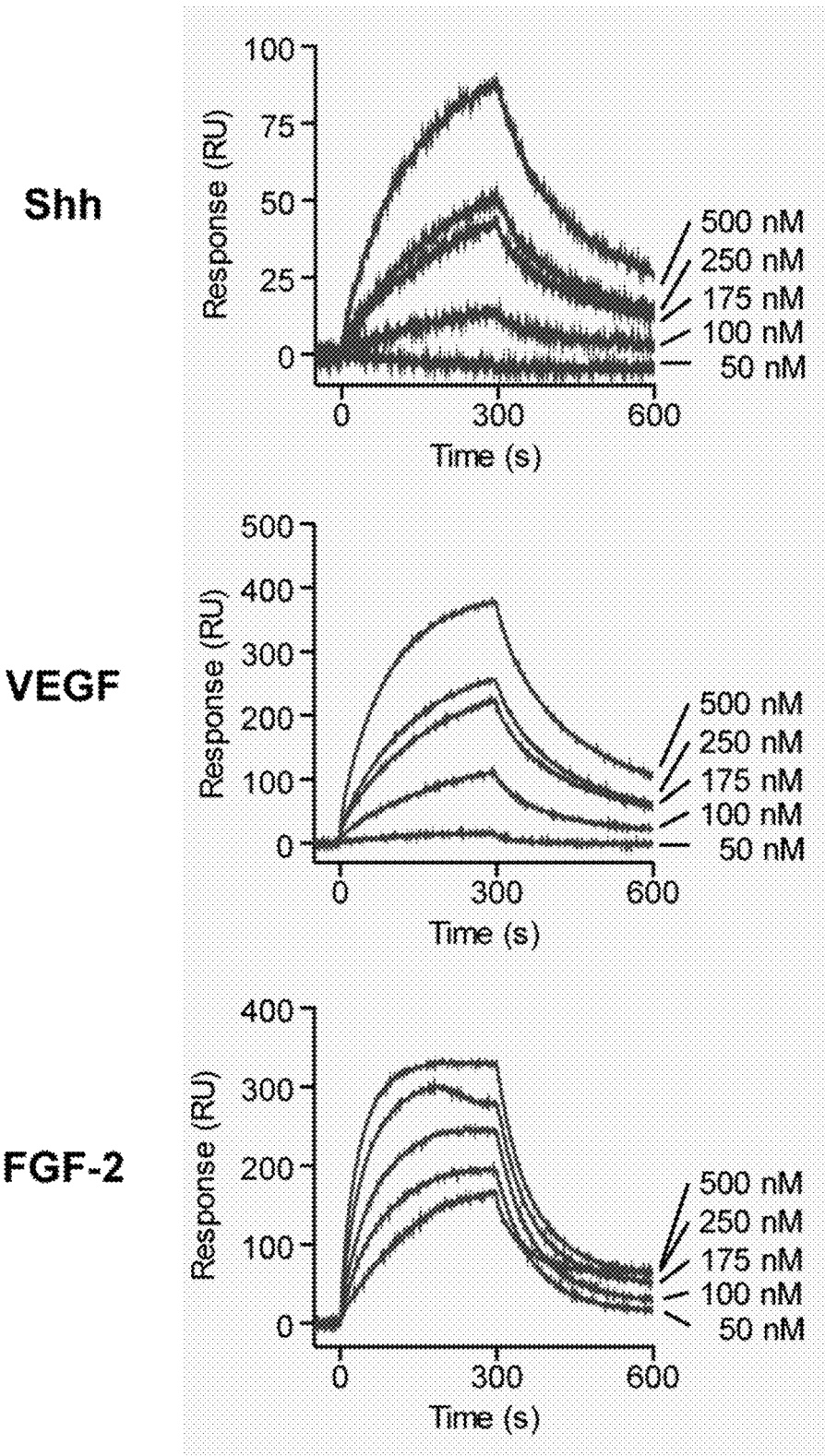
Figure 4B:
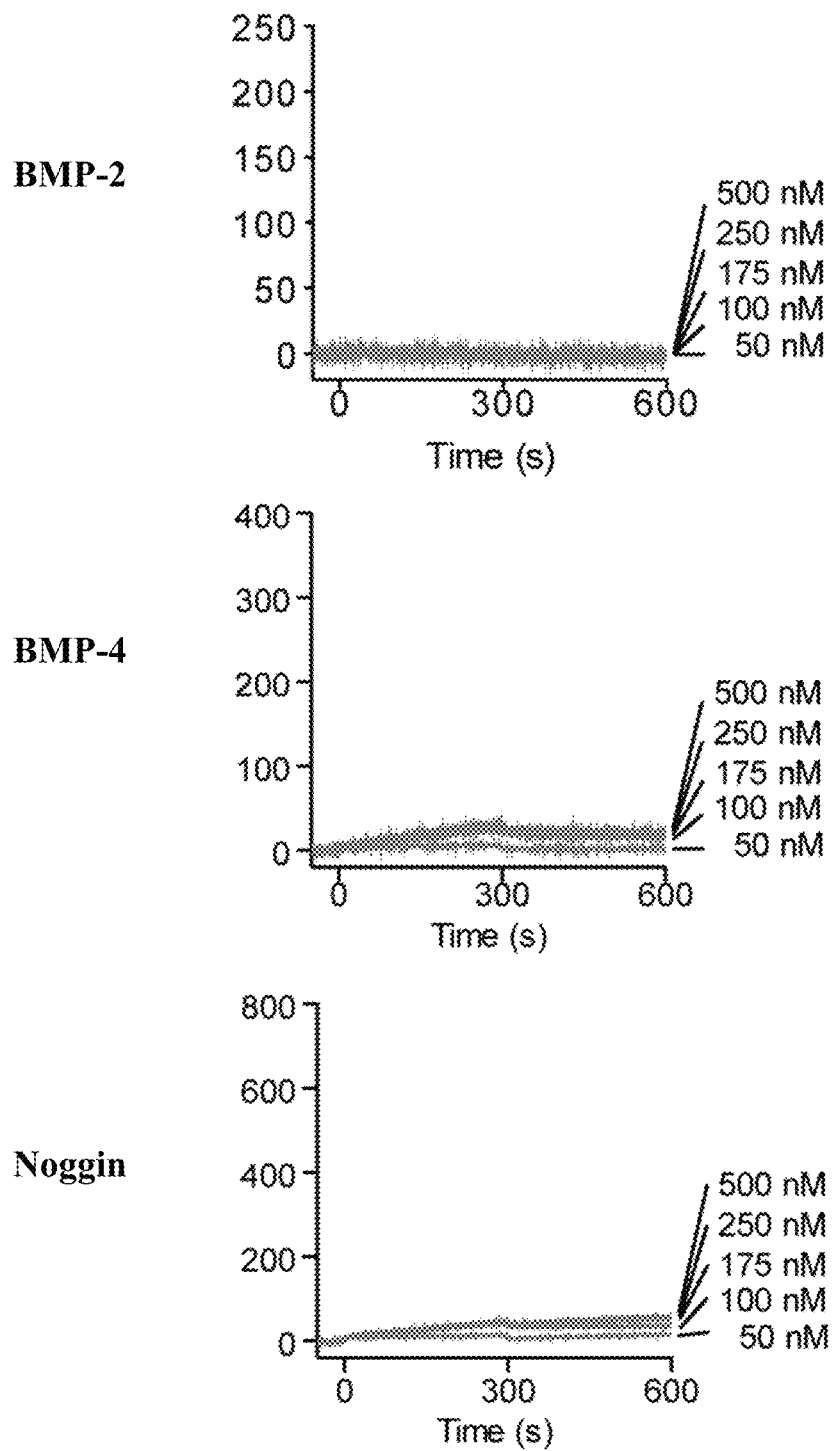
Figure 4B:
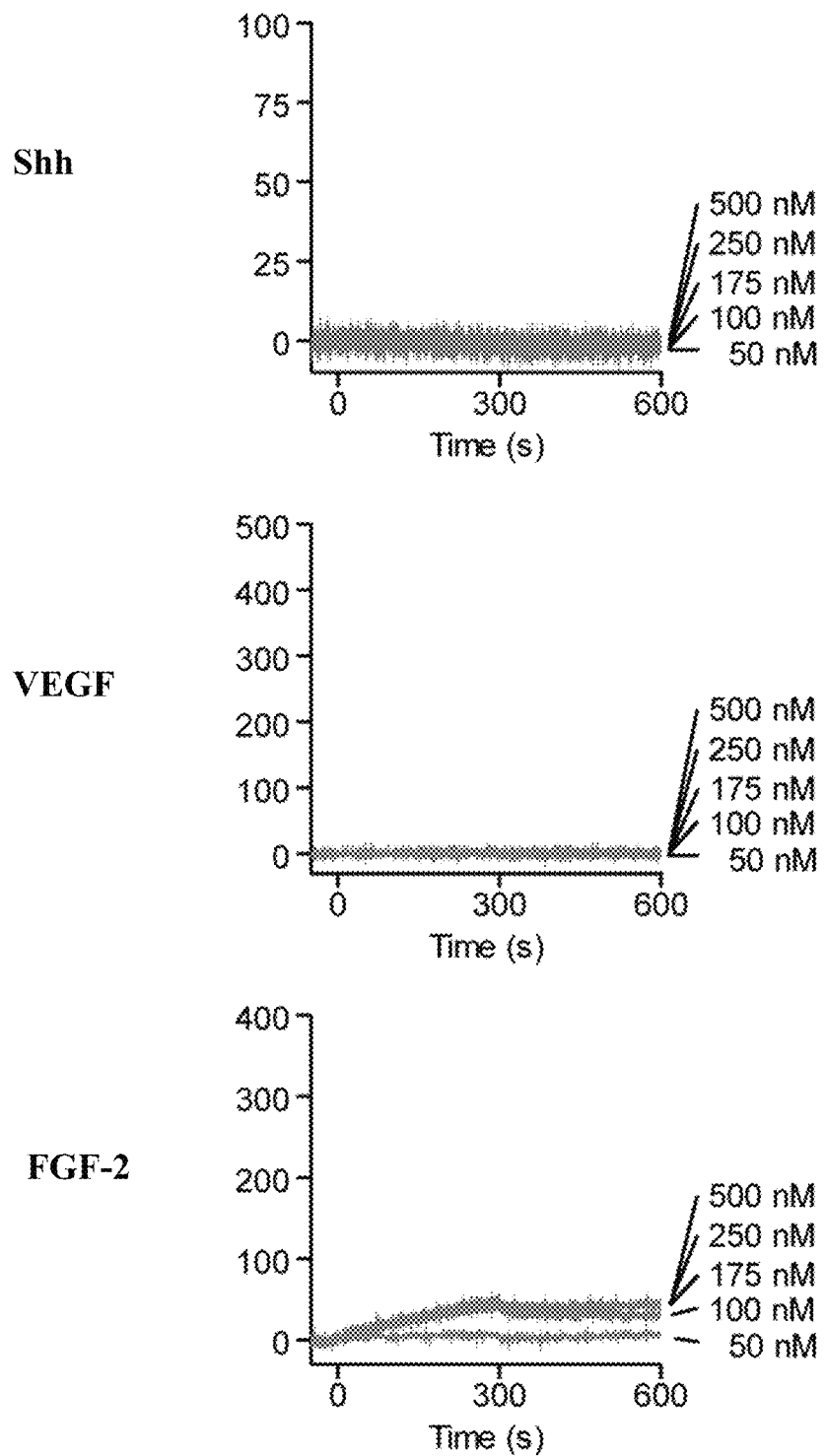
Figure 4C:
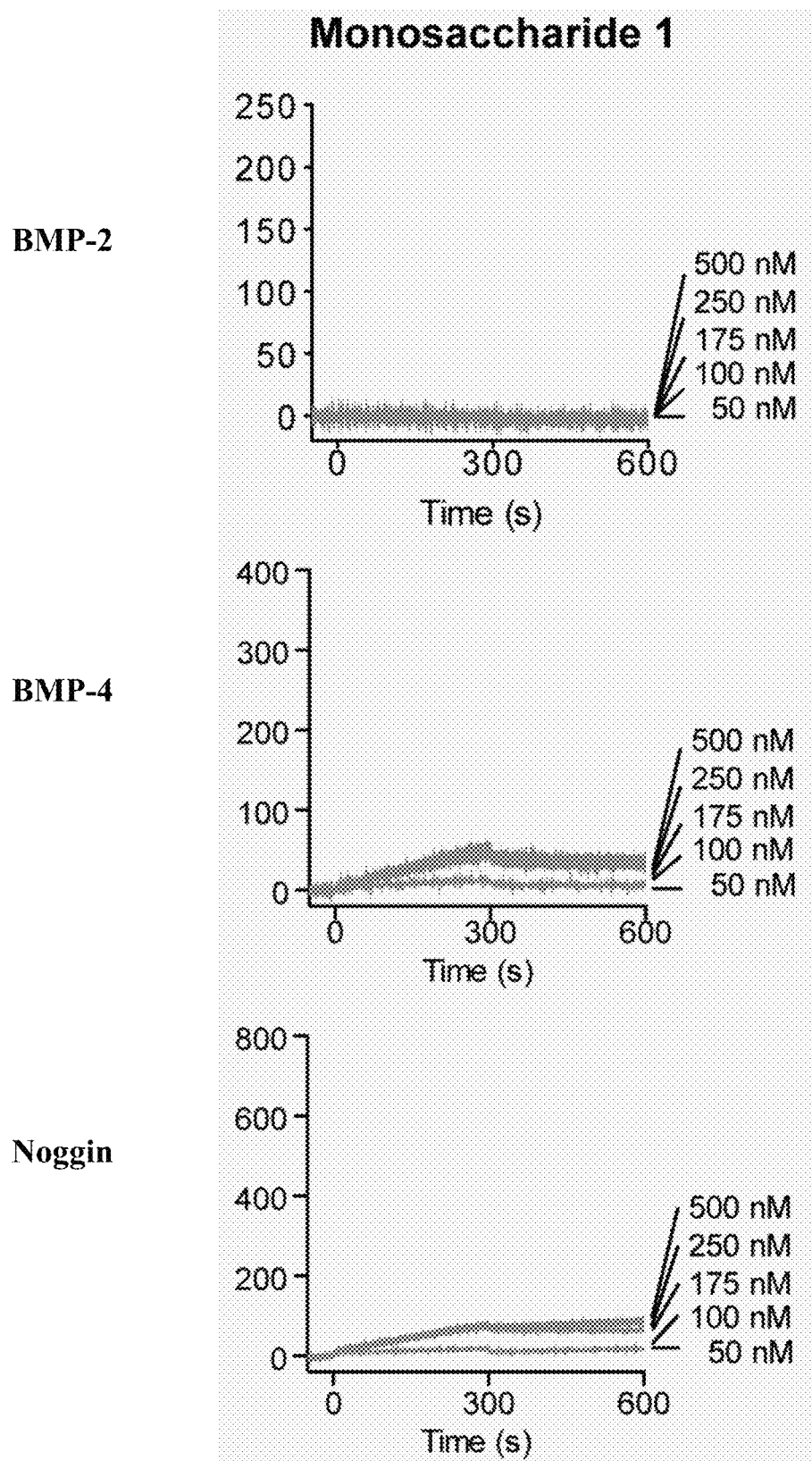
Figure 4C:
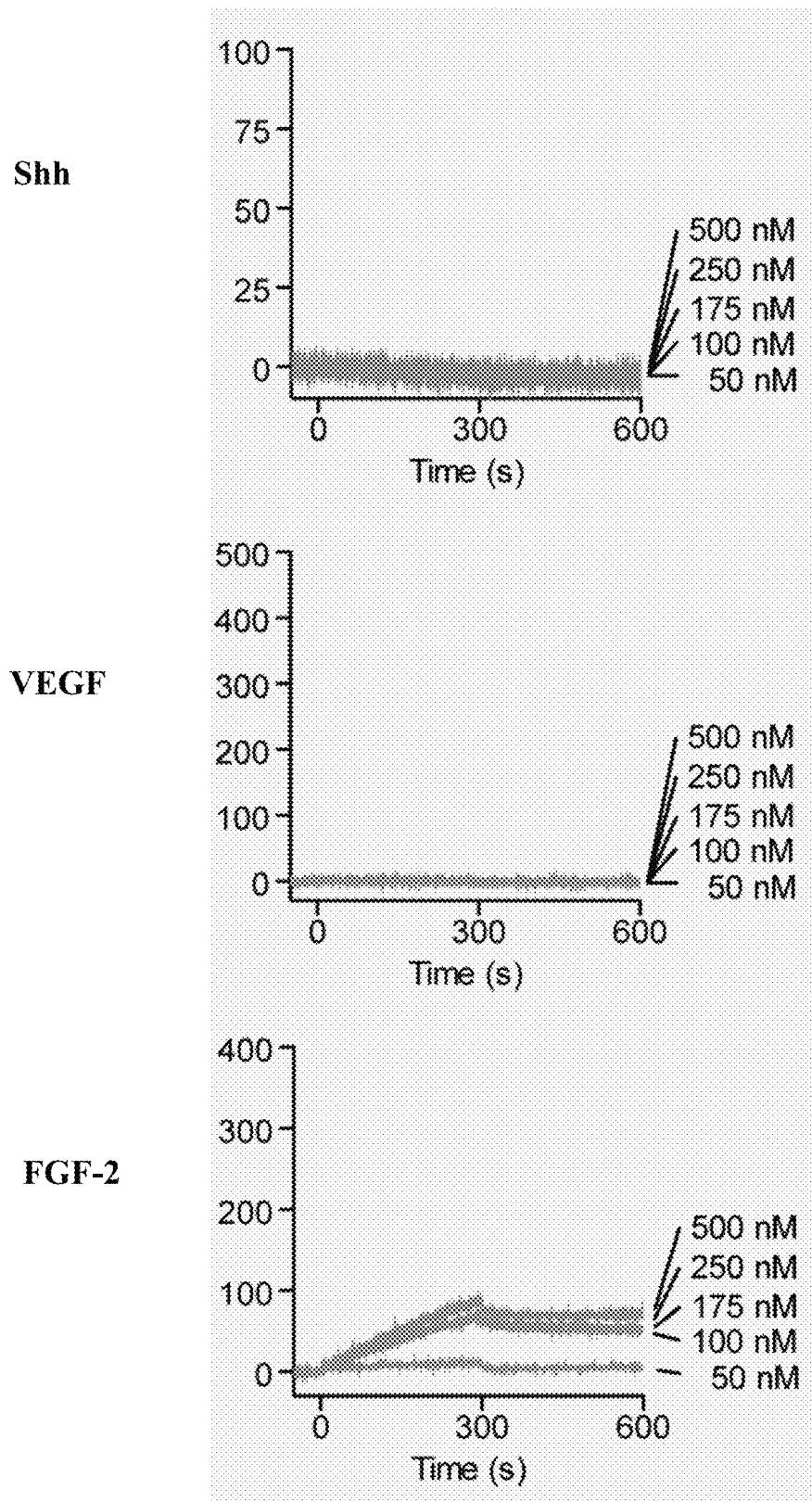
Figure 4D:
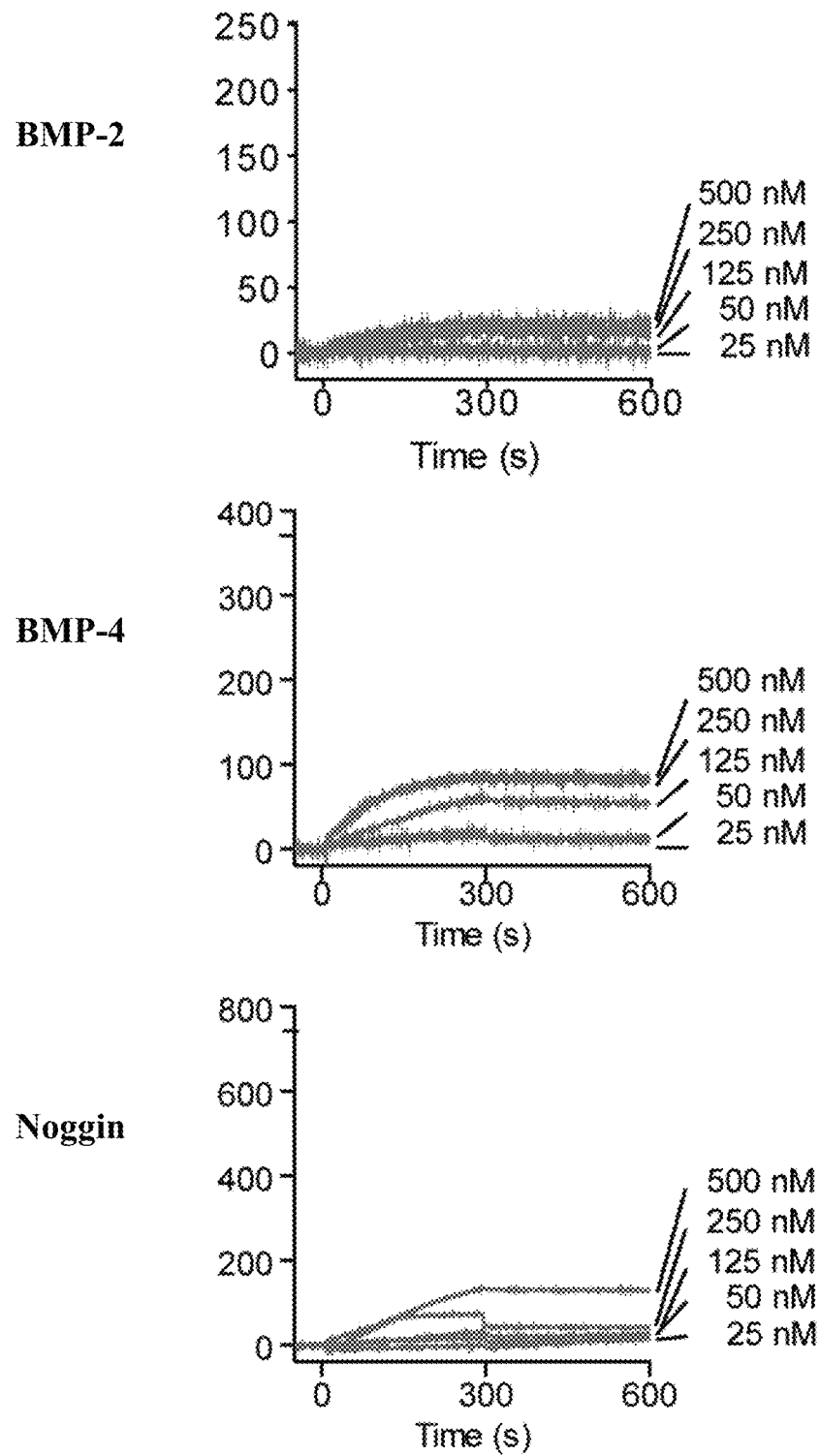
Figure 4D:
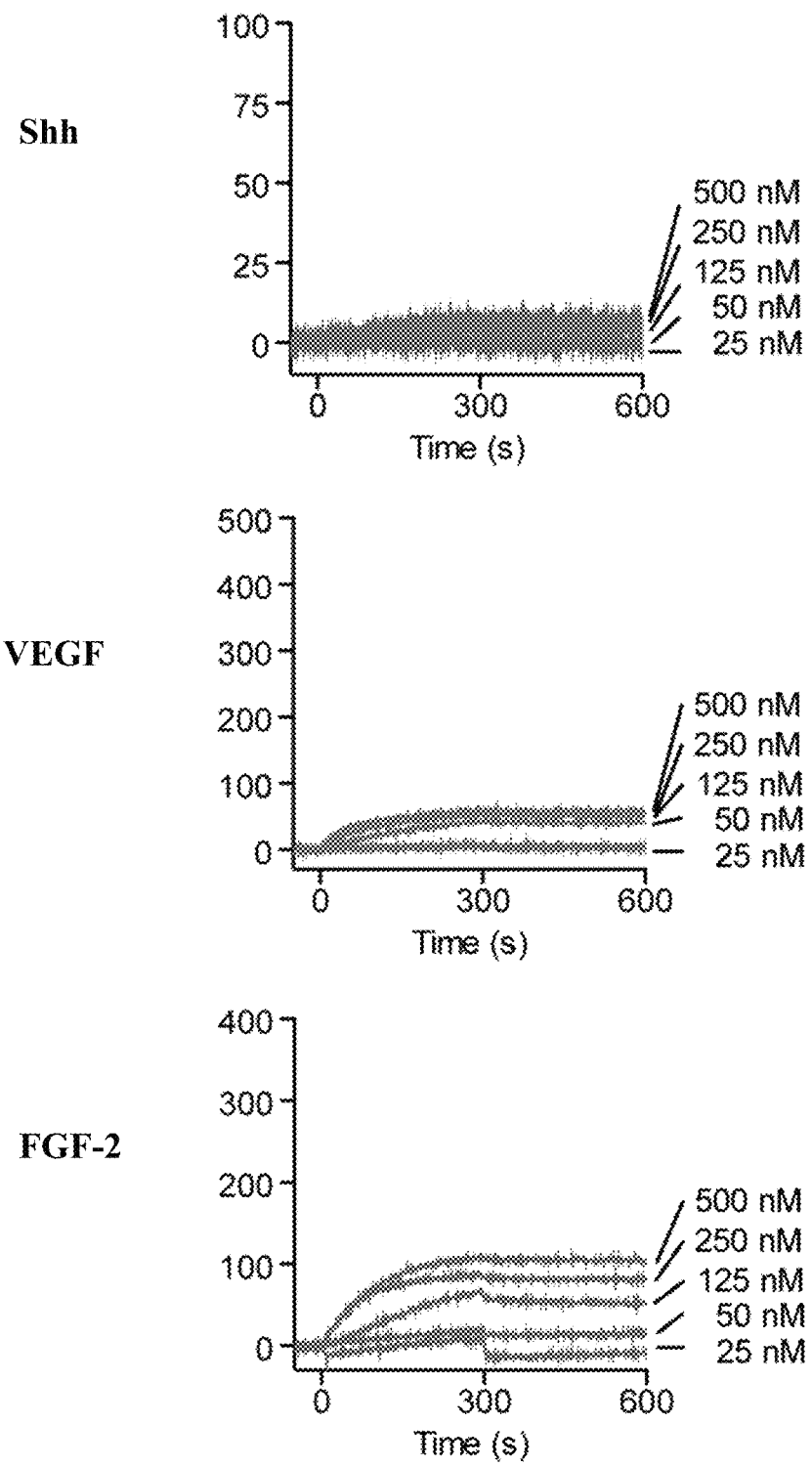

Experiments conducted during development of embodiments herein to evaluate the heparin mimetic supramolecular GAGs, in which synthetic monosaccharides are displayed on the surface of a nanoscale fiber. The internal structure of these nanofibers was built by self-assembly of peptide amphiphiles (PAs), which form supramolecular polymers that mimic extracellular matrix filaments (refs. 6, 7; incorporated by reference in their entireties). Specifically, PAs were glycoconjugated via copper(I)-catalyzed alkyne-azide cycloaddition (CuAAC) (ref. 8) with a series of azido functionalized monosaccharides: trisulfated 3,4,65-N-acetyl glucosamine (3,4,6S-GlcNAc) (PA 1), monosulfated 6S-GlcNAc (PA 2), monocarboxylated glucuronic acid (GlcA) (PA 3), and uncharged GlcNAc (PA 4) (FIG. 1A). The Cu catalyst was removed from synthesized molecules, leaving only trace amounts of Cu (~21 ppb) which is lower than the average concentration in blood (1.1 ppm) (ref. 9; incorporated by reference in its entirety). A representative cryogenic transmission electron micrograph (cryo-TEM) revealed the self-assembly of the glycopeptide amphiphiles into nanofibers at concentrations of 25 µM (FIGS. 1B and 2A). Small-angle X-ray scattering (SAXS) profiles from PAs 1-6 exhibited a slope of −1 in the low-q range, which is indicative of the formation of high-aspect-ratio filaments in solution (FIG. 1C). Also, the scattering minima in the range of q=0.06 to 0.07 Å$^{-1}$ correspond to diameters of 8.9 to 10.5 nm, comparable to those observed in cryo-TEM images. The formation of these filaments is well known to involve hydrophobic collapse of aliphatic tails and β-sheet formation (ref. 10; incorporated by reference in its entirety) among peptide segments (FIG. 3). Zeta potential measurements revealed that trisulfated PA 1 exhibited the highest net negative charge relative to PAs 2-4 (FIG. 1D), indicating that the monosaccharides are exposed on the surface of the self-assembled nanofibers.

Figure 2B:
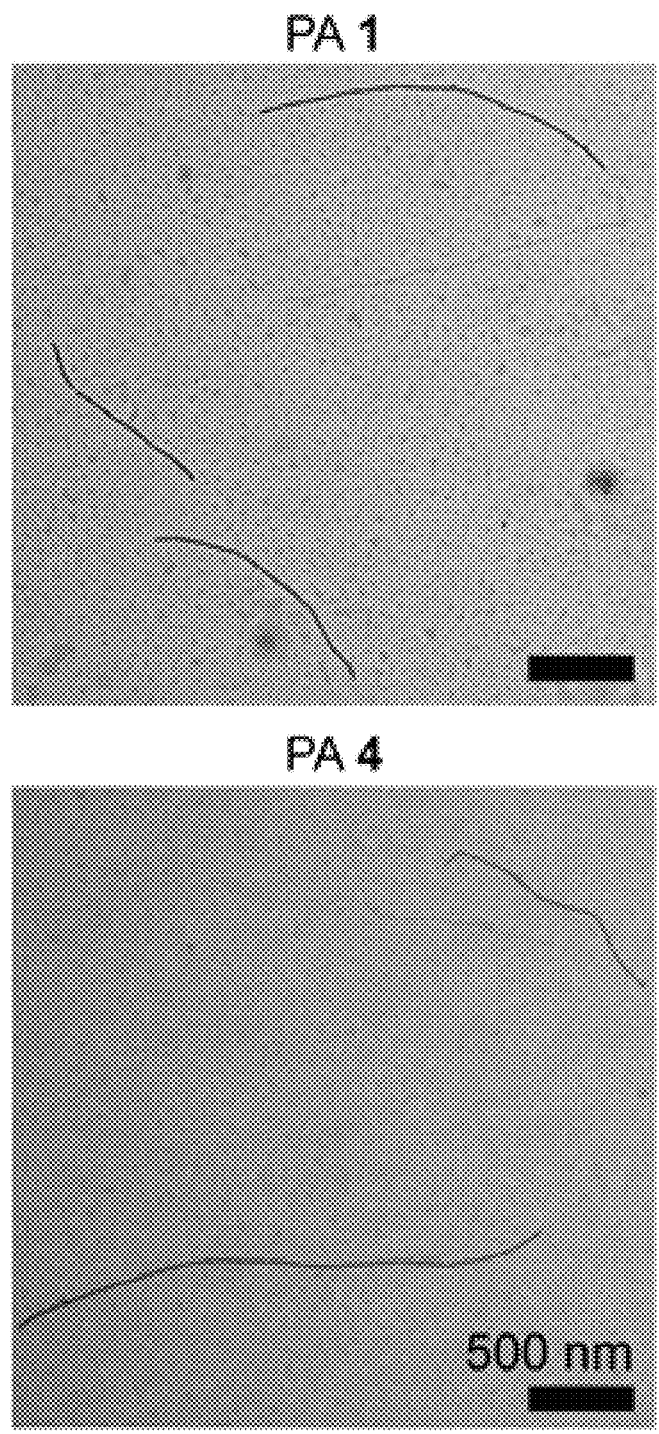

Using surface plasmon resonance (SPR) spectroscopy, the binding capacity of the supramolecular GAGs to seven biologically important heparin binding GFs was evaluated: BMP-2 (ref. 11; incorporated by reference in its entirety), BMP-4 (ref. 12; incorporated by reference in its entirety), noggin (ref. 13; incorporated by reference in its entirety), Sonic hedgehog (Shh) (ref. 14; incorporated by reference in its entirety), VEGF (ref. 15; incorporated by reference in its entirety), FGF-1 (ref. 16; incorporated by reference in its entirety), and FGF-2 (ref. 17; incorporated by reference in its entirety) (Table 1). GFs were covalently immobilized on an alginate surface, and the glycosylated PAs and other control analytes were injected to measure binding. Since sulfation of heparin is crucial for its interaction with GFs used (ref. 2; incorporated by reference in its entirety), the protein-binding behavior of assemblies comprised of trisulfated PA 1 was compared to those of nonsulfated PA 4. PA 1 nanofibers (50-500 nM, see TEM in FIG. 2B) exhibited a strong concentration-dependent binding to all of the GFs, whereas PA 4 nanofibers exhibited negligible binding (FIGS.

Figure 5:
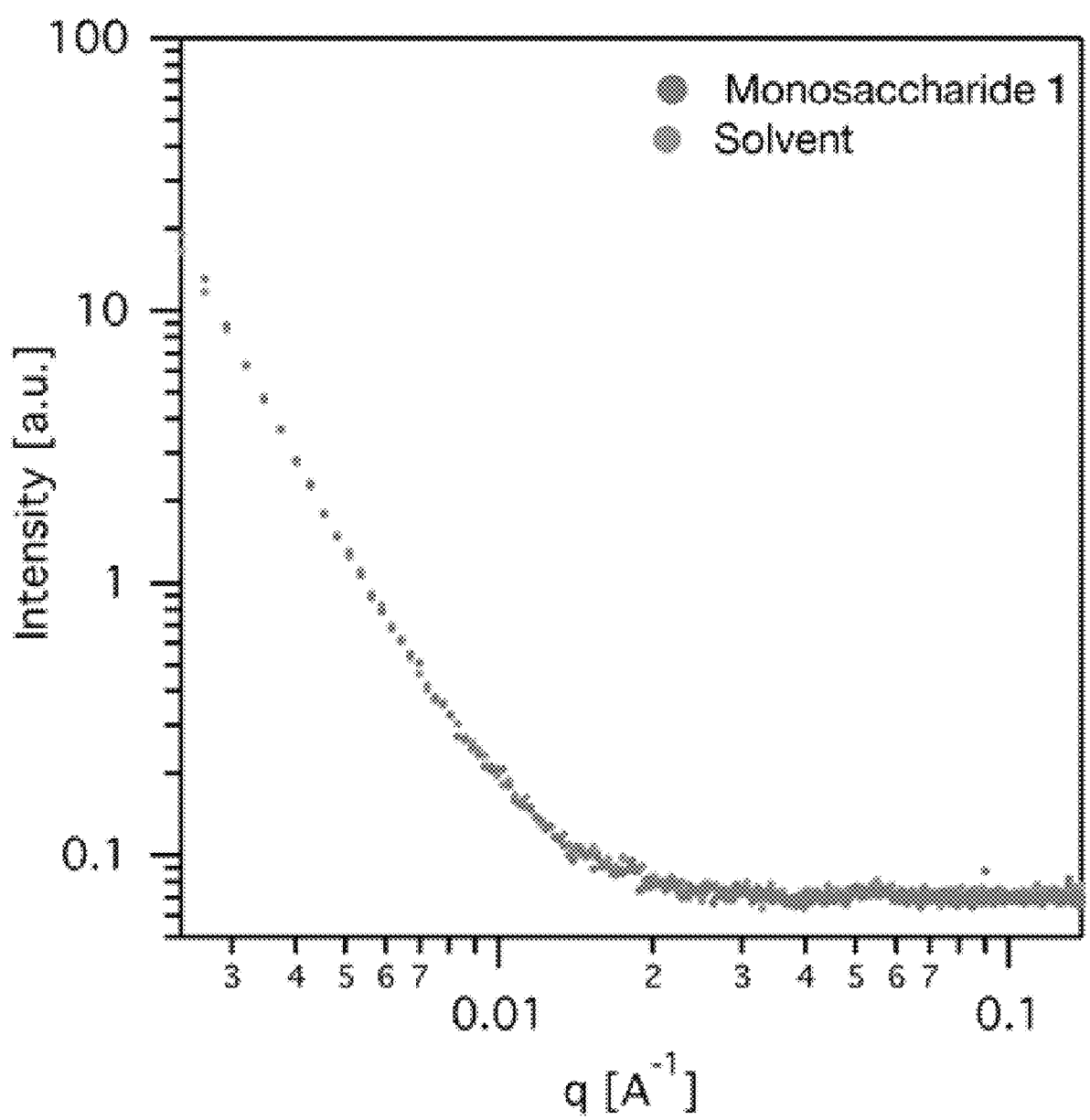
FIG. 5. SAXS data showing the raw scattered intensity without background subtraction versus the scattering vector q (log-log plot) for monosaccharide 1 (6 mM), as well as blank saline (solvent).
Figure 7A:
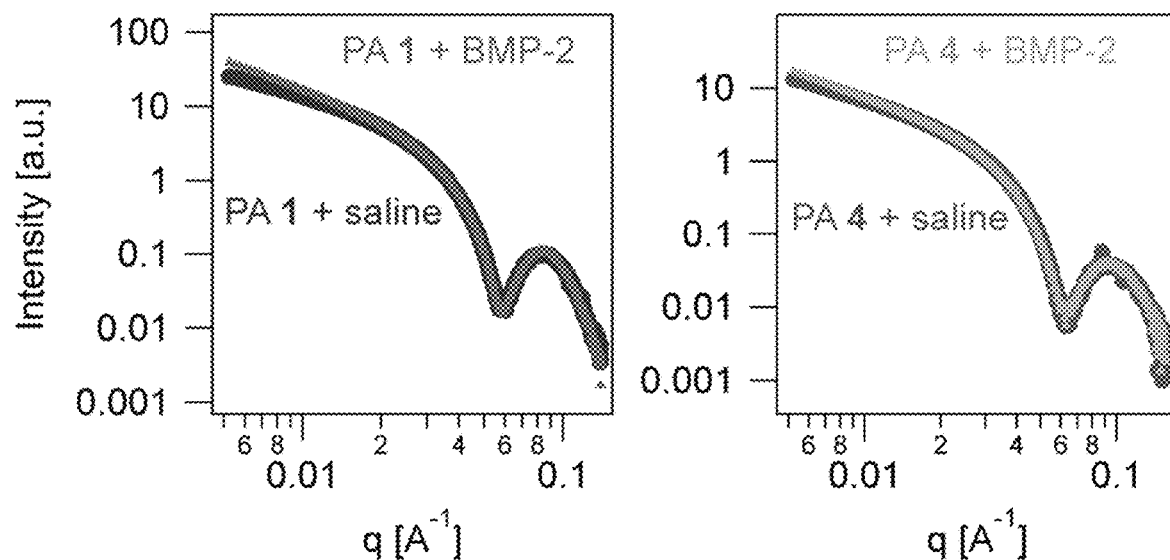
FIGS. 7A-G. Structural analysis of glycopeptide nanofiber-growth factor binding. SAXS data showing background subtracted scattered versus scattering vector q (log-log plot) for PA 1 and PA4 nanofibers (6 mM) in the absence or presence of the following GFs or GF inhibitor (120 μg/mL): (A) BMP-2 (4.6 μM), (B) BMP-4 (5 μM), (C) noggin (6 μM), (D) Shh (2.5 μM), (E) VEGF (3.1 μM), (F) FGF-1 (7.1 μM), and (G) FGF-2 (6.9 μM). PA to GF ratio was selected to match that of confocal fluorescent imaging experiments.
Figure 7B:
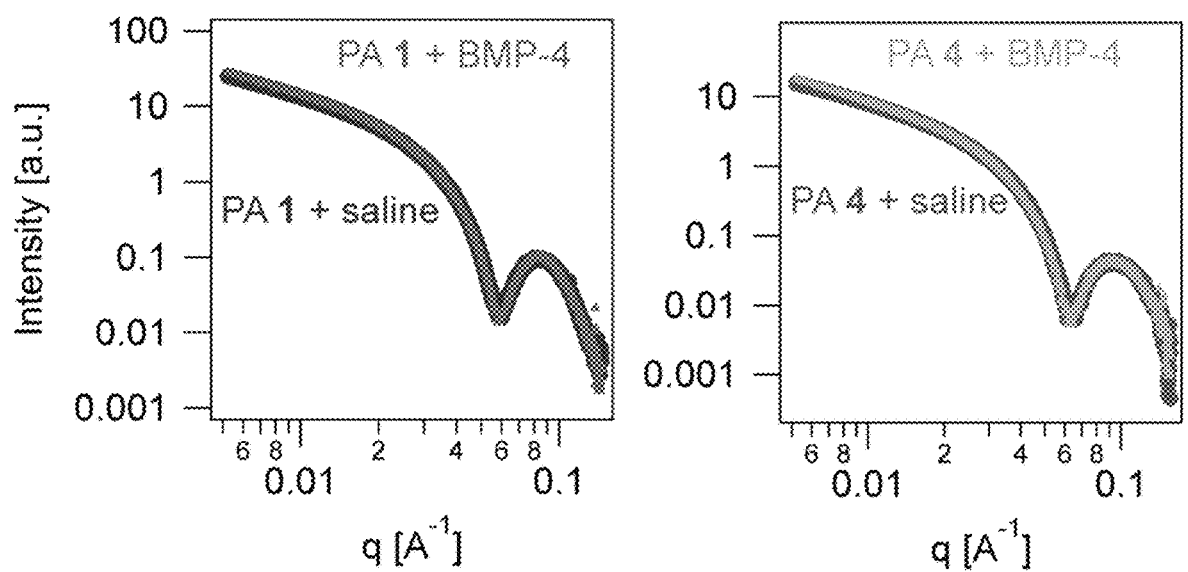
Figure 7C:
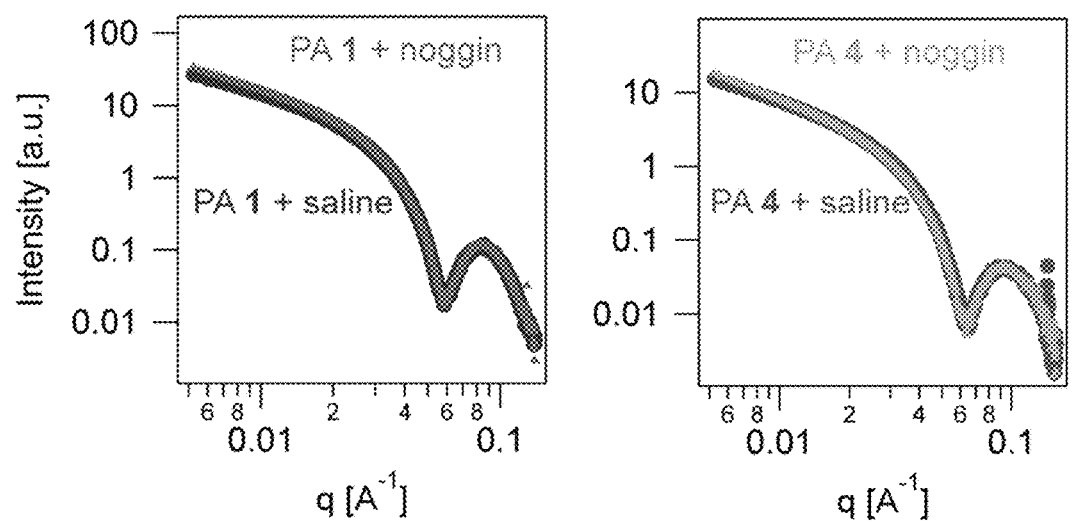
Figure 7D:
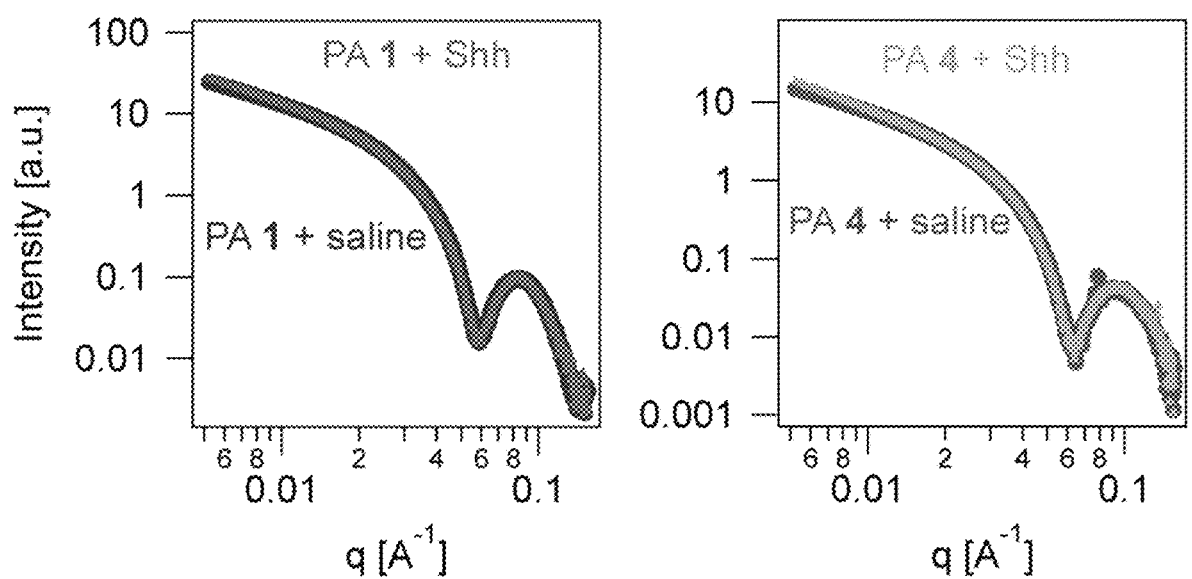
Figure 7E:
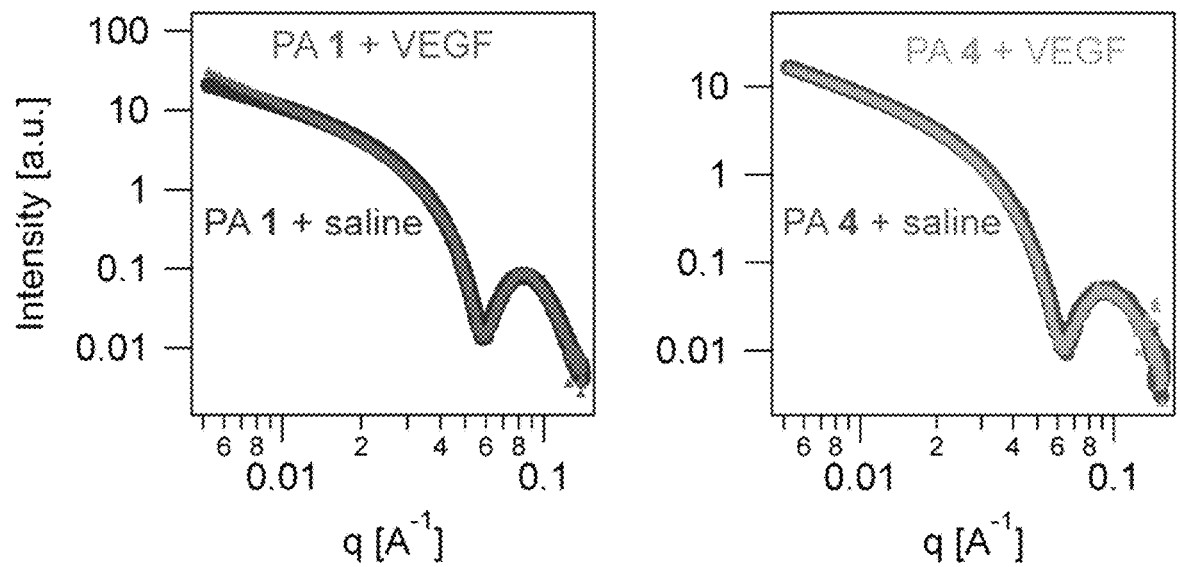
Figure 7F:
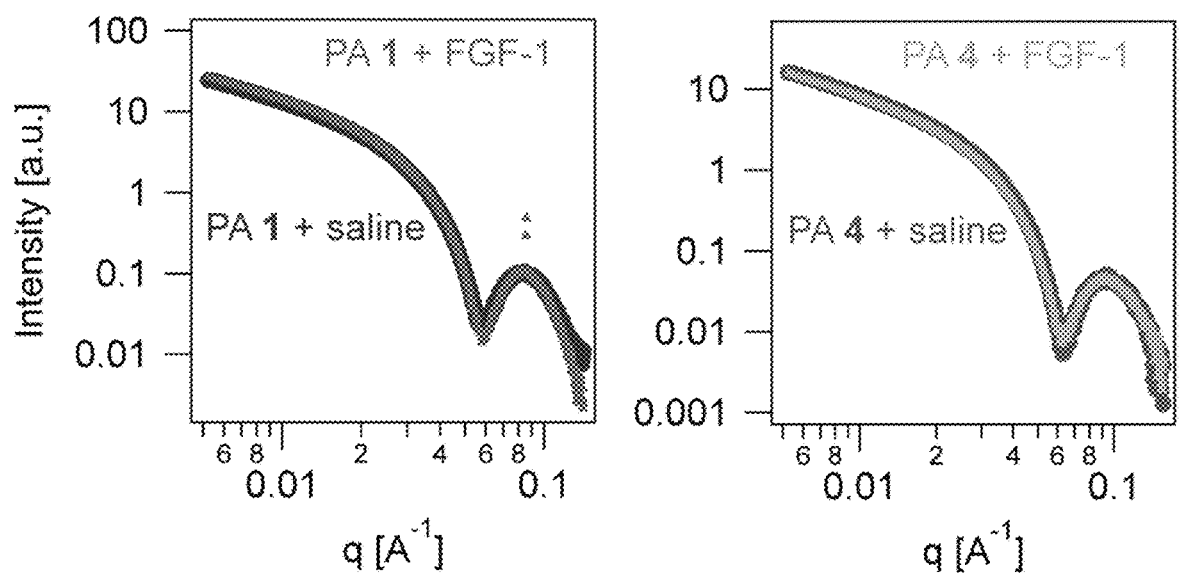
Figure 7G:
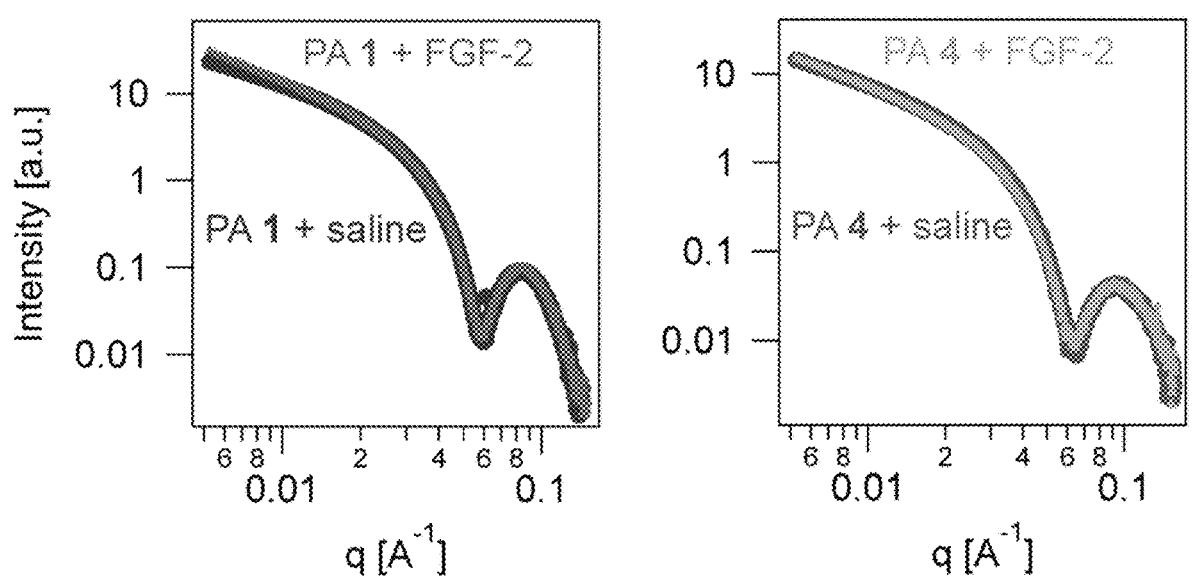
Figure 8A:
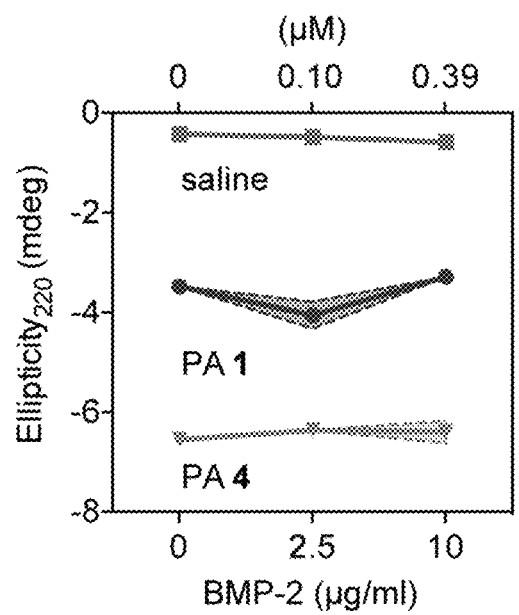
FIGS. 8A-G. CD ellipticity at 220 nm of PAs 1 and 4 (0.5 mM) or blank saline in the absence or presence of seven heparin binding proteins: (A) BMP-2, (B) BMP-4, (C) noggin, (D) Shh, (E) VEGF, (F) FGF-1, (G) and FGF-2. The appropriate GF concentrations are shown in the upper and lower-axes. The initial ellipticity values for each PA are different due to the presence of the appropriate buffer for each GF (10.8% by volume). PA to GF ratios were selected to cover the range of ratios used in characterization, in vitro, and in vivo experiments throughout the study.
Figure 8B:
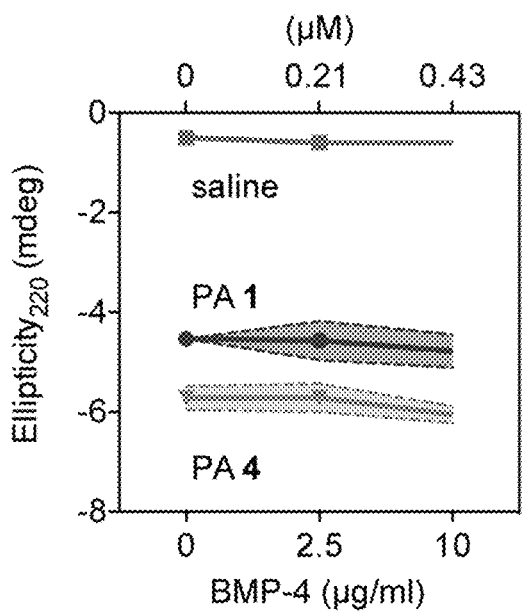
Figure 8C:
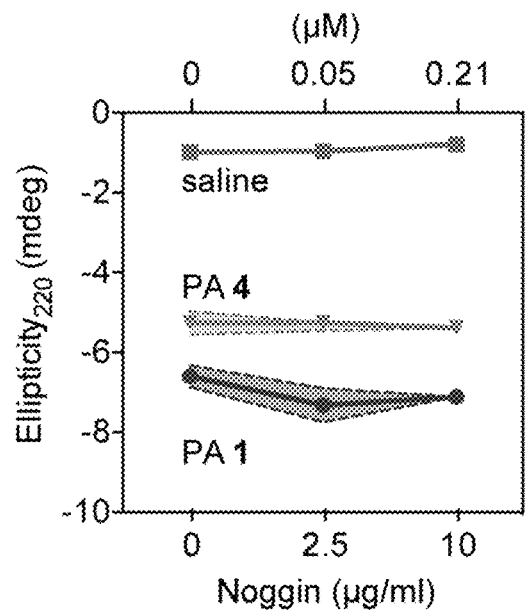
Figure 8D:
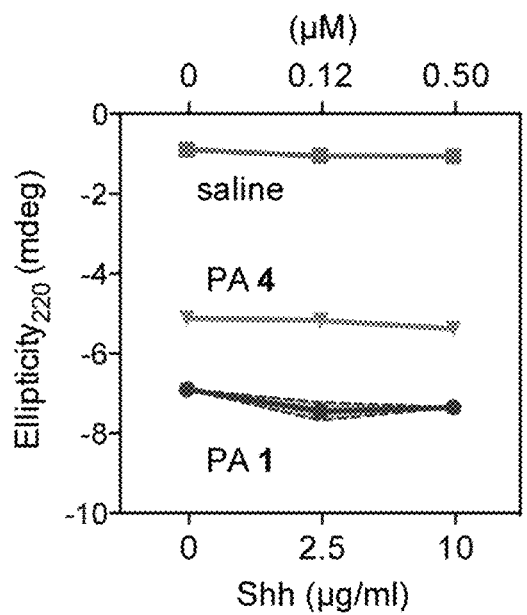
Figure 8G:
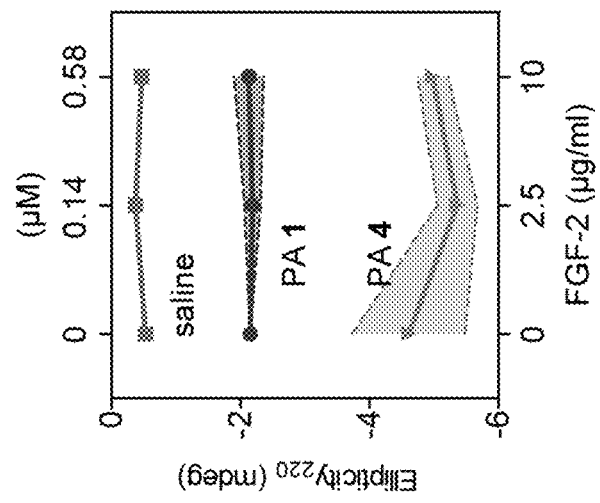
Figure 8F:
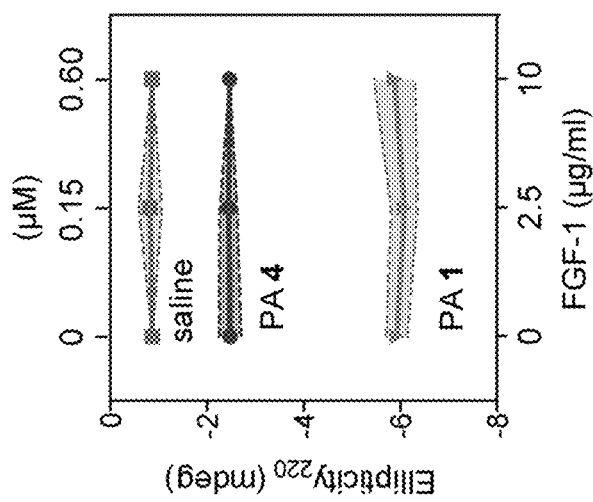
Figure 8E:
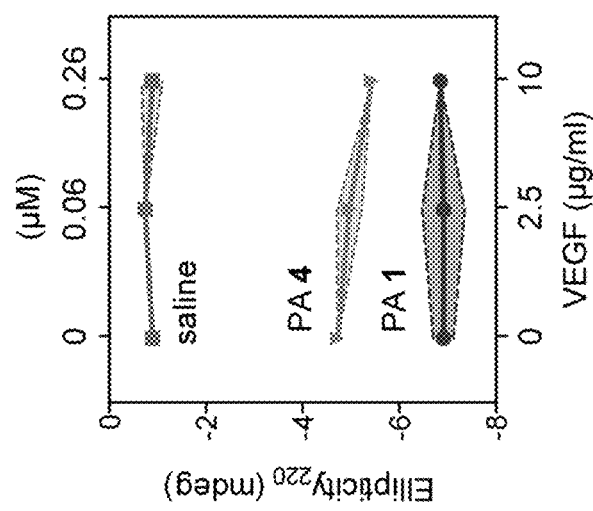

4A-B). This indicates that the high degree of sulfation in the monosaccharides is vital for the strong binding by PA 1. It was also found that the azide-derivative of trisulfated monosaccharide 1 essentially does not bind to the GFs (FIG. 4C), highlighting the importance of the multivalent interactions afforded by assemblies of PA 1 (refs. 18, 19; incorporated by reference in their entireties). In fact, the SAXS curve of the monosaccharide solution is identical to that of the dissolving buffer, demonstrating the absence of any significant supramolecular structure (FIG. 5). Furthermore, heparin only showed moderate binding to the GFs (FIG. 4D), but to a much lesser extent than PA 1 nanofibers. It is contemplated that the noncovalent supramolecular assemblies present a large surface of the highly packed sulfated saccharides to better interact with GFs relative to heparin covalent chains.

monomers can elicit drastically different cellular responses (ref. 20; incorporated by reference in its entirety).

Experiments conducted during development of embodiments herein to determine whether the supramolecular GAGs emulate heparin regulation of GF signaling. BMP-2 was selected as a model GF since heparin and HS enhance BMP-2 signaling by prolonging its bioavailability and inhibiting its antagonist noggin (refs. 3, 21, 22; incorporated by reference in its entirety). C2C12 mouse myoblasts, a well-known cell line for which differentiation into osteoblasts occurs upon exposure to BMP-2, were used. Cells were cultured with BMP-2 (75 ng/mL) in the presence of heparin, HS, or supramolecular GAGs for 3 days, and osteoblast differentiation was evaluated by monitoring expression of the osteogenic protein alkaline phosphatase (ALP). A dose

TABLE 1

Examples of GFs important for regenerative medicine, along with protein length and previously identified heparin binding domains.

| GF | GF length | Heparin Binding Domain | SEQ ID NO: |
|---|---|---|---|
| BMP-2 | 115 | 1 MQAKHKQRKR LKS 13 | 10 |
| BMP-4 | 106 | 1 KKNKNCRRH 9 | 11 |
| Noggin | 206 | 106 GKKQR LSKKLRRKL 119 | 12 |
| Shh | 176 | 10 G KRRHPKK 17 | 13 |
| VEGF | 165 | 111 ARQENPCGPC SERRKHLFVQ DPQTCKCSCK NTDSRCKARQ LELNERTCRC DKPRR 165 | 14 |
| FGF-1 | 141 | 113 KKNGSCKR GPRTHYGQK 129 | 15 |
| FGF-2 | 154 | 128 RTG QYKLGSKTGP GQKA 144 | 16 |

The interactions between glycopeptide nanofibers and a heparin binding GF were investigated using confocal fluorescence imaging. For visualization, PAs 1 or 4 were co-assembled with a small fraction of PA molecules labeled with a fluorescent cyanine dye (Cy3-PA, 5 mol %), and BMP-2 as a model GF was fluorescently labeled with a different cyanine dye (Cy5). PA nanofibers and BMP-2 were allowed to mix for 24 h before imaging. Confocal microscopy revealed a strong colocalization of BMP-2 along the fibrous nanostructures of trisulfated PA 1 (FIG. 6A, top), and in great contrast BMP-2 did not localize with nonsulfated PA 4 nanofibers (FIG. 6A, bottom). To eliminate any potential artifacts from dye-dye interactions, fluorescently labeled BMP-2 was mixed with non-fluorescent PA nanofibers, and filamentous profiles were clearly observed (FIG. 6B).

Figure 9:
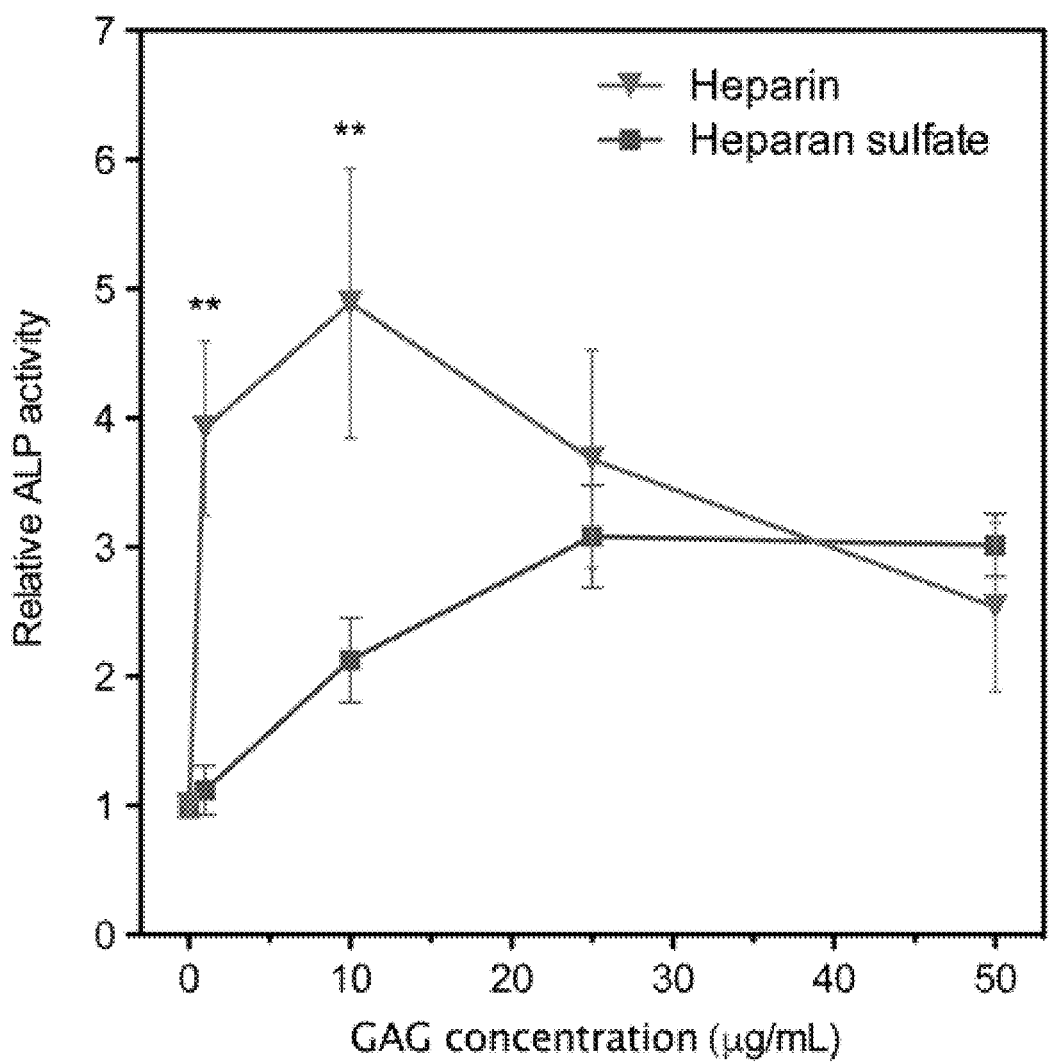
FIG. 9. Effect of heparin and HS on BMP-2 signaling in C2C12 cells. As a marker for BMP-2 signaling, alkaline phosphatase (ALP) activity is plotted as a function of increasing polysaccharide concentration.

In addition, SAXS was performed to measure the influence of GF binding on glycopeptide self-assembly. Upon mixing with BMP-2 or other GFs, changes in the X-ray scattering of glycopeptide nanofibers were not observed (FIG. 7). GFs alone did not scatter X-rays, indicating that the binding of GFs does not disrupt the fiber morphology. Also, circular dichroism (CD) measurements revealed that the β-sheet secondary structure of the glycopeptide nanofibers remained unperturbed by the addition of the heparin binding GFs (FIG. 8). Although the monomeric units are connected by noncovalent interactions, this binding substrate remained structurally invariant upon binding GFs, indicating that the glycosylated assemblies are architecturally stable to permit association with multiple proteins. Maintaining the structural integrity of the biomimetic nanofibers may be important since different nanofiber morphologies of identical response increase in osteoblast differentiation was observed by both heparin and HS (FIG. 9), but in agreement with previous work, heparin exhibited a more potent response than HS (ref. 3; incorporated by reference in its entirety). Heparan sulfate was found to enhance the level of ALP expression by a factor of 3 and heparin by a factor of 5. The supramolecular GAGs revealed in this assay a level of ALP expression that was 9 times higher than BMP-2 alone.

Figure 10:
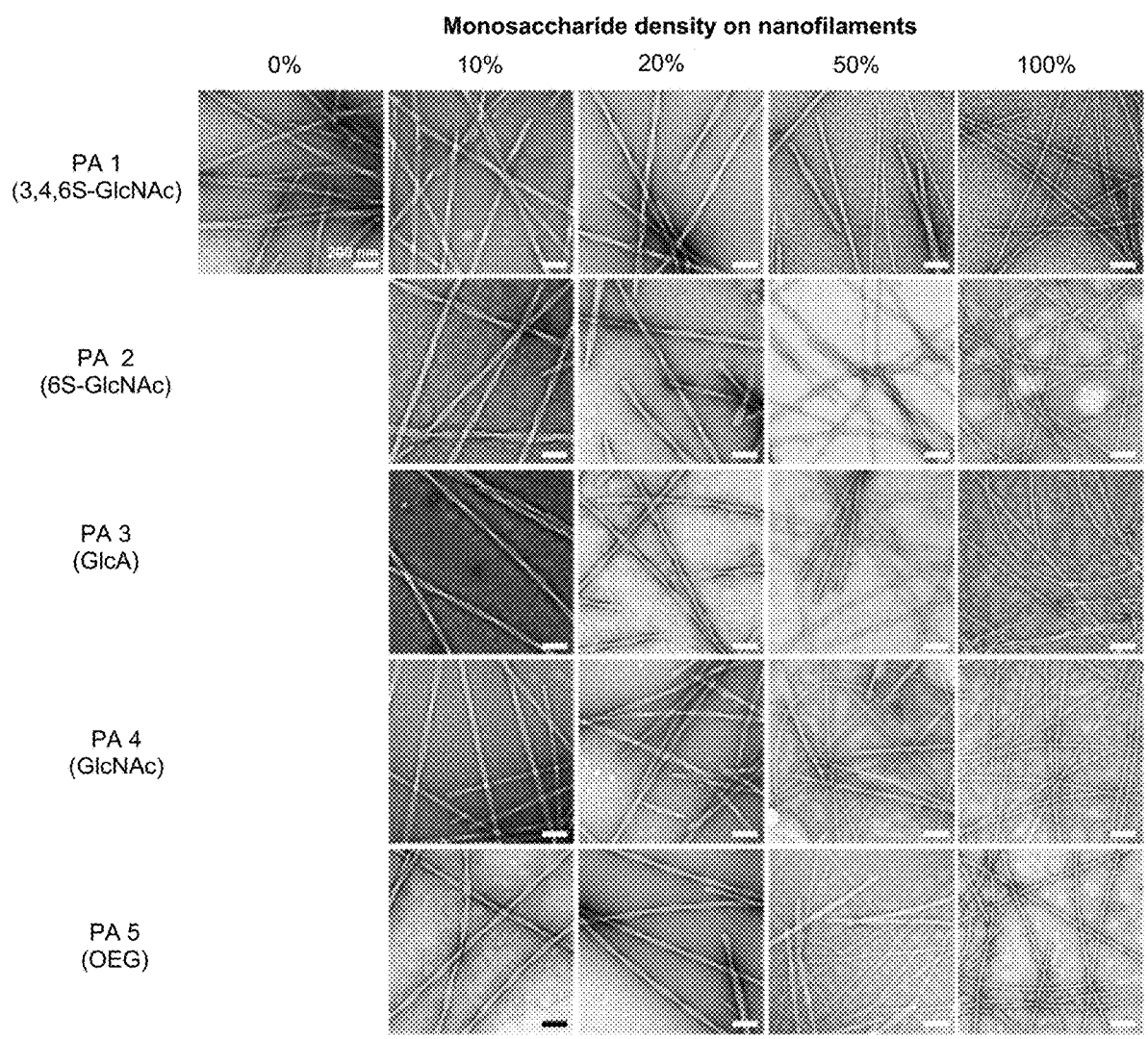
FIG. 10. Representative conventional TEM images of filaments of PAs 1-5, each co-assembled with the non-glycosylated PA6 at varied ratios to yield 0, 10, 20, 50, and 100% monosaccharide (or oligo(ethylene glycol), OEG) densities on the nanofilaments. Scalebar: 200 nm.
Figure 11A:
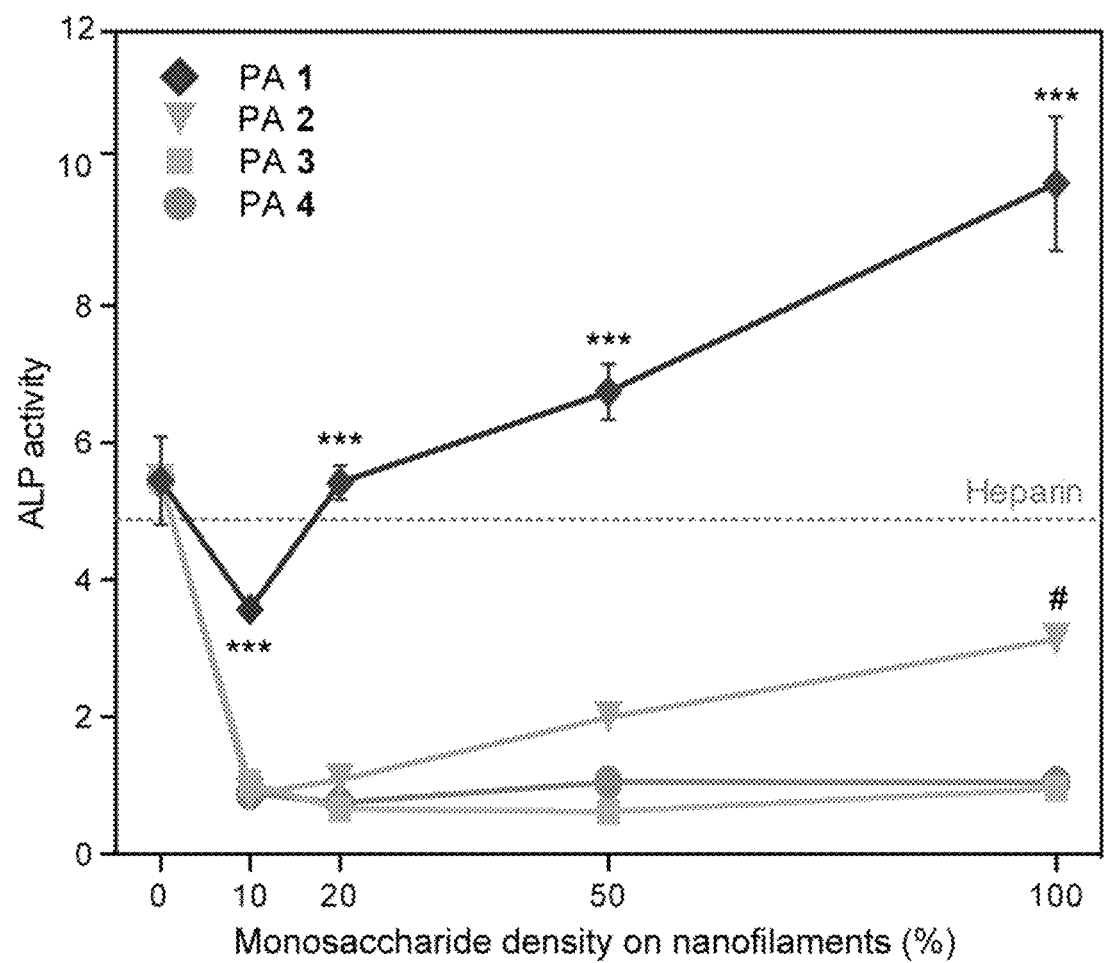
FIGS. 11A-E. (A) Plot of ALP activity in C2C12 cells treated with BMP-2 (75 ng/mL) and glycopeptide nanofibers (25 μM), as a function of increasing monosaccharide density on the nanofibers. Treatment with heparin (35 μM) is indicated by the dashed line. (B) Reverse transcription polymerase chain reaction (RT-PCR) experiments evaluating ALP and Osteocalcin (OCN) gene expressions following various treatments. (C) BMP-2 or BMP-4 induced ALP activity following treatment with PA 1 nanofibers or non-assembled monosaccharide 1. (D) Bar graphs of ALP activity using wild-type BMP-2 or a BMP-2 that has been mutated (EHBMP-2) at the N-terminal heparin-binding domain. In the protein sequence, basic residues are colored in red. (E) Effect of PA 1 nanofiber on noggin inhibition of BMP-2 activity.
Figure 12:
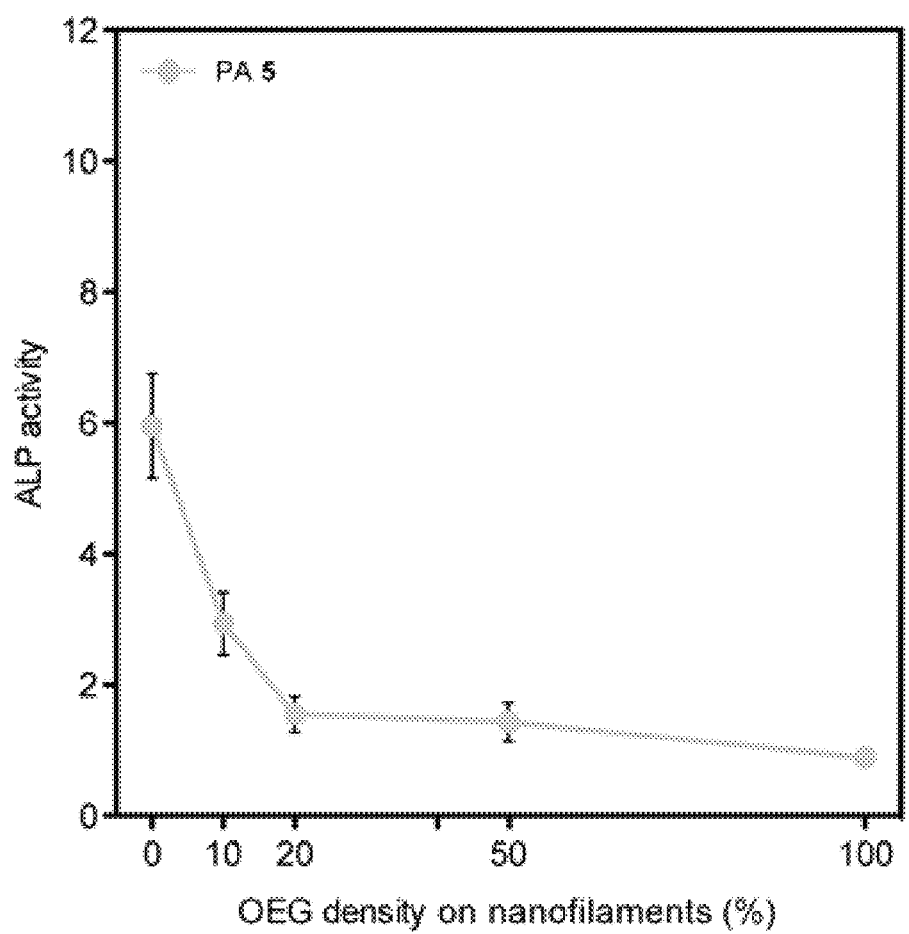
FIG. 12. Effect of PA 5 on BMP-2 signaling in C2C12 cells. PA 6 was diluted with increasing density of PA 5, and the effect of the co-assembled nanostructures on BMP-2 signaling was evaluated by assessing the ALP activity (25 µM PA).

Upon exposure to the supramolecular GAGs (25 µM), the augmentation of BMP-2 activity strongly depended on the nature of the monosaccharide and its density on nanofiber surfaces. A series of supramolecular GAGs was evaluated by co-assembling PAs 1-4 with the non-glycosylated PA 6 (these assemblies all revealed the formation of similar nanofibers, FIG. 10). PA 6 alone (0% monosaccharide density) resulted in a 5-fold increase in ALP activity (FIG. 11A), likely due to non-specific, coulombic interactions between the acidic nanofilaments and basic BMP-2 (ref. 23). In contrast, ALP activity was not to enhanced when PA 3 or 4 were incorporated at the level of 10% or higher (FIG. 11A). These results indicate that nanofibers formed by these co-assemblies exhibit non-fouling behavior towards proteins and cells. This phenomenon is well known in the context of epithelial cell membranes and bacteria, which display similar behavior as a result of their glycocalyx (ref. 24; incorporated by reference in its entirety). In fact, inspired by the glycocalyx, synthetic non-fouling surfaces have been developed using nonionic oligosaccharides or poly(ethylene glycol) (ref. 25, 26; incorporated by reference in their entireties). As further support, PA 5, which is end-functionalized with oligo(ethylene glycol), was co-assembled with PA 6 and a negligible effect on the enhancement of BMP-2 activity was observed (FIG. 12). Furthermore, zeta potential measurements revealed that the presence of GlcNAc and oligo(ethylene glycol) (PAs 4, 5) indeed screened the net negative charge on nanofiber surfaces compared to those formed by PA 6 (FIG. 1D).

Figure 11B:
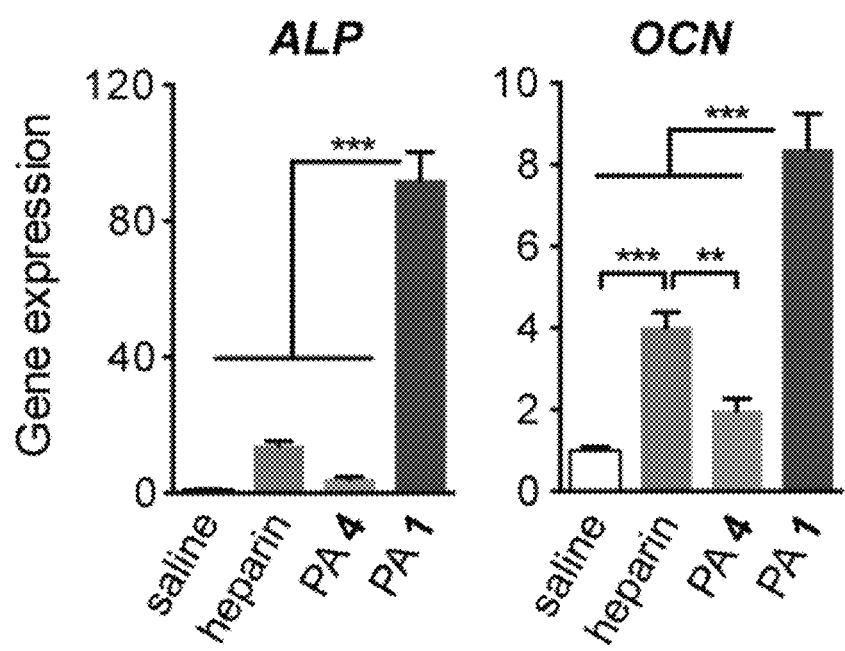
Figure 13:
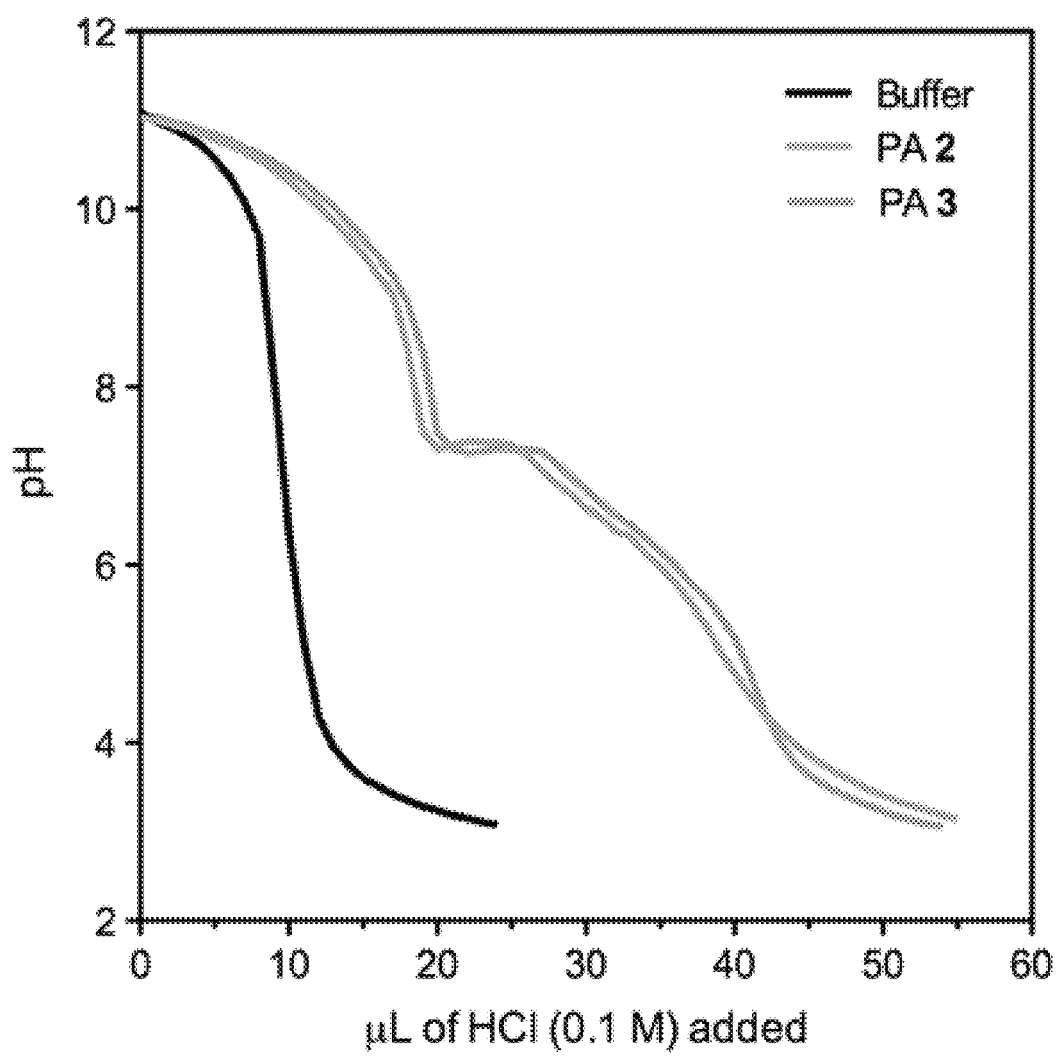
FIG. 13 Titration curves of PAs 2 and 3, as well as a control buffer, as a function of HCl added. Similar titration behaviors are observed for both PAs. (25 µM PA).
Figure 14:
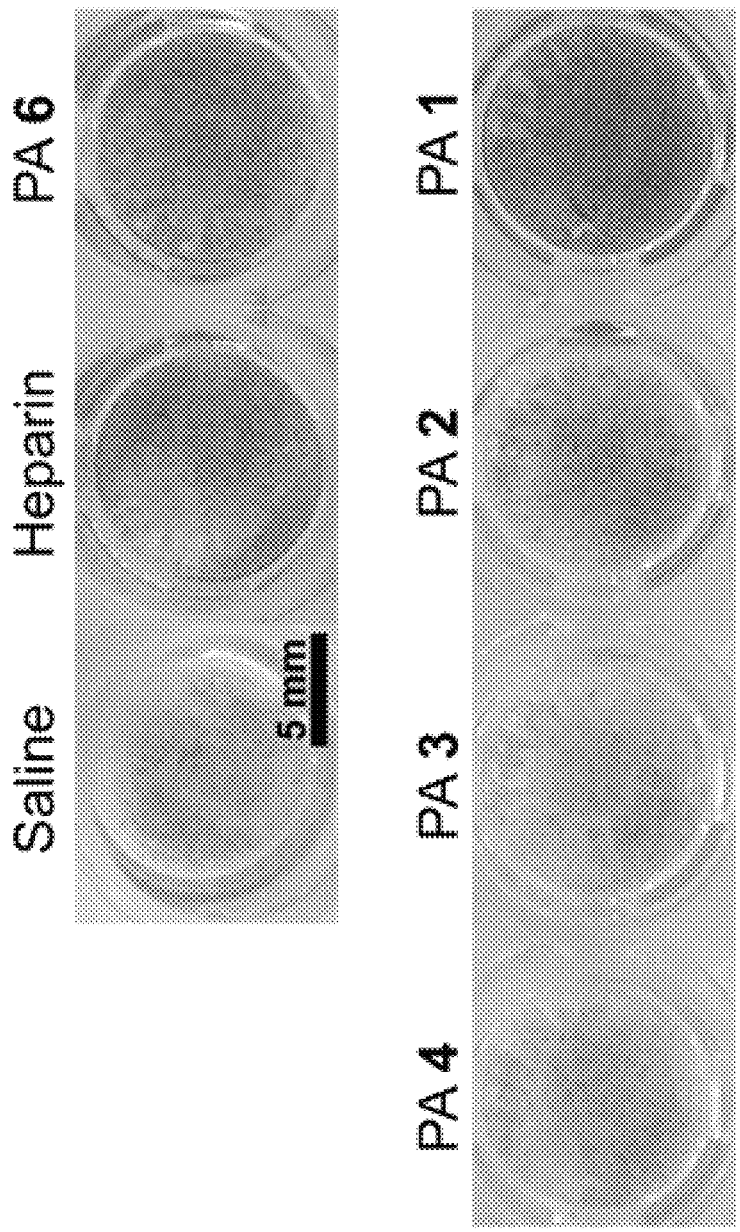
FIG. 14. Effect of the PAs 1-6 (25 µM PA) and heparin (35 µM) on BMP-2 signaling in C2C12 cells. Three days after treatment, cells were stained for the presence of ALP.

Supramolecular GAGs containing negatively charged glucuronic acid moieties (PA 3) did not potentiate BMP-2 activity (FIG. 11A). In the case of nanofibers containing a monosulfated monosaccharide (PA 2), a moderate 3-fold increase in BMP-2 signaling was observed (FIG. 11A). These two negatively charged PA nanofibers have comparable zeta potentials (FIG. 1D) and their aqueous solutions exhibit effectively identical changes in pH when HCl is titrated (FIG. 13). Therefore, this observation cannot be explained by charge density differences. On the other hand, sulfates are known to form stronger salt bridges with the side chains of lysine and arginine relative to carboxylates (ref. 27; incorporated by reference in its entirety). Since lysine and arginine are common amino acids in the heparin binding domains of proteins, it is contemplated that the difference between carboxylates and sulfates explains the results with PA 3 versus PA 2. Supramolecular GAGs containing the trisulfated monosaccharide 3,4,6S-GlcNAc (PA 1) dramatically amplified BMP-2 signaling (FIG. 11A, and FIG. 14). At 100% monosaccharide density, PA 1 nanofibers enhanced ALP activity by 9-fold, significantly higher than other glycosylated nanofibers, non-glycosylated PA 6 nanofibers, or the naturally occurring sulfated polysaccharides, heparin and heparan sulfate. The high charge on PA 1 nanofibers revealed by zeta potential measurements (FIG. 1D) is likely to be part of the stronger interaction between these supramolecular assemblies and BMP-2. It was also found that PA 1 nanofibers promoted higher expressions of ALP and osteocalcin mRNA relative to heparin or the PA nanofibers displaying uncharged GlcNAc residues (FIG. 11B).

Figure 11C:
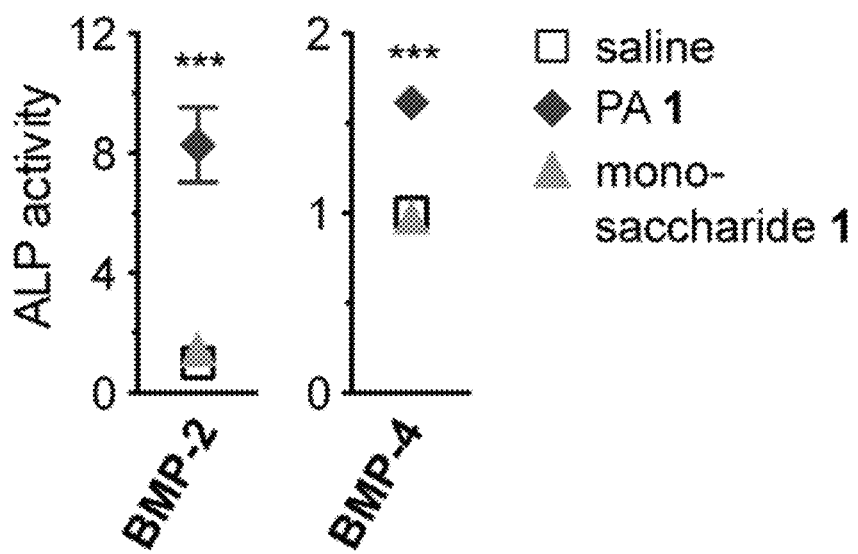
Figure 11D:
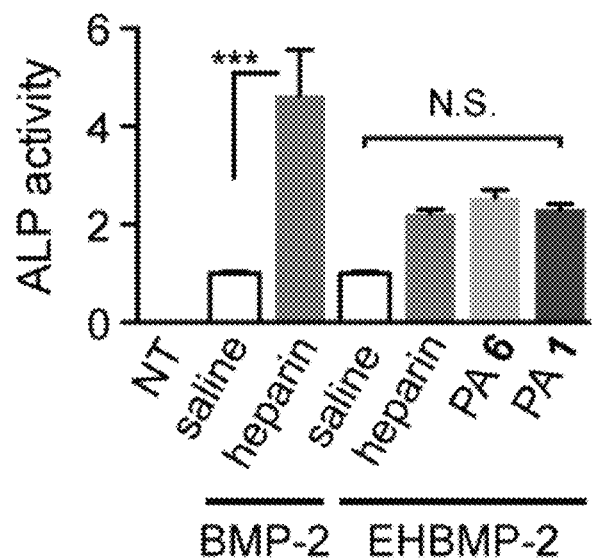
Figure 15:
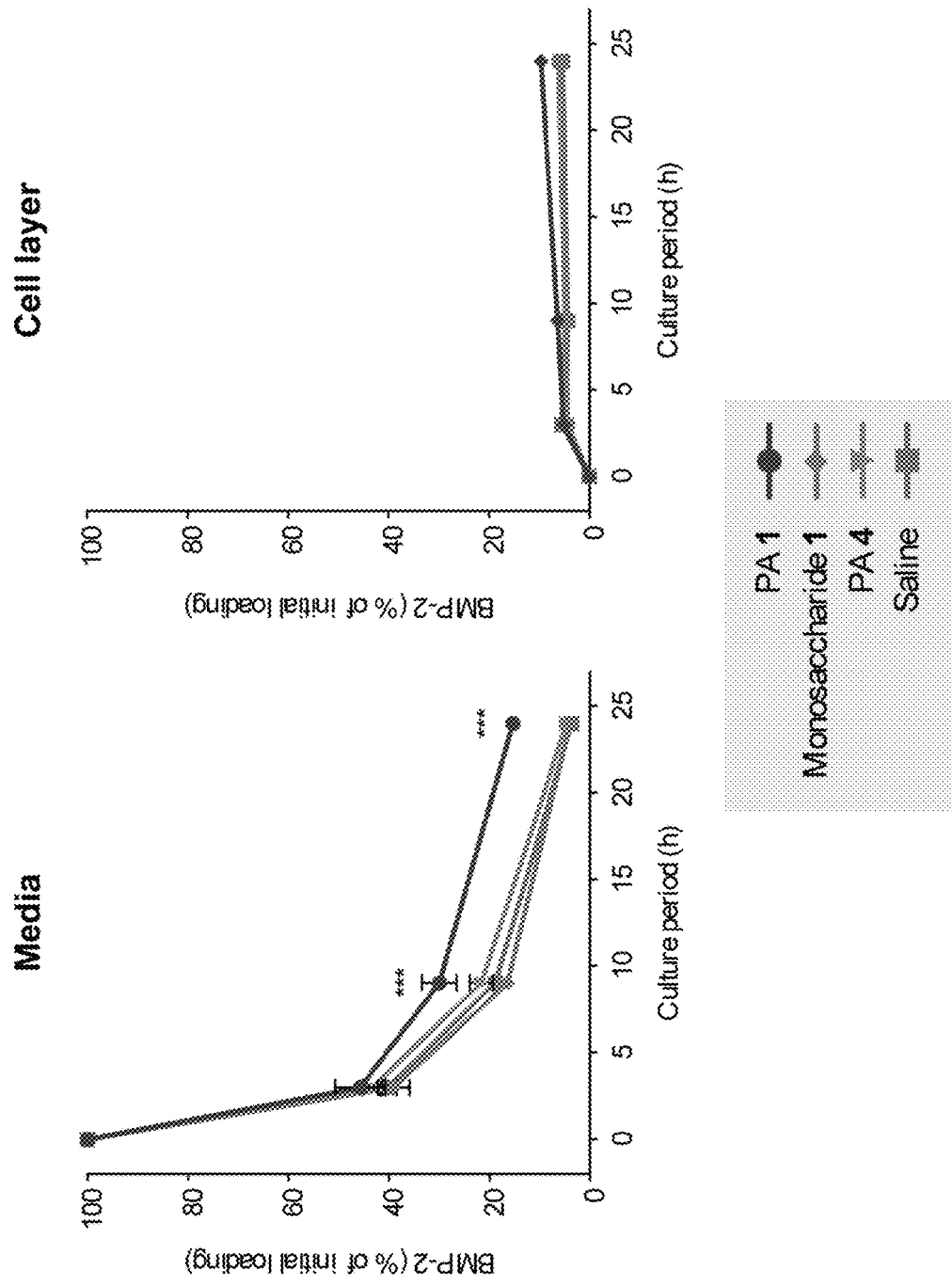
FIG. 15. C2C12 cells were treated with 75 ng/ml BMP-2 at time 0 in the presence of PA 1, PA 4, and Monosaccharide 1. The amounts of BMP-2 in the cell media (left panel) and cell extracts (right panel) were determined by enzyme-linked immunosorbant assay at each time point (0, 3, 9, and 24 h).

In the SPR analyses (see FIG. 4), the azide-derivative of trisulfated monosaccharide 1 bound neither BMP-2 nor BMP-4, another osteogenic heparin binding GF similar to BMP-2 (ref. 20; incorporated by reference in its entirety). It was therefore tested here if monosaccharide 1 amplified BMP-2 and BMP-4 signaling in C2C12 cells, which was not to be the case (FIG. 11C). Also, heparin and HS are known to prolong the half-life of BMP-2 (refs. 3, 21; incorporated by reference in their entireties), and improved BMP-2 stability was observed in cell culture media in the presence of PA 1 nanofibers, but not in the presence of monosaccharide 1 (FIG. 15). Experiments conducted during development of embodiments herein indicate that the collective interactions afforded by supramolecular assemblies of PA 1 are necessary to bind GFs and regulate their bioactivity. Next, the binding mechanism of PA 1 supramolecular assemblies were investigated using a mutant form of BMP-2 (EHBMP-2) that activates Smad phosphorylation to the same degree as the wild type BMP-2 while possessing negligible binding affinity to heparin (refs. 11, 28; incorporated by reference in their entireties). These experiments demonstrate that wild type BMP-2 signaling is definitely affected by the removal of cell surface HS by heparitinase, but the mutant protein EHBMP-2 remains unaffected by the absence of HS (ref. 28; incorporated by reference in its entirety). It was found that ALP expression using EHBMP-2 was also minimally affected by PA 1 nanofibers (FIG. 11D), mirroring the previous results on the mutant protein. This observation indicates that the glycomimetic nanofibers interact with the heparin binding pocket of wild type BMP-2.

Figure 11E:
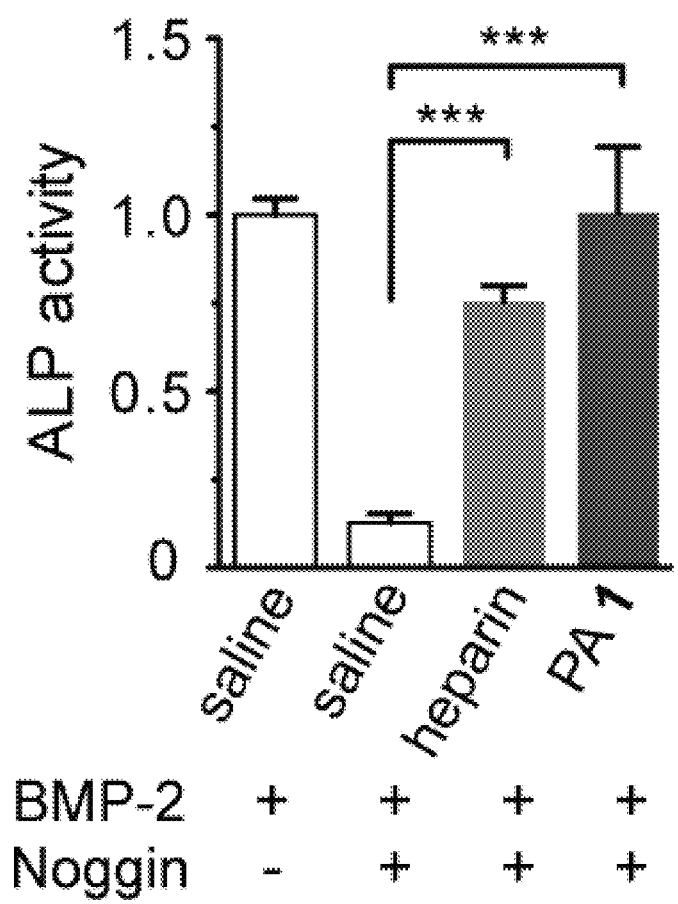
Figure 16:
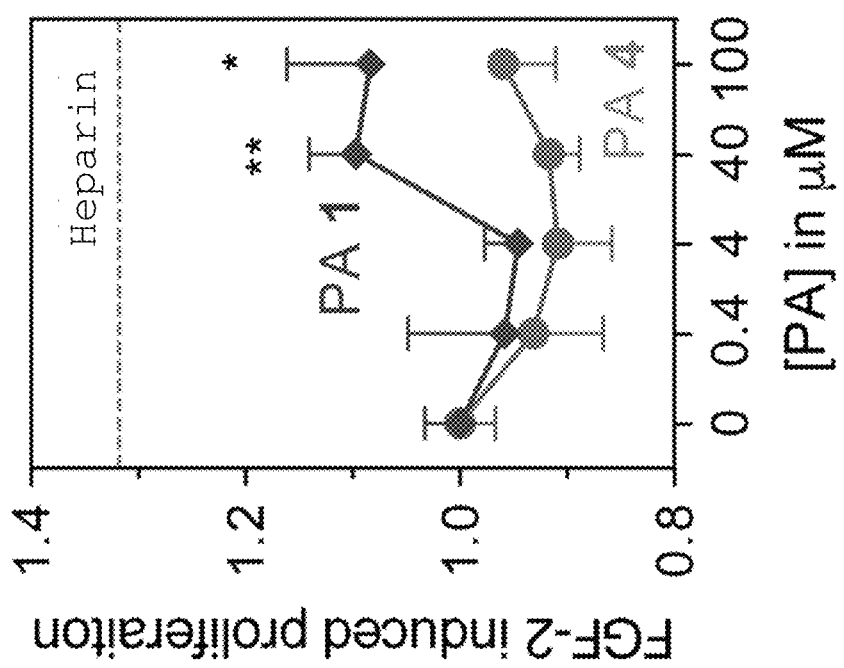
FIG. 16. Proliferation studies of BaF3-FR1C cells in the presence of FGF-2 (10 ng/ml), treated with blank saline, heparin (35 µM), or varied concentrations of PA 1 and PA 4 nanofibers.

Sulfated polysaccharides also regulate noggin (ref. 21; incorporated by reference in its entirety). While noggin antagonizes BMPs, heparin binds and inhibits noggin activity, thereby rescuing BMP signaling and the subsequent ALP expression in C2C12 cells. Exposure to PA 1 nanofibers also successfully protected BMP-2 from noggin antagonist during osteoblast differentiation (FIG. 11E). Furthermore, the influence of the supramolecular GAGs on FGF signaling was assessed using BaF3-FR1C cells, which require exogenous heparin or HS to promote FGF-FGF receptor interaction (ref. 5; incorporated by reference in its entirety). Heparin enhances signaling by FGF-2, and it was observed that the trisulfated PA 1 nanofibers also improved FGF-2 mediated cell proliferation (FIG. 16). These results provide further evidence that the highly sulfated supramolecular GAGs, as a novel heparin variant, can recapitulate certain biological functions of heparin and HS that are relevant to bone regeneration and blood vessel formation.

Figure 17A:
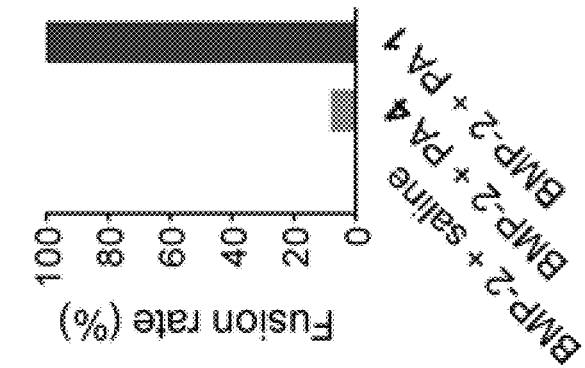

Experiments conducted during development of embodiments herein to investigate the translational potential of the supramolecular GAGs. Ideal biomaterials for tissue regeneration are not anticoagulant, since hematoma formation is the first stage of wound repair (ref. 29). By monitoring Factor Xa activity that is inhibited by heparin-activated antithrombin, it was observed that PA 1 nanofibers exhibited minimal anticoagulation activity compared to heparin (FIG. 17A). A highly specific pentasaccharide sequence in heparin is necessary for activating antithrombin (ref. 30; incorporated by reference in its entirety), indicating that the 3,4,6S-GlcNAc monosaccharides in PA 1 assemblies simply do not mimic the characteristic pentasaccharide.

Figure 17B:
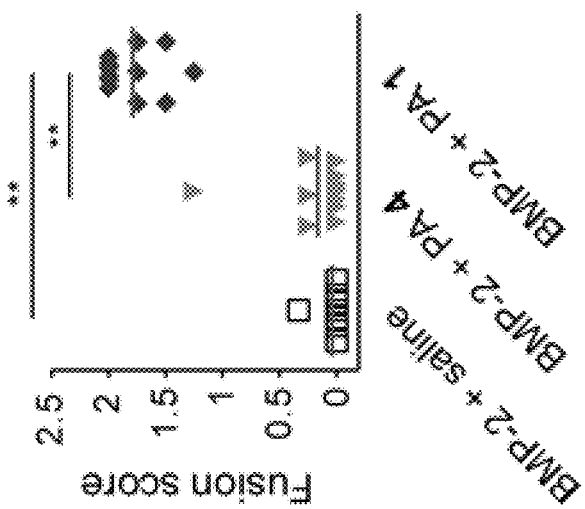
Figure 17C:
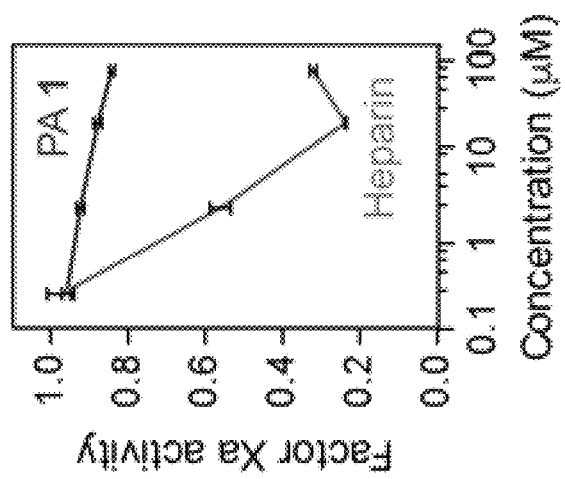

Next, the supramolecular GAGs were evaluated in a well-established rat posterolateral lumbar intertransverse spinal fusion model, which requires 10 µg BMP-2 loaded on a collagen sponge for effective bilateral fusion between L4 and L5 transverse processes (ref. 23; incorporated by reference in its entirety). Animals were treated with a dose of BMP-2 that is 100 times lower than that required in the model (100 ng) in the presence or absence of the glycopeptide nanofibers (6 mM). Eight weeks post-treatment, blind manual palpation analyses demonstrated that PA 1 nanofibers elicited the highest fusion scores relative to PA 4 nanofibers or saline (FIG. 17B). PA 1 nanofibers led to a 100% fusion rate using the very low sub-therapeutic dose of BMP-2 (FIG. 17C), thereby reducing the required GF by 100-fold. Furthermore, using synchrotron X-ray micro-computed tomography, the formation of new bone connecting the transverse processes when the low dose BMP-2 (100 ng) was delivered with PA 1 nanofibers was verified (FIGS. 17D-F). The 100-fold reduction in GF amount necessary for spinal fusion is of critical importance in the clinical use of BMP-2 due to the dangerous side effects that have been reported recently in patients (ref. 31; incorporated by reference in its entirety).

Figure 18:
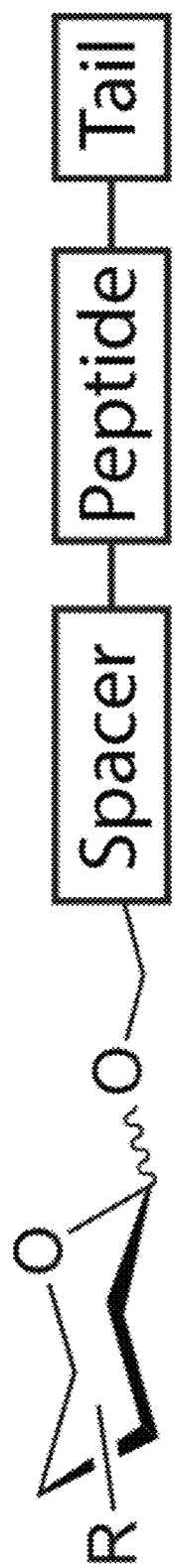
FIG. 18. Schematic molecular structure of a glycoconjugate. The sugar epitope could be mono-, di-, and oligosaccharides; R=—OH, —NHAc, —NH$_3$, —OPO$_3$H$_2$, —OSO$_3$H, —OSO$_3$X (X=counterion such as Na, K), —NHSO$_3$X (X=counterion such as Na, K), etc.; Spacer=hydrocarbon chain and/or oligoethylene glycol; Peptide=sequence of amino acids e.g., valines, alanines, glutamic acids and/or lysines; Tail=hydrophobic moeity.

As shown in FIG. 18, the amphiphilic molecule includes a hydrophobic portion derived from a hydrophobic tail connected via an amide bond or ester bond to a peptide (or peptide mimetic) sequence. The sequence of the peptide is a series of amino acids (e.g., valine, alanine, glutamic acid and/or lysine) and depends on the desired characteristics in terms of chemical elongation and conjugation, as well as the nanostructure architecture and biological applications. The peptide is further chemically conjugated to a spacer unit of hydrocarbons and/or oligoethylene glycols that presents at least one terminal carbohydrate epitope. Alternatively, a carbohydrate unit can be glycosylated directly to alcohols or amines functionalities in the peptide sequence using the amino acid motif as a spacer.

Several techniques are available for connecting the carbohydrate entity to the spacer (e.g., copper(I) catalyzed click reaction, copper-free click reaction, Staudinger ligation, phosphodiester, amide bond formation, etc.). The length of the saccharide backbone ranges from single monosaccharides (e.g., glucose, galactose, mannose, amino sugars, uronic acids, sialic acids) to oligosaccharides where the nature of the carbohydrate epitope includes functionalities such as amino groups, acetamides, carboxylic acids, phosphates, sulfates, and possible salts thereof and polysaccharide, or glycomimetics. The degree of sulfation per saccharide can vary from one to four sulfates with an exact control over their positions. The compounds characterized by general formula in FIG. 18 are single molecular entities such as either α- or β-anomers (1,2-cis/1,2-trans glycosides), but even mixtures of the two isomers can occur. FIG. 18 are for illustrative purposes only and include mono-, di-, oligo-, or polysaccharide, or glycomimetics and does not imply any structural restrictions such as configurations.

Figure 19A:
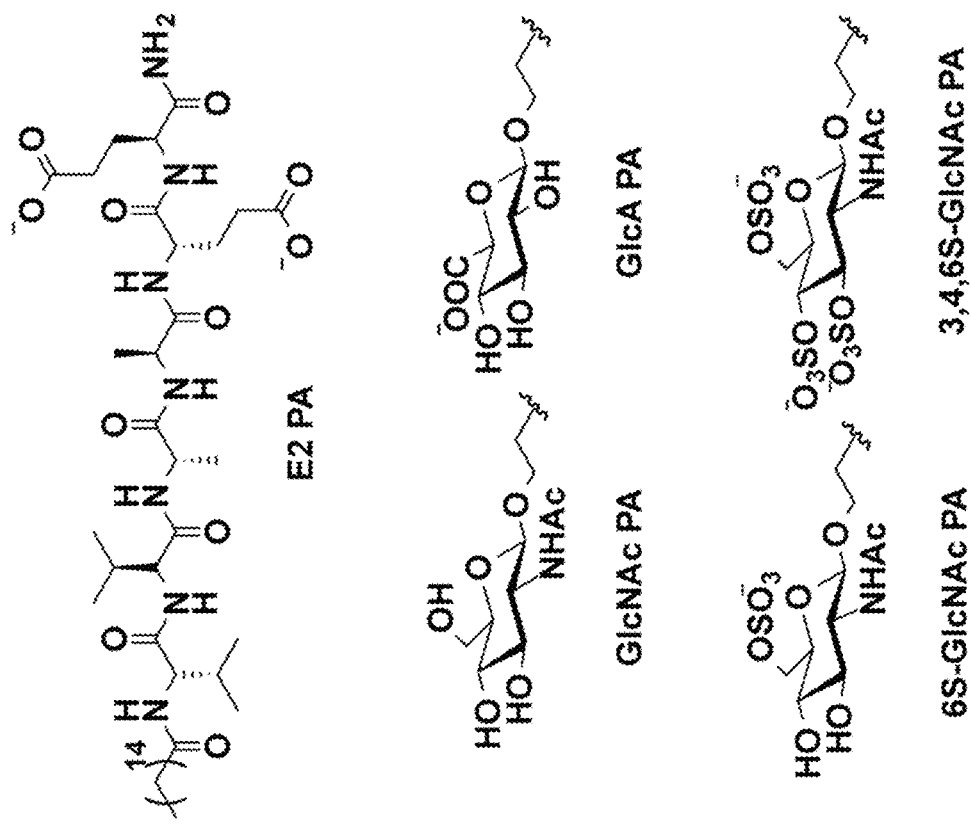
FIGS. 19A-B. Exemplary generic structure. E2 PA and Alkyne PA have been derived via solid phase peptide synthesis where Alkyne PA further has been functionalized with four monosaccharides, generating four GPAs (GlcNAc PA, GlcA PA, 6S-GlcNAc PA, and 3,4,6S-GlcNAc PA) to demonstrate the innovative character of the molecular design.
Figure 19B:
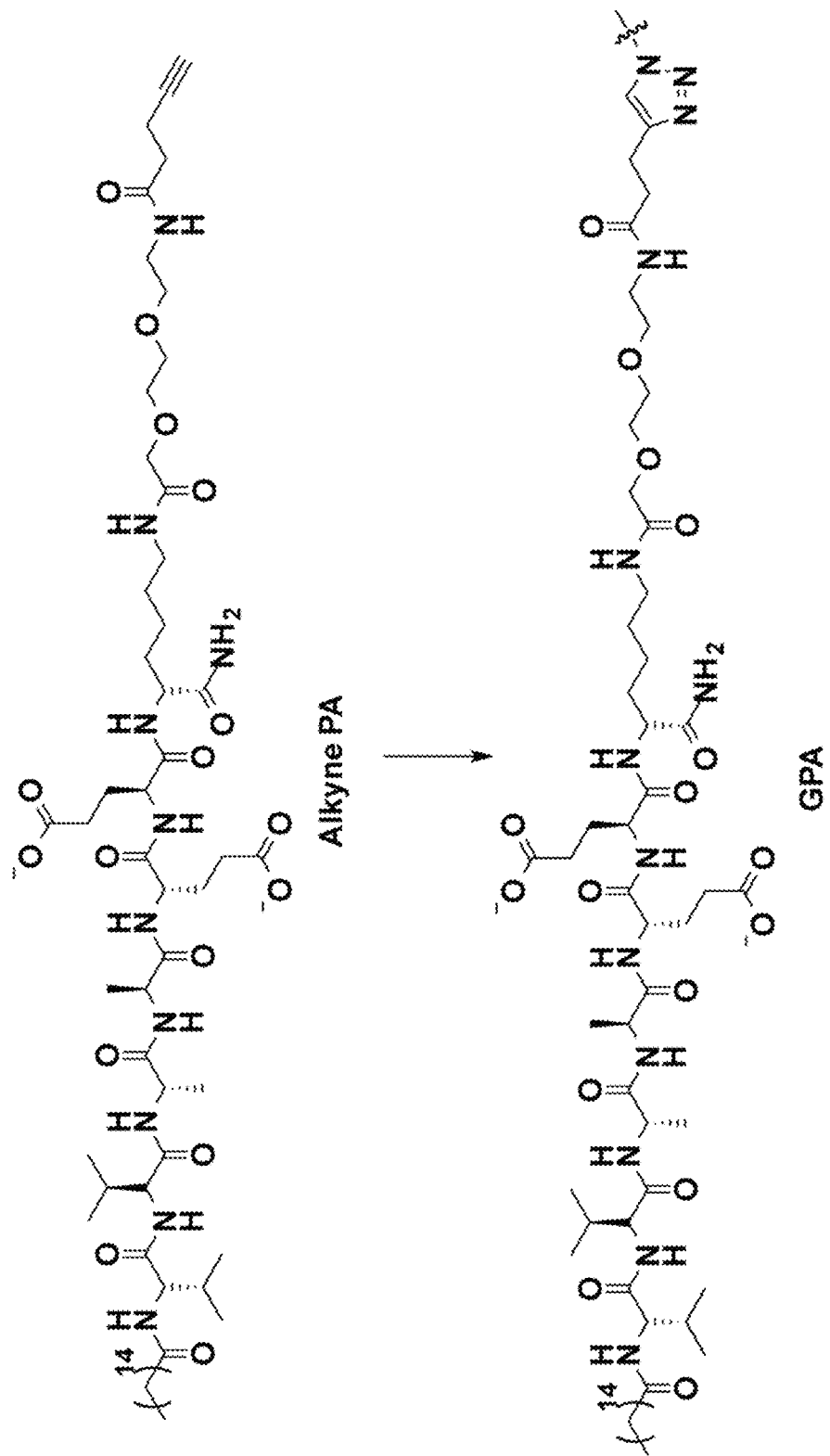

One aspect of the present invention provides a methodology suitable for the preparation of compounds, for example, of the general structure presented in FIG. 19. Examples of compounds derived and used herein are presented in FIG. 19, where "E2 PA" and "Alkyne PA" has been derived using solid phase peptide synthesis. "Alkyne PA" has further been used as one example of conjugation technique, the copper(I)catalyzed click reaction, to attach the carbohydrate epitopes to the PA backbone.

The 2-azido ethyl analogue of monosaccharides (GlcNAc (ref. 34; incorporated by reference in its entirety), GlcA (ref. 35; incorporated by reference in its entirety), 6S-GlcNAc, 3,4,6S-GlcNAc) was dissolved in a suitable solvent whereupon "Alkyne PA" was added. A Cu(I)— source or a combination of Cu(II)-source and a reducing agent (e.g., Na-ascorbate) was added and stirred to completion when water and a copper chelation resin (e.g., Chelex® 100) was added, vigorously shaked for 30 mins and filtered. The solution was treated with chelation resin 3×30 mins (or until the solution no longer contained copper ions) and evaporated. The crude reaction mixture was purified using basic HPLC followed by lyophilization.

To visually probe the interaction between the supramolecular GAG and proteins, fluorescent dyes can be conjugated to the amphiphilic molecule through, for instance copper(I) assisted click-reaction. This way the fluorescent probe will be covalently attached and the conjugate can be used in small portions and thereby not interrupt the bioactive epitope from interacting with the target biomolecule.

REFERENCES

The following references, many of which are referenced above by number, are herein incorporated by reference in their entireties.

1. Capila I, Linhardt R J. Heparin-protein interactions. Angewandte Chemie (International ed in English). 2002; 41(3):391-412.
2. Xu D, Esko J D. Demystifying heparan sulfate-protein interactions. Annu Rev Biochem. 2014; 83:129-57.
3. Bramono D S, Murali S, Rai B, Ling L, Poh W T, Lim Z X, Stein G S, Nurcombe V, van Wijnen A J, Cool S M. Bone marrow-derived heparan sulfate potentiates the osteogenic activity of bone morphogenetic protein-2 (BMP-2). Bone. 2012; 50(4):954-64.
4. Li Y C, Ho I H, Ku C C, Zhong Y Q, Hu Y P, Chen Z G, Chen C Y, Lin W C, Zulueta M M L, Hung S C, Lin M G, Wang C C, Hsiao C D. Interactions That Influence the Binding of Synthetic Heparan Sulfate Based Disaccharides to Fibroblast Growth Factor-2. Acs Chem Biol. 2014; 9(8):1712-7.
5. Ornitz D M, Leder P. Ligand specificity and heparin dependence of fibroblast growth factor receptors 1 and 3. The Journal of biological chemistry. 1992; 267(23): 16305-11.
6. Hartgerink J D, Beniash E, Stupp S I. Self-assembly and mineralization of peptide-amphiphile nanofibers. Science. 2001; 294(5547):1684-8.
7. Webber M J, Appel E A, Meijer E W, Langer R. Supramolecular biomaterials. Nature materials. 2015; 15(1):13-26.
8. Rostovtsev V V, Green L G, Fokin V V, Sharpless K B. A stepwise huisgen cycloaddition process: copper(I)-catalyzed regioselective "ligation" of azides and terminal alkynes. Angewandte Chemie. 2002; 41(14):2596-9.
9. Barceloux D G. Copper. J Toxicol-Clin Toxic. 1999; 37(2):217-30.
10. Ortony J H, Newcomb C J, Matson J B, Palmer L C, Doan P E, Hoffman B M, Stupp S I. Internal dynamics of a supramolecular nanofibre. Nature materials. 2014; 13(8):812-6.
11. Ruppert R, Hoffmann E, Sebald W. Human Bone Morphogenetic Protein 2 Contains a Heparin-Binding Site which Modifies Its Biological Activity. Eur J Biochem. 1996; 237(1):295-302.
12. Choi Y J, Lee J Y, Park J H, Park J B, Suh J S, Choi Y S, Lee S J, Chung C P, Park Y J. The identification of a heparin binding domain peptide from bone morphogenetic protein-4 and its role on osteogenesis. Biomaterials. 2010; 31(28):7226-38.
13. Paine-Saunders S, Viviano B L, Economides A N, Saunders S. Heparan sulfate proteoglycans retain Noggin at the cell surface—A potential mechanism for shaping bone morphogenetic protein gradients. Journal of Biological Chemistry. 2002; 277(3):2089-96.
14. Rubin J B, Choi Y, Segal R A. Cerebellar proteoglycans regulate sonic hedgehog responses during development. Development. 2002; 129(9):2223-32.
15. Ashikari-Hada S, Habuchi H, Kariya Y, Kimata K. Heparin regulates vascular endothelial growth factor165-dependent mitogenic activity, tube formation, and its receptor phosphorylation of human endothelial cells. Comparison of the effects of heparin and modified heparins. The Journal of biological chemistry. 2005; 280(36): 31508-15.
16. DiGabriele A D, Lax I, Chen D I, Svahn C M, Jaye M, Schlessinger J, Hendrickson W A. Structure of a heparin-linked biologically active dimer of fibroblast growth factor. Nature. 1998; 393(6687):812-7.
17. Schlessinger J, Plotnikov A N, Ibrahimi O A, Eliseenkova A V, Yeh B K, Yayon A, Linhardt R J, Mohammadi M. Crystal structure of a ternary FGF-FGFR-heparin complex reveals a dual role for heparin in FGFR binding and dimerization. Molecular cell. 2000; 6(3):743-50.
18. Silva G A, Czeisler C, Niece K L, Beniash E, Harrington D A, Kessler J A, Stupp S I. Selective differentiation of neural progenitor cells by high-epitope density nanofibers. Science. 2004; 303(5662):1352-5.
19. Mammen M, Choi S K, Whitesides G M. Polyvalent interactions in biological systems: Implications for design and use of multivalent ligands and inhibitors. Angewandte Chemie (International ed in English). 1998; 37(20):2755-94.
20. Tantakitti F, Boekhoven J, Wang X, Kazantsev R V, Yu T, Li J, Zhuang E, Zandi R, Ortony J H, Newcomb C J, Palmer L C, Shekhawat G S, de la Cruz M O, Schatz G C, Stupp S I. Energy landscapes and functions of supramolecular systems. Nature materials. 2016.
21. Zhao B, Katagiri T, Toyoda H, Takada T, Yanai T, Fukuda T, Chung Ui, Koike T, Takaoka K, Kamijo R. Heparin Potentiates the in Vivo Ectopic Bone Formation Induced by Bone Morphogenetic Protein-2. The Journal of biological chemistry. 2006; 281(32):23246-53.
22. Murali S, Rai B, Dombrowski C, Lee J L J, Lim Z X H, Bramono D S, Ling L, Bell T, Hinkley S, Nathan S S, Hui J H, Wong H K, Nurcombe V, Cool S M. Affinity-selected heparan sulfate for bone repair. Biomaterials. 2013; 34(22):5594-605.
23. Lee S S, Hsu E L, Mendoza M, Ghodasra J, Nickoli M S, Ashtekar A, Polavarapu M, Babu J, Riaz R M, Nicolas J D, Nelson D, Hashmi S Z, Kaltz S R, Earhart J S, Merk B R, McKee J S, Bairstow S F, Shah R N, Hsu W K, Stupp S I. Gel scaffolds of BMP-2-binding peptide amphiphile nanofibers for spinal arthrodesis. Advanced healthcare materials. 2015; 4(1):131-41.
24. Van Teeffelen J W, Brands J, Stroes E S, Vink H. Endothelial glycocalyx: sweet shield of blood vessels. Trends Cardiovasc Med. 2007; 17(3):101-5.
25. Fyrner T, Lee H-H, Mangone A, Ekblad T, Pettitt M E, Callow M E, Callow J A, Conlan S L, Mutton R, Clare A S, Konradsson P, Liedberg B, Ederth T. Saccharide-Functionalized Alkanethiols for Fouling-Resistant Self-Assembled Monolayers: Synthesis, Monolayer Properties, and Antifouling Behavior. Langmuir. 2011; 27(24): 15034-47.
26. Bearinger J P, Terrettaz S, Michel R, Tirelli N, Vogel H, Textor M, Hubbell JA. Chemisorbed poly(propylene sulphide)-based copolymers resist biomolecular interactions. Nature materials. 2003; 2(4):259-64.
27. Gandhi N S, Mancera R L. The Structure of Glycosaminoglycans and their Interactions with Proteins. Chem Biol Drug Des. 2008; 72(6):455-82.
28. Kuo W J, Digman M A, Lander A D. Heparan Sulfate Acts as a Bone Morphogenetic Protein Coreceptor by Facilitating Ligand-induced Receptor Hetero-oligomerization. Mol Biol Cell. 2010; 21(22):4028-41.
29. Eming S A, Martin P, Tomic-Canic M. Wound repair and regeneration: mechanisms, signaling, and translation. Science translational medicine. 2014; 6(265):265sr6.
30. Petitou M, van Boeckel C A. A synthetic antithrombin III binding pentasaccharide is now a drug! What comes next? Angewandte Chemie. 2004; 43(24):3118-33.
31. Simmonds M C, Brown J V, Heirs M K, Higgins J P, Mannion R J, Rodgers M A, Stewart L A. Safety and effectiveness of recombinant human bone morphogenetic protein-2 for spinal fusion: a meta-analysis of individual-participant data. Annals of internal medicine. 2013; 158 (12):877-89.
32. Tovar J D, Claussen R C, Stupp S I. Probing the interior of peptide amphiphile supramolecular aggregates. Journal of the American Chemical Society. 2005; 127(20):7337-45.
33. Webber M J, Newcomb C J, Bitton R, Stupp S I. Switching of Self-Assembly in a Peptide Nanostructure with a Specific Enzyme. Soft matter. 2011; 7(20):9665-72.
34. Eklind K, Gustafsson R, Tiden A K, Norberg T, Aberg P M. Large-scale synthesis of a Lewis B tetrasaccharide derivative, its acrylamide copolymer, and related di- and trisaccharides for use in adhesion inhibition studies with *Helicobacter pylori*. J Carbohyd Chem. 1996; 15(9): 1161-78.
35. Chernyak A, Kononov L O, Kochetkov N K. Synthesis of carbohydrate-amino acid conjugates related to the capsular antigen K54 from *Escherichia coli* O6:K54:H10 and artificial antigens therefrom. Carbohydr Res. 1991; 216:381-98.
36. Chen B, Baumeister U, Pelzl G, Das M K, Zeng X, Ungar G, Tschierske C. Carbohydrate rod conjugates: ternary rod-coil molecules forming complex liquid crystal structures. Journal of the American Chemical Society. 2005; 127(47):16578-91.
37. Billington C J, Fiebig J E, Forsman C L, Pham L, Burbach N, Sun M, Jaskoll T, Mansky K, Gopalakrishnan R, O' Connor M B, Mueller T D, Petryk A. Glycosylation of Twisted Gastrulation is Required for BMP Binding and Activity during Craniofacial Development. Front Physiol. 2011; 2:59.
38. Katagiri T, Yamaguchi A, Komaki M, Abe E, Takahashi N, Ikeda T, Rosen V, Wozney J M, Fujisawa-Sehara A, Suda T. Bone morphogenetic protein-2 converts the differentiation pathway of C2C12 myoblasts into the osteoblast lineage. The Journal of Cell Biology. 1994; 127(6): 1755-66.
39. Chou Y F, Dunn J C, Wu BM. In vitro response of MC3T3-E1 pre-osteoblasts within three-dimensional apatite-coated PLGA scaffolds. Journal of biomedical materials research Part B, Applied biomaterials. 2005; 75(1): 81-90.
40. Nguyen T H, Paluck S J, McGahran A J, Maynard H D. Poly(vinyl sulfonate) Facilitates bFGF-Induced Cell Proliferation. Biomacromolecules. 2015; 16(9):2684-92. doi: 10.1021/acs.biomac.5b00557. PubMed PMID: WOS: 000361341700014.
41. Hsu W K, Wang J C, Liu N Q, Krenek L, Zuk P A, Hedrick M H, Benhaim P, Lieberman JR. Stem cells from human fat as cellular delivery vehicles in an athymic rat posterolateral spine fusion model. The Journal of bone and joint surgery American volume. 2008; 90(5):1043-52.
42. Wang Y X, De Carlo F, Mancini D C, McNulty I, Tieman B, Bresnahan J, Foster I, Insley J, Lane P, von Laszewski G, Kesselman C, Su M H, Thiebaux M. A high-throughput x-ray microtomography system at the Advanced Photon Source. Rev Sci Instrum. 2001; 72(4):2062-8.
43. Singhal A, Stock S R, Almer J D, Dunand D C. Effect of cyclic loading on the nanoscale deformation of hydroxyapatite and collagen fibrils in bovine bone. Biomech Model Mechan. 2014; 13(3):615-26.
44. Gursoy D, De Carlo F, Xiao X, Jacobsen C. TomoPy: a framework for the analysis of synchrotron tomographic data. Journal of synchrotron radiation. 2014; 21(Pt 5):1188-93.

The invention claimed is:

1. A composition comprising a supramolecular glyconanostucture, the supramolecular glyconanostucture comprising a nanofiber of glycosylated peptide amphiphiles (GPAs) self-assembled into a nanofiber; wherein the GPAs comprise a hydrophobic non-peptide tail, a structured peptide segment, a charged peptide segment, and a terminal saccharide; and wherein the nanofiber comprises a hydrophobic core, peptide surface, and saccharides displayed on the surface.

2. The composition of claim 1, further comprising filler peptide amphiphiles (PAs), wherein the filler PAs comprise a hydrophobic non-peptide tail, a structured peptide segment, and a charged peptide segment, but lack a terminal saccharide.

3. The composition of claim 2, further comprising non-glycosylated bioactive PAs, wherein the non-glycosylated bioactive PAs comprise a hydrophobic non-peptide tail, a structured peptide segment, a charged peptide segment, and a non-saccharide bioactive terminal moiety.

4. The composition of claim 1, wherein the terminal saccharide is conjugated to the charged peptide segment by a linker.

5. The composition of claim 1, wherein the terminal saccharide is selected from the group consisting of a monosaccharide, a disaccharide, an oligosaccharide, and a glycomimetic.

6. The composition of claim 5, wherein the saccharide is selected from:
   (a) the monosaccharides consisting of GlcA, GlcNAc, GlcNS, IdoA, and sulfated versions thereof;
   (b) dissacharides of GlcA, GlcNAc, GlcNS, IdoA, and sulfated versions thereof;

(c) oligosaccharides of GlcA, GlcNAc, GlcNS, IdoA, and sulfated versions thereof;
(d) glycomimetics; and
(e) sulfated fucoidan disaccharide and oligosaccharides.

7. The composition of claim 6, wherein the saccharide is a monosaccharide or disaccharide comprising a sulfated version of one of GlcA, GlcNAc, GlcNS, or IdoA.

8. The composition of claim 6, wherein the saccharide is a monsaccharide of GlcNAc(3,4,6S).

9. The composition of claim 1, wherein the GPAs are glycosaminoglycan (GAG) mimetic peptide amphiphiles (PAs).

10. The composition of claim 9, wherein GAG mimetic peptide exhibits a biological activity of heparin, heparin sulfate, and/or hyaluronic acid.

11. The composition of claim 10, wherein the GAG mimetic peptide binds to a heparin binding domain of one or more of BMP-2, BMP-4, Noggin, VEGF, FGF-1, FGF-2, and/or Shh.

\* \* \* \* \*